US008680247B2

(12) United States Patent
Terrett et al.

(10) Patent No.: US 8,680,247 B2

(45) Date of Patent: Mar. 25, 2014

(54) MONOCLONAL ANTIBODIES AGAINST GLYPICAN-3

(75) Inventors: Jonathan Alexander Terrett, Sunnyvale, CA (US); Li-Sheng Lu, Mountain View, CA (US); Haichun Huang, Fremont, CA (US); Dapeng Yao, Milpitas, CA (US); Chin Pan, Los Altos, CA (US); Heidi Leblanc, Mountain View, CA (US); Timothy Sproul, Livermore, CA (US); Mark Yamanaka, Pleasanton, CA (US)

(73) Assignee: Medarex, L.L.C., Princeton, NJ (US)

( * ) Notice: Subject to any disclaimer, the term of this patent is extended or adjusted under 35 U.S.C. 154(b) by 420 days.

(21) Appl. No.: 12/668,965

(22) PCT Filed: Jul. 17, 2008

(86) PCT No.: PCT/US2008/070344

§ 371 (c)(1), (2), (4) Date: Jan. 13, 2010

(87) PCT Pub. No.: WO2009/012394

PCT Pub. Date: Jan. 22, 2009

(65) Prior Publication Data

US 2010/0209432 A1 Aug. 19, 2010

Related U.S. Application Data

(60) Provisional application No. 60/959,845, filed on Jul. 17, 2007.

(51) Int. Cl.

*C07K 16/30* (2006.01)
*A61K 39/395* (2006.01)
*A61K 39/44* (2006.01)
*C07K 16/46* (2006.01)

(52) U.S. Cl.

USPC ................ 530/388.8; 530/387.3; 530/388.15; 530/391.3; 424/174.1; 424/142.1; 424/133.1; 424/178.1

(58) Field of Classification Search

None

See application file for complete search history.

(56) References Cited

U.S. PATENT DOCUMENTS

| | | | |
|---|---|---|---|
| 7,744,800 | B2 | 6/2010 | Levenhagen et al. |
| 7,867,734 | B2 | 1/2011 | Nakano et al. |
| 7,871,613 | B2 | 1/2011 | Kinoshita et al. |
| 7,919,086 | B2 | 4/2011 | Nakano et al. |
| 7,943,743 | B2 * | 5/2011 | Korman et al. .......... 530/388.15 |
| 7,988,971 | B2 * | 8/2011 | Dimitrov et al. ........... 424/147.1 |
| 2004/0236080 | A1 * | 11/2004 | Aburatani et al. ....... 530/388.26 |
| 2006/0167232 | A1 * | 7/2006 | Aburatani et al. ......... 530/388.8 |
| 2012/0301490 | A1 * | 11/2012 | Zhang et al. .............. 424/181.1 |

FOREIGN PATENT DOCUMENTS

| | | | |
|---|---|---|---|
| EP | 1674111 | A1 | 6/2006 |
| JP | 1780273 | A1 | 5/2007 |
| WO | WO96/33735 | * | 10/1996 |
| WO | WO 03/000883 | | 1/2003 |
| WO | WO 2004/022595 | | 3/2004 |
| WO | WO 2004/022597 | | 3/2004 |
| WO | WO 2004/022754 | | 3/2004 |
| WO | WO 2004/023145 | | 3/2004 |
| WO | WO 2004/067571 | | 8/2004 |
| WO | WO 2005/001921 | | 1/2005 |
| WO | WO 2006/006693 | | 1/2006 |
| WO | WO 2006/022407 | | 3/2006 |
| WO | WO 2006/046751 | | 5/2006 |

OTHER PUBLICATIONS

Paul. Fundamental Immunology, 3rd Edition, 1993, pp. 292-295.*

Rudikoff, Giusti, Cook, and Scharff. Single amino acid substitution altering antigen binding specificity. Proceedings of the National Academy of Sciences, 1982. vol. 79, pp. 1979-1983.*

Colman. Effects of amino acid sequence changes on antibody antigen interactions. Research in Immunology, 1994. vol. 145, pp. 33-36.*

Mac Callum, Martin, and Thornton. Antibody antigen interactions: contact analysis and binding site topography. Journal of Molecular Biology, 1996. vol. 262, pp. 732-745.*

Paul, Fundamental Immunology, 3rd Edition, 1993, pp. 292-295.*

Muyldermans, Rev Mol Biotech 2001; 74:277-302.*

Rudikoff et al., Proc. Nat'l Acad. Sci. USA 1982; 79:1979-83.*

Brown et al., J. Immunol. 1996; 156(9):3285-91.*

Nakano et al., Biochem Biophys Res Com 2009; 378(2):279-284.*

Midorikawa, Y. et al., "Glypican-3, Overexpressed in Hepatocellular Carcinoma, Modulates FGF2 and BMP-7 Signaling", Int. J. Cancer, vol. 103, pp. 455-465 (2003).

Sung, Y. K. et al., "Glypican-3 is Overexpressed in Human Hepatocellular Carcinoma", Cancer Sci, vol. 94, No. 3, pp. 259-262 (2003).

U.S. Appl. No. 13/447,219, filed May 22, 2012, Zhang et al.

Greten, Tim F. et al., "Immunotherapy of hepatocellular carcinoma," Journal of Hepatology, vol. 45:868-878 (2006).

(Continued)

*Primary Examiner* — Sheela J Huff

*Assistant Examiner* — Jessica H Roark

(74) *Attorney, Agent, or Firm* — Z. Angela Guo

(57) ABSTRACT

The present disclosure provides isolated monoclonal antibodies, particularly human monoclonal antibodies that specifically bind to Glypican-3 with high affinity. Nucleic acid molecules encoding Glypican-3 antibodies, expression vectors, host cells and methods for expressing the Glypican-3 antibodies are also provided. Immunoconjugates, bispecific molecules and pharmaceutical compositions comprising the Glypican-3 antibodies are also provided. Methods for detecting Glypican-3, as well as methods for treating various Glypican-3-related conditions, including hepatocellular cancer, are disclosed.

21 Claims, 19 Drawing Sheets

(56) References Cited

OTHER PUBLICATIONS

Hippo, Yoshitaka et al., "Identification of Soluble NH2-Terminal Fragment of Glypican-3 as a Serological Marker for Early-Stage Hepatocellular Carcinoma," Cancer Research, vol. 2418-2423 (2004).

Nesterova, Albina et al., "Glypican-3 as a novel target for an antibody-drug conjugate," Proceedings of the American Association for Cancer Research, vol. 48:157, No. 656 (2007).

Yamauchi, Naoko et al., "The glypican 3 oncofetal protein is a promising diagnostic marker for hepatocellular carcinoma," Modern Pathology, vol. 18:1591-1598 (2005).

International Search Report and Written Opinion for Application No. PCT/US2008/070344, dated Nov. 19, 2008.

International Preliminary Report on Patentability for Application No. PCT/US2008/070344, dated Jan. 19, 2010.

* cited by examiner

Figure 1A: Anti-Glypican-3 4A6 $V_H$

```
V segment:     5-51
J segment:     JH4b

      E   V   Q   L   V   Q   S   G   A   E   V   K   K   P   G   E   S   L
  1 GAG GTG CAG CTG GTG CAG TCT GGA GCA GAG GTG AAA AAG CCC GGG GAG TCT CTG

                                                          CDR1
                                                      ~~~~~~~~~~~~~~~~~~~
      K   I   S   C   K   G   S   G   Y   S   F   T   S   Y   W   I   A   W
 55 AAG ATC TCC TGT AAG GGT TCT GGA TAC AGC TTT ACC ACC TAC TGG ATC GCC TGG

                                                              CDR2
                                                          ~~~~~~~~~~~~~~~~~~
      V   R   Q   M   P   G   K   G   L   E   W   M   G   I   I   F   P   G
109 GTG CGC CAG ATG CCC GGC AAA GGC CTG GAG TGG ATG GGG ATC ATC TTT CCT GGT

                  CDR2
    ~~~~~~~~~~~~~~~~~~~~~~~~~~~~~~~~~~~~~~~~~~~~~~~~~~
      D   S   D   T   R   Y   S   P   S   F   Q   G   Q   V   T   I   S   A
163 GAC TCT GAT ACC AGA TAC AGC CCG TCC TTC CAA GGC CAG GTC ACC ATC TCA GCC

      D   R   S   I   R   T   A   Y   L   Q   W   S   S   L   K   A   S   D
217 GAC AGG TCC ATC AGA ACC GCC TAC CTG CAG TGG AGC AGC CTG AAG GCC TCG GAC

                                                     CDR3
                                          ~~~~~~~~~~~~~~~~~~~~~~~~~~~~~~~~
      T   A   L   Y   Y   C   A   R   T   R   E   G   Y   F   D   Y   W   G
271 ACC GCC TTG TAT TAC TGT GCG AGA ACC CGG GAG GGG TAC TTT GAC TAC TGG GGC

      Q   G   T   L   V   T   V   S   S
325 CAG GGA ACC CTG GTC ACC GTC TCC TCA
```

>Glypican-3 4A6, VH-NT with leader
ATGGGGTCAACCGCCATCCTCGCCCTCCTCCTGGCTGTTCTCCAAGGAGTCTG
TGCCGAGGTGCAGCTGGTGCAGTCTGGAGCAGAGGTGAAAAAGCCCGGGGA
GTCTCTGAAGATCTCCTGTAAGGGTTCTGGATACAGCTTTACCAGCTACTGGA
TCGCCTGGGTGCGCCAGATGCCCGGGAAAGGCCTGGAGTGGATGGGGATCAT
CTTTCCTGGTGACTCTGATACCAGATACAGCCCGTCCTTCCAAGGCCAGGTCA
CCATCTCAGCCGACAGGTCCATCAGAACCGCCTACCTGCAGTGGAGCAGCCT
GAAGGCCTCGGACACCGCCTTGTATTACTGTGCGAGAACCCGGGAGGGGTAC
TTTGACTACTGGGGCCAGGGAACCCTGGTCACCGTCTCCTCA > Glypican-3 4A6, VH-AA with leader
MGSTAILALLLAVLQGVCAEVQLVQSGAEVKKPGESLKISCKGSGYSFTSYWIA
WVRQMPGKGLEWMGIIFPGDSDTRYSPSFQGQVTISADRSIRTAYLQWSSLKAS
DTALYYCARTREGYFDYWGQGTLVTVSS

Figure 1B: Anti-Glypican-3 4A6 $V_K$

```
V segment:     A27
J segment:     JK4


      E   I   V   L   T   Q   S   P   G   T   L   S   L   S   P   G   E   R
  1 GAA ATT GTG TTG ACG CAG TCT CCA GGC ACC CTG TCT TTG TCT CCA GGG GAA AGA

                                          CDR1
                          ~~~~~~~~~~~~~~~~~~~~~~~~~~~~~~~~~~~~~~~~~~~~~~~~~~
      A   T   L   S   C   R   A   V   Q   S   V   S   S   S   Y   L   A   W
 55 GCC ACC CTC TCC TGC AGG GCC GTT CAG AGT GTT AGC AGC AGC TAT TTA GCC TGG

                                                                  CDR2
                                                              ~~~~~~~~~~~~~~~
      Y   Q   Q   K   P   G   Q   A   P   R   L   L   I   Y   G   A   S   S
109 TAC CAG CAG AAA CCT GGC CAG GCT CCC AGG CTC CTC ATC TAT GGT GCA TCC AGC

     CDR2
  ~~~~~~~~~~~
      R   A   T   G   I   P   D   R   F   S   G   S   G   S   G   T   D   F
163 AGG GCC ACT GGC ATC CCA GAC AGG TTC AGT GGC AGT GGG TCT GGG ACA GAC TTC

                                                                      CDR3
                                                                       ~~~
      T   L   T   I   S   R   L   E   P   E   D   F   A   V   Y   Y   C   Q
217 ACT CTC ACC ATC AGC AGA CTG GAG CCT GAA GAT TTT GCA GTG TAT TAC TGT CAG

          CDR3
  ~~~~~~~~~~~~~~~~~~~~~~~~~~~
      Q   Y   G   S   S   P   T   F   G   G   G   T   K   V   E   I   K
271 CAG TAT GGT AGC TCA CCC ACT TTC GGC GGA GGG ACC AAG GTG GAG ATC AAA
```

>Glypican-3 4A6, VK-NT with leader
ATGGAAACCCCAGCGCAGCTTCTCTTCCTCCTGCTACTCTGGCTCCCAGATAC
CACCGGAGAAATTGTGTTGACGCAGTCTCCAGGCACCCTGTCTTTGTCTCCAG
GGGAAAGAGCCACCCTCTCCTGCAGGGCCGTTCAGAGTGTTAGCAGCAGCTA
TTTAGCCTGGTACCAGCAGAAACCTGGCCAGGCTCCCAGGCTCCTCATCTATG
GTGCATCCAGCAGGGCCACTGGCATCCCAGACAGGTTCAGTGGCAGTGGGTC
TGGGACAGACTTCACTCTCACCATCAGCAGACTGGAGCCTGAAGATTTTGCA
GTGTATTACTGTCAGCAGTATGGTAGCTCACCCACTTTCGGCGGAGGGACCA
AGGTGGAGATCAAA >Glypican-3 4A6, VK-AA with leader
METPAQLLFLLLLWLPDTTGEIVLTQSPGTLSLSPGERATLSCRAVQSVSSSYLA
WYQQKPGQAPRLLIYGASSRATGIPDRFSGSGSGTDFTLTISRLEPEDFAVYYCQQ
YGSSPTFGGGTKVEIK

Figure 2A: Anti-Glypican-3 11E7 $V_H$

```
V segment:    5-51
J segment:    JH4b

      E   V   Q   L   V   Q   S   G   A   E   V   K   K   P   G   E   S   L
  1 GAG GTG CAG CTG GTG CAG TCT GGA GCA GAG GTG AAA AAG CCC GGG GAG TCT CTG

                                                            CDR 1
                                                  ~~~~~~~~~~~~~~~~~~~
      K   I   S   C   K   G   S   G   Y   S   F   T   N   Y   W   I   A   W
 55 AAG ATC TCC TGT AAG GGT TCT GGA TAC AGC TTT ACC AAC TAC TGG ATC GCC TGG

                                                                CDR 2
                                                      ~~~~~~~~~~~~~~~~~~~
      V   R   Q   M   P   G   K   G   L   E   W   M   G   I   I   Y   P   G
109 GTG CGC CAG ATG CCC GGG AAA GGC CTG GAG TGG ATG GGG ATC ATC TAT CCT GGT

                      CDR 2
    ~~~~~~~~~~~~~~~~~~~~~~~~~~~~~~~~~~~~~~~~~~~~~~
      D   S   D   T   R   Y   S   P   S   F   Q   G   Q   V   T   I   S   A
163 GAC TCT GAT ACC AGA TAC AGC CCG TCC TTC CAA GGC CAG GTC ACC ATC TCA GCC

      D   K   S   I   R   T   A   Y   L   Q   W   S   S   L   K   A   S   D
217 GAC AAG TCC ATC AGA ACC GCC TAC CTG CAG TGG AGC AGC CTG AAG GCC TCG GAC

                                                  CDR 3
                                      ~~~~~~~~~~~~~~~~~~~~~~~~~~~~~~
      T   A   M   Y   Y   C   A   R   T   R   E   G   Y   F   D   Y   W   G
271 ACC GCC ATG TAT TAC TGT GCG AGA ACC CGG GAG GGG TAC TTT GAC TAC TGG GGC

      Q   G   T   L   V   T   V   S   S
325 CAG GGA ACC CTG GTC ACC GTC TCC TCA
```

> Glypican-3 11E7, VH-NT with leader
ATGGGGTCAACCGCCATCCTCGCCCTCCTCCTGGCTGTTCTCCAAGGAGT
CTGTGCCGAGGTGCAGCTGGTGCAGTCTGGAGCAGAGGTGAAAAAGCCCG
GGGAGTCTCTGAAGATCTCCTGTAAGGGTTCTGGATACAGCTTTACCAAC
TACTGGATCGCCTGGGTGCGCCAGATGCCCGGGAAAGGCCTGGAGTGGAT
GGGGATCATCTATCCTGGTGACTCTGATACCAGATACAGCCCGTCCTTCC
AAGGCCAGGTCACCATCTCAGCCGACAAGTCCATCAGAACCGCCTACCTG
CAGTGGAGCAGCCTGAAGGCCTCGGACACCGCCATGTATTACTGTGCGAG
AACCCGGGAGGGGTACTTTGACTACTGGGGCCAGGGAACCCTGGTCACCG
TCTCCTCA >Glypican-3 11E7, VH-AA with leader
MGSTAILALLLAVLQGVCAEVQLVQSGAEVKKPGESLKISCKGSGYSFTNYWIA
WVRQMPGKGLEWMGIIYPGDSDTRYSPSFQGQVTISADKSIRTAYLQWSSLKAS
DTAMYYCARTREGYFDYWGQGTLVTVSS

Figure 2B: Anti-Glypican-3 11E7 $V_K$

```
V segment:     A27
J segment:     JK4


     E   I   V   L   T   Q   S   P   G   T   L   S   L   S   P   G   E   R
  1 GAA ATT GTG TTG ACG CAG TCT CCA GGC ACC CTG TCT TTG TCT CCA GGG GAA AGA

                                             CDR 1
                             ~~~~~~~~~~~~~~~~~~~~~~~~~~~~~~~~~~~~~~~~~~~~~~
     A   T   L   S   C   R   A   S   Q   S   V   S   S   S   Y   L   A   W
 55 GCC ACC CTC TCC TGC AGG GCC AGT CAG AGT GTT AGC AGC AGC TAC TTA GCC TGG

                                                               CDR 2
                                                             ~~~~~~~~~~~~~~~
     Y   Q   Q   K   P   G   Q   A   P   R   L   L   I   Y   G   A   S   S
109 TAC CAG CAG AAA CCT GGC CAG GCT CCC AGG CTC CTC ATC TAT GGT GCA TCC AGC

      CDR 2
    ~~~~~~~~~~~
     R   A   T   G   I   P   D   R   F   S   G   S   G   S   G   T   D   F
163 AGG GCC ACT GGC ATC CCA GAC AGG TTC AGT GGC AGT GGG TCT GGG ACA GAC TTC

                                                                        CDR
                                                                        ~~~
     T   L   T   I   S   R   L   E   P   E   D   F   A   V   Y   Y   C   Q
217 ACT CTC ACC ATC AGC AGA CTG GAG CCT GAA GAT TTT GCA GTG TAT TAC TGT CAG

          CDR 3
    ~~~~~~~~~~~~~~~~~~~~~~~~~~~
     Q   Y   G   S   S   P   T   F   G   G   G   T   K   V   E   I   K
271 CAG TAT GGT AGC TCA CCC ACT TTC GGC GGA GGG ACC AAG GTG GAG ATC AAA
```

>Glypican-3 11E7, VK-NT with leader
ATGGAAACCCCAGCGCAGCTTCTCTTCCTCCTGCTACTCTGGCTCCCAGA
TACCACCGGAGAAATTGTGTTGACGCAGTCTCCAGGCACCCTGTCTTTGT
CTCCAGGGGAAAGAGCCACCCTCTCCTGCAGGGCCAGTCAGAGTGTTAGC
AGCAGCTACTTAGCCTGGTACCAGCAGAAACCTGGCCAGGCTCCCAGGCT
CCTCATCTATGGTGCATCCAGCAGGGCCACTGGCATCCCAGACAGGTTCA
GTGGCAGTGGGTCTGGGACAGACTTCACTCTCACCATCAGCAGACTGGAG
CCTGAAGATTTTGCAGTGTATTACTGTCAGCAGTATGGTAGCTCACCCAC
TTTCGGCGGAGGGACCAAGGTGGAGATCAAA > Glypican-3 11E7, VK-AA with leader
METPAQLLFLLLLWLPDTTGEIVLTQSPGTLSLSPGERATLSCRASQSVSSSYLAW
YQQKPGQAPRLLIYGASSRATGIPDRFSGSGSGTDFTLTISRLEPEDFAVYYCQQY
GSSPTFGGGTKVEIK

Figure 3A: Anti-Glypican-3 16D10 $V_H$

```
V segment:     5-51
J segment:     JH4b

      E   V   Q   L   V   Q   S   G   A   D   V   T   K   P   G   E   S   L
  1 GAG GTG CAA CTG GTG CAG TCT GGA GCA GAT GTG ACA AAG CCC GGG GAG TCT CTG

                                                   CDR1
                                              ~~~~~~~~~~~~~~~~~~~
      K   I   S   C   K   V   S   G   Y   R   F   T   N   Y   W   I   G   W
 55 AAG ATC TCC TGT AAG GTT TCT GGA TAC AGG TTT ACC AAC TAC TGG ATC GGC TGG

                                                       CDR2
                                                  ~~~~~~~~~~~~~~~~~~~
      M   R   Q   M   S   G   K   G   L   E   W   M   G   I   I   Y   P   G
109 ATG CGC CAG ATG TCC GGG AAA GGC CTG GAA TGG ATG GGC ATC ATC TAT CCT GGT

                  CDR2
    ~~~~~~~~~~~~~~~~~~~~~~~~~~~~~~~~~~~~~~~~~~~~~~
      D   S   D   T   R   Y   S   P   S   F   Q   G   H   V   T   I   S   A
163 GAC TCT GAT ACC AGA TAC AGT CCG TCC TTC CAA GGC CAC GTC ACC ATC TCA GCC

      D   K   S   I   N   T   A   Y   L   R   W   S   S   L   K   A   S   D
217 GAC AAA TCC ATC AAC ACC GCC TAC CTA CGG TGG AGC AGC CTG AAG GCC TCG GAC

                                              CDR3
                                  ~~~~~~~~~~~~~~~~~~~~~~~~~~~~~~
      T   A   I   Y   Y   C   A   R   T   R   E   G   F   F   D   Y   W   G
271 ACC GCC ATT TAT TAC TGT GCG CGA ACC CGG GAG GGG TTC TTT GAC TAC TGG GGC

      Q   G   T   P   V   T   V   S   S
325 CAG GGA ACC CCG GTC ACC GTC TCC TCA
```

>Glypican-3 16D10, VH-NT with leader
ATGGGGTCAACCGCCATCCTCGCCCTCCTCCTGGCTATTCTCCGAGGAGTCTG
TGCCGAGGTGCAACTGGTGCAGTCTGGAGCAGATGTGACAAAGCCCGGGGA
GTCTCTGAAGATCTCCTGTAAGGTTTCTGGATACAGGTTTACCAACTACTGGA
TCGGCTGGATGCGCCAGATGTCCGGGAAAGGCCTGGAATGGATGGGCATCAT
CTATCCTGGTGACTCTGATACCAGATACAGTCCGTCCTTCCAAGGCCACGTCA
CCATCTCAGCCGACAAATCCATCAACACCGCCTACCTACGGTGGAGCAGCCT
GAAGGCCTCGGACACCGCCATTTATTACTGTGCGCGAACCCGGGAGGGGTTC
TTTGACTACTGGGGCCAGGGAACCCCGGTCACCGTCTCCTCA > Glypican-3 16D10, VH-AA with leader
MGSTAILALLLAILRGVCAEVQLVQSGADVTKPGESLKISCKVSGYRFTNYWIG
WMRQMSGKGLEWMGIIYPGDSDTRYSPSFQGHVTISADKSINTAYLRWSSLKAS
DTAIYYCARTREGFFDYWGQGTPVTVSS

Figure 3B: Anti-Glypican-3 16D10 $V_K$

```
V segment:      A27
J segment:      JK1

     E   I   L   L   T   Q   S   P   G   T   L   S   L   S   P   G   E   R
  1 GAA ATT CTG TTG ACG CAG TCT CCA GGC ACC CTG TCT TTG TCT CCA GGG GAA AGA

                                          CDR1
                        ~~~~~~~~~~~~~~~~~~~~~~~~~~~~~~~~~~~~~~~~~~~~~~~~~~~
     A   T   L   S   C   R   A   S   Q   S   V   S   S   S   Y   L   A   W
 55 GCC ACC CTC TCC TGC AGG GCC AGT CAG AGT GTT AGC AGC AGC TAC TTA GCC TGG

                                                                  CDR2
                                                             ~~~~~~~~~~~~~~
     Y   Q   Q   K   P   G   Q   A   P   R   L   L   I   Y   G   A   S   S
109 TAC CAG CAG AAA CCT GGC CAG GCT CCC AGG CTC CTC ATC TAT GGT GCA TCC AGC

      CDR2
    ~~~~~~~~~~~
     R   A   T   G   I   P   D   R   F   S   G   S   G   S   G   T   D   F
163 AGG GCC ACT GGC ATC CCA GAC AGG TTC AGT GGC AGT GGG TCT GGG ACA GAC TTC

                                                                        CDR3
                                                                         ~~~
     T   L   T   I   S   R   L   E   P   E   D   F   A   V   Y   Y   C   Q
217 ACT CTC ACC ATC AGC AGA CTG GAG CCT GAA GAT TTT GCA GTG TAT TAC TGT CAG

            CDR3
    ~~~~~~~~~~~~~~~~~~~~~~~~~~~~
     Q   Y   G   S   S   P   T   F   G   Q   G   T   K   V   E   I   K
271 CAG TAT GGT AGC TCA CCG ACG TTC GGC CAA GGG ACC AAG GTG GAA ATC AAA
```

>Glypican-3 16D10, VK-NT with leader
ATGGAAACCCCAGCGCAGCTTCTCTTCCTCCTGCTACTCTGGCTCCCAGATAC
CACCGGAGAAATTCTGTTGACGCAGTCTCCAGGCACCCTGTCTTTGTCTCCAG
GGGAAAGAGCCACCCTCTCCTGCAGGGCCAGTCAGAGTGTTAGCAGCAGCTA
CTTAGCCTGGTACCAGCAGAAACCTGGCCAGGCTCCCAGGCTCCTCATCTAT
GGTGCATCCAGCAGGGCCACTGGCATCCCAGACAGGTTCAGTGGCAGTGGGT
CTGGGACAGACTTCACTCTCACCATCAGCAGACTGGAGCCTGAAGATTTTGC
AGTGTATTACTGTCAGCAGTATGGTAGCTCACCGACGTTCGGCCAAGGGACC
AAGGTGGAAATCAAA >Glypican-3 16D10, VK-AA with leader
METPAQLLFLLLLWLPDTTGEILLTQSPGTLSLSPGERATLSCRASQSVSSSYLAW
YQQKPGQAPRLLIYGASSRATGIPDRFSGSGSGTDFTLTISRLEPEDFAVYYCQQY
GSSPTFGQGTKVEIK Figure 4: Anti-Glypican-3 4A6 $V_H$

```
                                                                    CDR1
5-51 germline   E V Q L V Q S G A E V K K P G E S L K I S C K G S G Y S F T S Y W I G W
4A6  VH         - - - - - - - - - - - - - - - - - - - - - - - - - - - - - - - - - A -

                              CDR2
5-51 germline   V R Q M P G K G L E W M G I I Y P G D S D T R Y S P S F Q G Q V T I S A
4A6  VH         - - - - - - - - - - - - - - - F - - - - - - - - - - - - - - - - - - - -

                                                              CDR3
5-51 germline   D K S I S T A Y L Q W S S L K A S D T A M Y Y C A R
JH4b germline                                                           Y F D Y W G
4A6  VH         - R - - R - - - - - - - - - - - - - - L - - - - - - T R E G - - - - - -

JH4b germline   Q G T L V T V S S
4A6  VH         - - - - - - - - -  (JH4b)
```

Figure 5: Anti-Glypican-3 11E7 $V_H$

```
                                                                    CDR1
5-51 germline    E V Q L V Q S G A E V K K P G E S L K I S C K G S G Y S F T S Y W I G W
11E7 VH          - - - - - - - - - - - - - - - - - - - - - - - - - - - - - - N - - - A -

                                          CDR2
5-51 germline    V R Q M P G K G L E W M G I I Y P G D S D T R Y S P S F Q G Q V T I S A
11E7 VH          - - - - - - - - - - - - - - - - - - - - - - - - - - - - - - - - - - - -

                                                                 CDR3
5-51 germline    D K S I S T A Y L Q W S S L K A S D T A M Y Y C A R
JH4b germline                                                                Y F D Y W G
11E7 VH          - - - - R - - - - - - - - - - - - - - - - - - - - - T R E G - - - - - -

JH4b germline    Q G T L V T V S S
11E7 VH          - - - - - - - - -
```

Figure 6: Anti-Glypican-3 16D10 $V_H$

```
5-51 germline      E V Q L V Q S G A E V K K P G E S L K
16D10 VH           - - - - - - - - - D - T - - - - - - -

                                       _CDR1_____
5-51 germline      I S C K G S G Y S F T S Y W I G W V R
16D10 VH           - - - - V - - - R - - N - - - - - M -

                                       _CDR2___________
5-51 germline      Q M P G K G L E W M G I I Y P G D S D
16D10 VH           - - S - - - - - - - - - - - - - - - -

                   _________________
5-51 germline      T R Y S P S F Q G Q V T I S A D K S I
16D10 VH           - - - - - - - - - H - - - - - - - - -

5-51 germline      S T A Y L Q W S S L K A S D T A M Y Y
16D10 VH           N - - - - R - - - - - - - - - - I - -

                         _CDR3__________
5-51 germline      C A R
JH4b germline                        F D Y W G Q G T L V T
16D10 VH           - - - T R E G F - - - - - - - - P - -

JH4b germline      V S S
16D10 VH           - - -
```

Figure 7: Anti-Glypican-3 4A6 $V_K$

```
A27 germline         E I V L T Q S P G T L S L S P G E R
4A6 VK               - - - - - - - - - - - - - - - - - -

                               _CDR1________________
A27 germline         A T L S C R A S Q S V S S S Y L A W
4A6 VK               - - - - - - - V - - - - - - - - - -

                                                _CDR2__
A27 germline         Y Q Q K P G Q A P R L L I Y G A S S
4A6 VK               - - - - - - - - - - - - - - - - - -

                     CDR2_
A27 germline         R A T G I P D R F S G S G S G T D F
4A6 VK               - - - - - - - - - - - - - - - - - -

A27 germline         T L T I S R L E P E D F A V Y Y C Q
4A6 VK               - - - - - - - - - - - - - - - - - -

                     CDR3_________
A27 germline         Q Y G S S P
JK4 germline                     T F G G G T K V E I K
4A6 VK               - - - - - - - - - - - - - - - - - (JK4)
```

Figure 8: Anti-Glypican-3 11E7 $V_K$

```
A27   germline        E I V L T Q S P G T L S L S P G E R
11E7 VK               - - - - - - - - - - - - - - - - - -

                                _CDR1__________________
A27   germline        A T L S C R A S Q S V S S S Y L A W
11E7 VK               - - - - - - - - - - - - - - - - - -

                                                _CDR_2_
A27   germline        Y Q Q K P G Q A P R L L I Y G A S S
11E7 VK               - - - - - - - - - - - - - - - - - -

                      CDR_2
A27   germline        R A T G I P D R F S G S G S G T D F
11E7 VK               - - - - - - - - - - - - - - - - - -

A27   germline        T L T I S R L E P E D F A V Y Y C Q
11E7 VK               - - - - - - - - - - - - - - - - - -

                      CDR3________
A27   germline        Q Y G S S P
JK4   germline                    T F G G G T K V E I K
11E7 VK               - - - - - - - - - - - - - - - - -
```

Figure 9: Anti-Glypican-3 16D10 $V_K$

```
A27 germline    E I V L T Q S P G T L S L S P G E R
16D10 VK        - - L - - - - - - - - - - - - - - -

                          CDR1
A27 germline    A T L S C R A S Q S V S S S Y L A W
16D10 VK        - - - - - - - - - - - - - - - - - -

                                            CDR2
A27 germline    Y Q Q K P G Q A P R L L I Y G A S S
16D10 VK        - - - - - - - - - - - - - - - - - -

A27 germline    R A T G I P D R F S G S G S G T D F
16D10 VK        - - - - - - - - - - - - - - - - - -

A27 germline    T L T I S R L E P E D F A V Y Y C Q
16D10 VK        - - - - - - - - - - - - - - - - - -

                CDR3
A27 germline    Q Y G S S P
JK1 germline                T F G Q G T K V E I K
16D10 VK        - - - - - - - - - - - - - - - - -
```

Figure 10: FACS titration (EC50)
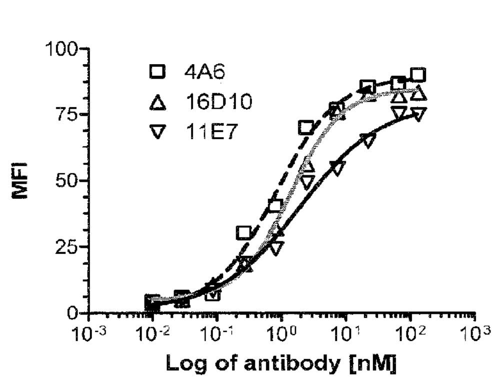
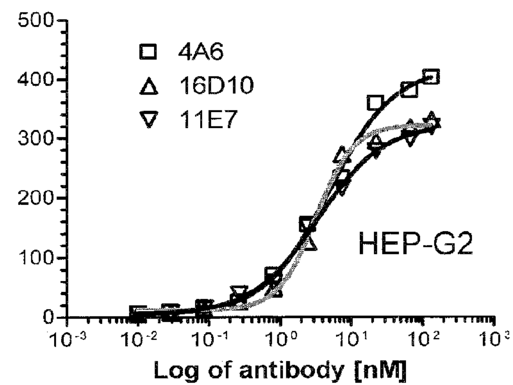

Figure 11: FACS analysis shows specific binding to HCC cells
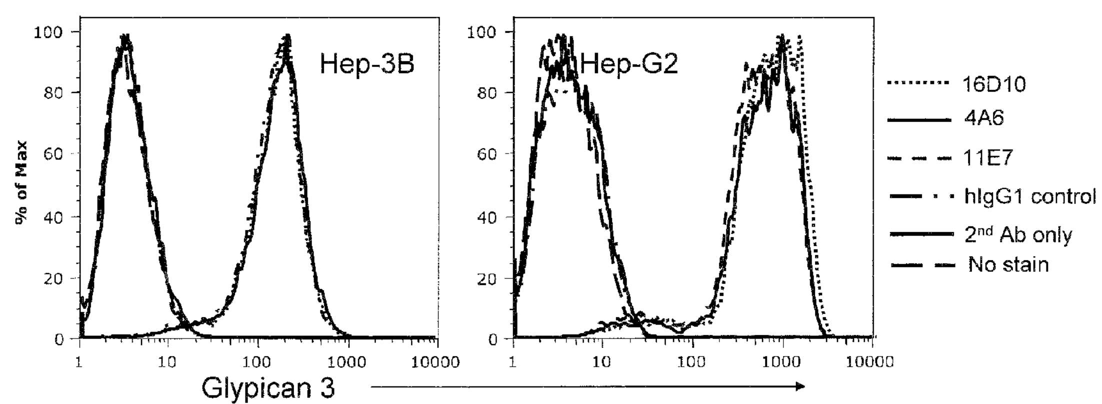

Figure 12: FACS analysis shows specific antibody binding to Glypican 3
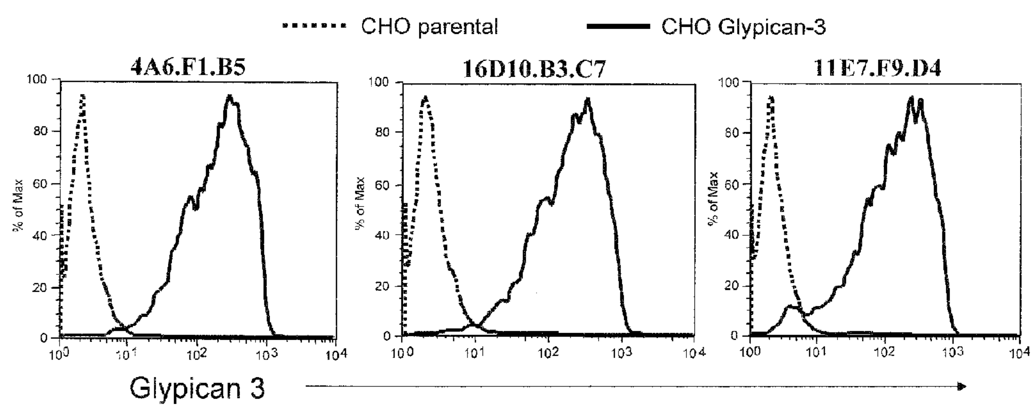

Figure 13: 4A6 Antibodies binding to liver cancer tissues
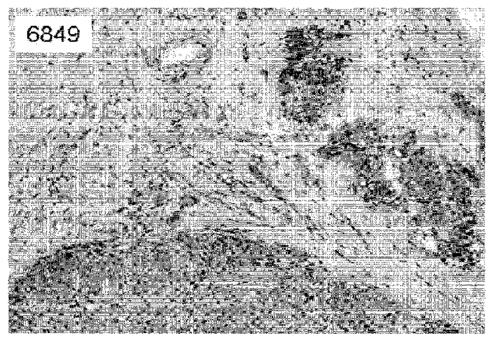
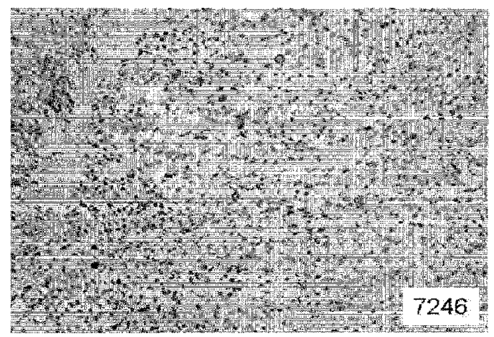

Figure 14: Antibody-dependent cellular cytotoxicity
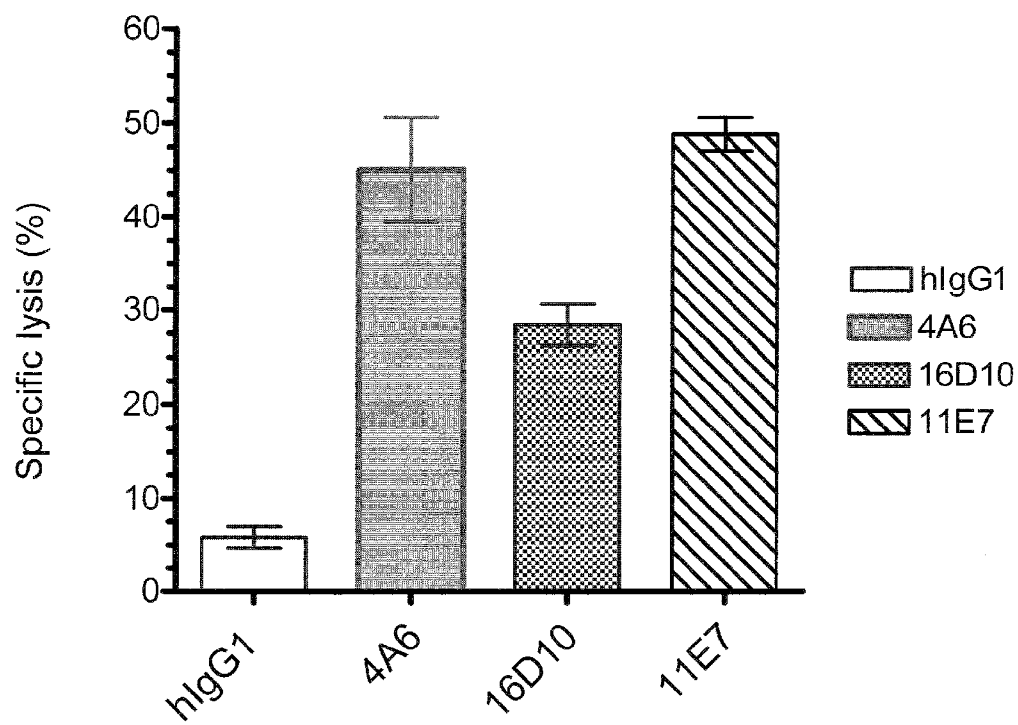

Figure 15: HumZap internalization assay
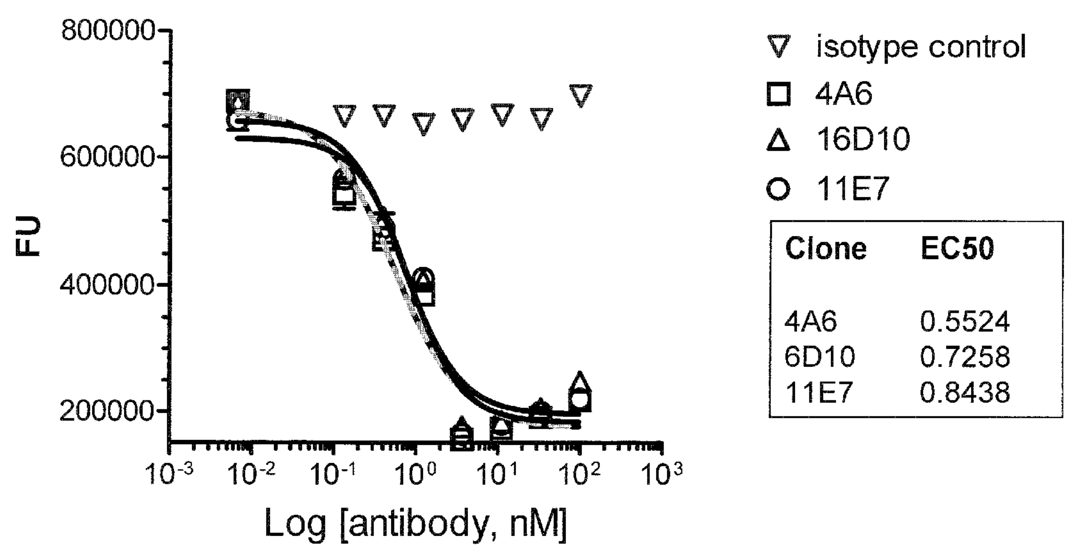

Figure 16: Immunofluorescence shows antibody Internalization
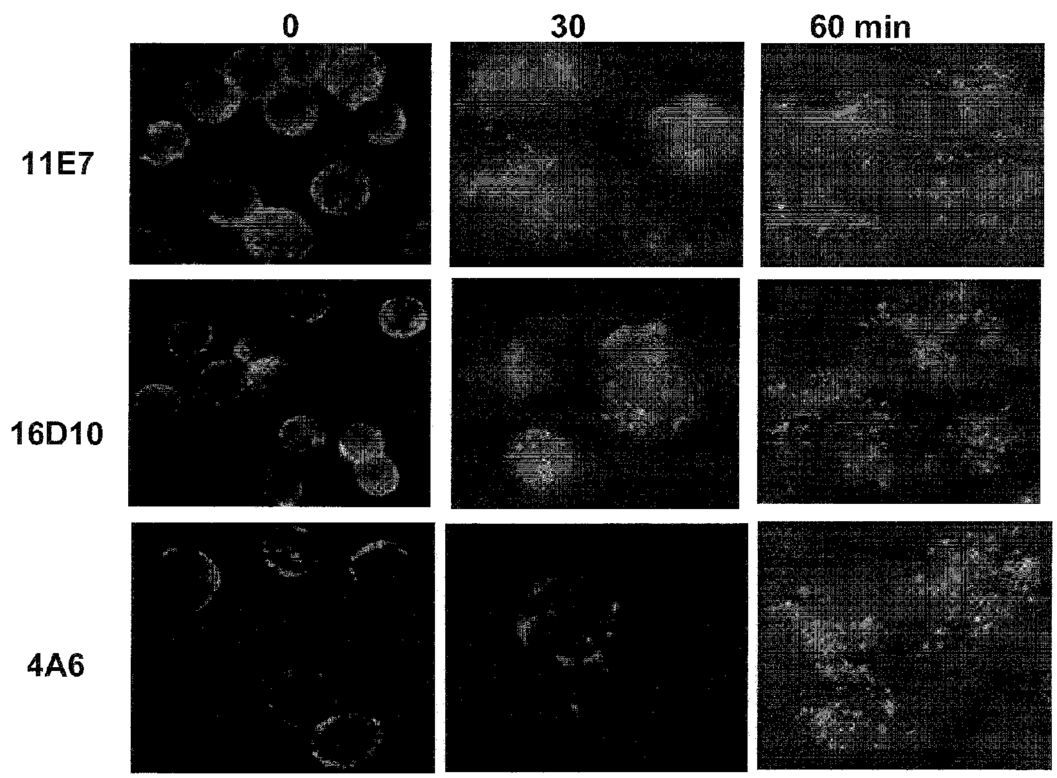

SEQUENCE LISTING

```
<160> NUMBER OF SEQ ID NOS: 48

<210> SEQ ID NO 1
<211> LENGTH: 5
<212> TYPE: PRT
<213> ORGANISM: Homo sapiens

<400> SEQUENCE: 1

Ser Tyr Trp Ile Ala
1               5


<210> SEQ ID NO 2
<211> LENGTH: 5
<212> TYPE: PRT
<213> ORGANISM: Homo sapiens

<400> SEQUENCE: 2

Asn Tyr Trp Ile Ala
1               5


<210> SEQ ID NO 3
<211> LENGTH: 5
<212> TYPE: PRT
<213> ORGANISM: Homo sapiens

<400> SEQUENCE: 3

Asn Tyr Trp Ile Gly
1               5


<210> SEQ ID NO 4
<211> LENGTH: 17
<212> TYPE: PRT
<213> ORGANISM: Homo sapiens

<400> SEQUENCE: 4

Ile Ile Phe Pro Gly Asp Ser Asp Thr Arg Tyr Ser Pro Ser Phe Gln
1               5                   10                  15

Gly


<210> SEQ ID NO 5
<211> LENGTH: 17
<212> TYPE: PRT
<213> ORGANISM: Homo sapiens

<400> SEQUENCE: 5

Ile Ile Tyr Pro Gly Asp Ser Asp Thr Arg Tyr Ser Pro Ser Phe Gln
1               5                   10                  15
```

Gly

<210> SEQ ID NO 6
<211> LENGTH: 17
<212> TYPE: PRT
<213> ORGANISM: Homo sapiens

<400> SEQUENCE: 6

Ile Ile Tyr Pro Gly Asp Ser Asp Thr Arg Tyr Ser Pro Ser Phe Gln
1 5 10 15

Gly

<210> SEQ ID NO 7
<211> LENGTH: 8
<212> TYPE: PRT
<213> ORGANISM: Homo sapiens

<400> SEQUENCE: 7

Thr Arg Glu Gly Tyr Phe Asp Tyr
1 5

<210> SEQ ID NO 8
<211> LENGTH: 8
<212> TYPE: PRT
<213> ORGANISM: Homo sapiens

<400> SEQUENCE: 8

Thr Arg Glu Gly Tyr Phe Asp Tyr
1 5

<210> SEQ ID NO 9
<211> LENGTH: 8
<212> TYPE: PRT
<213> ORGANISM: Homo sapiens

<400> SEQUENCE: 9

Thr Arg Glu Gly Phe Phe Asp Tyr
1 5

<210> SEQ ID NO 10
<211> LENGTH: 12
<212> TYPE: PRT
<213> ORGANISM: Homo sapiens

<400> SEQUENCE: 10

Arg Ala Val Gln Ser Val Ser Ser Ser Tyr Leu Ala
1 5 10

<210> SEQ ID NO 11
<211> LENGTH: 12
<212> TYPE: PRT
<213> ORGANISM: Homo sapiens

<400> SEQUENCE: 11

Arg Ala Ser Gln Ser Val Ser Ser Ser Tyr Leu Ala
1 5 10

<210> SEQ ID NO 12
<211> LENGTH: 12
<212> TYPE: PRT
<213> ORGANISM: Homo sapiens

<400> SEQUENCE: 12

Arg Ala Ser Gln Ser Val Ser Ser Ser Tyr Leu Ala
1 5 10

<210> SEQ ID NO 13
<211> LENGTH: 7
<212> TYPE: PRT
<213> ORGANISM: Homo sapiens

<400> SEQUENCE: 13

Gly Ala Ser Ser Arg Ala Thr
1 5

<210> SEQ ID NO 14
<211> LENGTH: 7
<212> TYPE: PRT
<213> ORGANISM: Homo sapiens

<400> SEQUENCE: 14

Gly Ala Ser Ser Arg Ala Thr
1 5

<210> SEQ ID NO 15
<211> LENGTH: 7
<212> TYPE: PRT
<213> ORGANISM: Homo sapiens

<400> SEQUENCE: 15

Gly Ala Ser Ser Arg Ala Thr
1 5

<210> SEQ ID NO 16
<211> LENGTH: 8
<212> TYPE: PRT
<213> ORGANISM: Homo sapiens

<400> SEQUENCE: 16

Gln Gln Tyr Gly Ser Ser Pro Thr
1 5

<210> SEQ ID NO 17
<211> LENGTH: 8
<212> TYPE: PRT
<213> ORGANISM: Homo sapiens

<400> SEQUENCE: 17

Gln Gln Tyr Gly Ser Ser Pro Thr
1 5

<210> SEQ ID NO 18
<211> LENGTH: 8
<212> TYPE: PRT
<213> ORGANISM: Homo sapiens

<400> SEQUENCE: 18

Gln Gln Tyr Gly Ser Ser Pro Thr
1 5

<210> SEQ ID NO 19
<211> LENGTH: 117
<212> TYPE: PRT
<213> ORGANISM: Homo sapiens

<400> SEQUENCE: 19

Glu Val Gln Leu Val Gln Ser Gly Ala Glu Val Lys Lys Pro Gly Glu
1 5 10 15

Ser Leu Lys Ile Ser Cys Lys Gly Ser Gly Tyr Ser Phe Thr Ser Tyr
20 25 30

```
Trp Ile Ala Trp Val Arg Gln Met Pro Gly Lys Gly Leu Glu Trp Met
        35                  40                  45

Gly Ile Ile Phe Pro Gly Asp Ser Asp Thr Arg Tyr Ser Pro Ser Phe
    50                  55                  60

Gln Gly Gln Val Thr Ile Ser Ala Asp Arg Ser Ile Arg Thr Ala Tyr
65                  70                  75                  80

Leu Gln Trp Ser Ser Leu Lys Ala Ser Asp Thr Ala Leu Tyr Tyr Cys
                85                  90                  95

Ala Arg Thr Arg Glu Gly Tyr Phe Asp Tyr Trp Gly Gln Gly Thr Leu
            100                 105                 110

Val Thr Val Ser Ser
        115


<210> SEQ ID NO 20
<211> LENGTH: 117
<212> TYPE: PRT
<213> ORGANISM: Homo sapiens

<400> SEQUENCE: 20

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Ala Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Arg Thr Ala Tyr
65                  70                  75                  80

Leu Gln Trp Ser Ser Leu Lys Ala Ser Asp Thr Ala Met Tyr Tyr Cys
                85                  90                  95

Ala Arg Thr Arg Glu Gly Tyr Phe Asp Tyr Trp Gly Gln Gly Thr Leu
            100                 105                 110

Val Thr Val Ser Ser
        115


<210> SEQ ID NO 21
<211> LENGTH: 117
<212> TYPE: PRT
<213> ORGANISM: Homo sapiens

<400> SEQUENCE: 21

Glu Val Gln Leu Val Gln Ser Gly Ala Asp Val Thr Lys Pro Gly Glu
1               5                   10                  15

Ser Leu Lys Ile Ser Cys Lys Val Ser Gly Tyr Arg Phe Thr Asn Tyr
            20                  25                  30

Trp Ile Gly Trp Met Arg Gln Met Ser Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly His Val Thr Ile Ser Ala Asp Lys Ser Ile Asn Thr Ala Tyr
65                  70                  75                  80

Leu Arg Trp Ser Ser Leu Lys Ala Ser Asp Thr Ala Ile Tyr Tyr Cys
                85                  90                  95

Ala Arg Thr Arg Glu Gly Phe Phe Asp Tyr Trp Gly Gln Gly Thr Pro
            100                 105                 110
```

```
Val Thr Val Ser Ser
        115


<210> SEQ ID NO 22
<211> LENGTH: 107
<212> TYPE: PRT
<213> ORGANISM: Homo sapiens

<400> SEQUENCE: 22

Glu Ile Val Leu Thr Gln Ser Pro Gly Thr Leu Ser Leu Ser Pro Gly
1               5                   10                  15

Glu Arg Ala Thr Leu Ser Cys Arg Ala Val Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Thr Phe Gly Gly Gly Thr Lys Val Glu Ile Lys
            100                 105


<210> SEQ ID NO 23
<211> LENGTH: 107
<212> TYPE: PRT
<213> ORGANISM: Homo sapiens

<400> SEQUENCE: 23

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Thr Phe Gly Gly Gly Thr Lys Val Glu Ile Lys
            100                 105


<210> SEQ ID NO 24
<211> LENGTH: 107
<212> TYPE: PRT
<213> ORGANISM: Homo sapiens

<400> SEQUENCE: 24

Glu Ile Leu Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60
```

```
Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Thr Phe Gly Gln Gly Thr Lys Val Glu Ile Lys
            100                 105


<210> SEQ ID NO 25
<211> LENGTH: 351
<212> TYPE: DNA
<213> ORGANISM: Homo sapiens

<400> SEQUENCE: 25

gaggtgcagc tggtgcagtc tggagcagag gtgaaaaagc ccggggagtc tctgaagatc     60

tcctgtaagg gttctggata cagctttacc agctactgga tcgcctgggt gcgccagatg    120

cccgggaaag gcctggagtg gatggggatc atctttcctg gtgactctga taccagatac    180

agcccgtcct tccaaggcca ggtcaccatc tcagccgaca ggtccatcag aaccgcctac    240

ctgcagtgga gcagcctgaa ggcctcggac accgccttgt attactgtgc gagaacccgg    300

gaggggtact ttgactactg gggccaggga accctggtca ccgtctcctc a             351


<210> SEQ ID NO 26
<211> LENGTH: 351
<212> TYPE: DNA
<213> ORGANISM: Homo sapiens

<400> SEQUENCE: 26

gaggtgcagc tggtgcagtc tggagcagag gtgaaaaagc ccggggagtc tctgaagatc     60

tcctgtaagg gttctggata cagctttacc aactactgga tcgcctgggt gcgccagatg    120

cccgggaaag gcctggagtg gatggggatc atctatcctg gtgactctga taccagatac    180

agcccgtcct tccaaggcca ggtcaccatc tcagccgaca agtccatcag aaccgcctac    240

ctgcagtgga gcagcctgaa ggcctcggac accgccatgt attactgtgc gagaacccgg    300

gaggggtact ttgactactg gggccaggga accctggtca ccgtctcctc a             351


<210> SEQ ID NO 27
<211> LENGTH: 351
<212> TYPE: DNA
<213> ORGANISM: Homo sapiens

<400> SEQUENCE: 27

gaggtgcaac tggtgcagtc tggagcagat gtgacaaagc ccggggagtc tctgaagatc     60

tcctgtaagg tttctggata caggtttacc aactactgga tcggctggat gcgccagatg    120

tccgggaaag gcctggaatg gatgggcatc atctatcctg gtgactctga taccagatac    180

agtccgtcct tccaaggcca cgtcaccatc tcagccgaca aatccatcaa caccgcctac    240

ctacggtgga gcagcctgaa ggcctcggac accgccattt attactgtgc gcgaacccgg    300

gaggggttct ttgactactg gggccaggga accccggtca ccgtctcctc a             351


<210> SEQ ID NO 28
<211> LENGTH: 321
<212> TYPE: DNA
<213> ORGANISM: Homo sapiens

<400> SEQUENCE: 28

gaaattgtgt tgacgcagtc tccaggcacc ctgtctttgt ctccagggga aagagccacc     60
```

```
ctctcctgca gggccgttca gagtgttagc agcagctatt tagcctggta ccagcagaaa    120

cctggccagg ctcccaggct cctcatctat ggtgcatcca gcagggccac tggcatccca    180

gacaggttca gtggcagtgg gtctgggaca gacttcactc tcaccatcag cagactggag    240

cctgaagatt ttgcagtgta ttactgtcag cagtatggta gctcacccac tttcggcgga    300

gggaccaagg tggagatcaa a                                                321
```

<210> SEQ ID NO 29
<211> LENGTH: 321
<212> TYPE: DNA
<213> ORGANISM: Homo sapiens

<400> SEQUENCE: 29

```
gaaattgtgt tgacgcagtc tccaggcacc ctgtctttgt ctccagggga aagagccacc     60

ctctcctgca gggccagtca gagtgttagc agcagctact tagcctggta ccagcagaaa    120

cctggccagg ctcccaggct cctcatctat ggtgcatcca gcagggccac tggcatccca    180

gacaggttca gtggcagtgg gtctgggaca gacttcactc tcaccatcag cagactggag    240

cctgaagatt ttgcagtgta ttactgtcag cagtatggta gctcacccac tttcggcgga    300

gggaccaagg tggagatcaa a                                                321
```

<210> SEQ ID NO 30
<211> LENGTH: 321
<212> TYPE: DNA
<213> ORGANISM: Homo sapiens

<400> SEQUENCE: 30

```
gaaattctgt tgacgcagtc tccaggcacc ctgtctttgt ctccagggga aagagccacc     60

ctctcctgca gggccagtca gagtgttagc agcagctact tagcctggta ccagcagaaa    120

cctggccagg ctcccaggct cctcatctat ggtgcatcca gcagggccac tggcatccca    180

gacaggttca gtggcagtgg gtctgggaca gacttcactc tcaccatcag cagactggag    240

cctgaagatt ttgcagtgta ttactgtcag cagtatggta gctcaccgac gttcggccaa    300

gggaccaagg tggaaatcaa a                                                321
```

<210> SEQ ID NO 31
<211> LENGTH: 98
<212> TYPE: PRT
<213> ORGANISM: Homo sapiens

<400> SEQUENCE: 31

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg
```

<210> SEQ ID NO 32

```
<211> LENGTH: 15
<212> TYPE: PRT
<213> ORGANISM: Homo sapiens

<400> SEQUENCE: 32

Tyr Phe Asp Tyr Trp Gly Gln Gly Thr Leu Val Thr Val Ser Ser
1               5                   10                  15


<210> SEQ ID NO 33
<211> LENGTH: 96
<212> TYPE: PRT
<213> ORGANISM: Homo sapiens

<400> SEQUENCE: 33

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95


<210> SEQ ID NO 34
<211> LENGTH: 11
<212> TYPE: PRT
<213> ORGANISM: Homo sapiens

<400> SEQUENCE: 34

Thr Phe Gly Gly Gly Thr Lys Val Glu Ile Lys
1               5                   10


<210> SEQ ID NO 35
<211> LENGTH: 11
<212> TYPE: PRT
<213> ORGANISM: Homo sapiens

<400> SEQUENCE: 35

Thr Phe Gly Gln Gly Thr Lys Val Glu Ile Lys
1               5                   10


<210> SEQ ID NO 36
<211> LENGTH: 580
<212> TYPE: PRT
<213> ORGANISM: Homo sapiens

<400> SEQUENCE: 36

Met Ala Gly Thr Val Arg Thr Ala Cys Leu Val Val Ala Met Leu Leu
1               5                   10                  15

Ser Leu Asp Phe Pro Gly Gln Ala Gln Pro Pro Pro Pro Pro Pro Asp
            20                  25                  30

Ala Thr Cys His Gln Val Arg Ser Phe Phe Gln Arg Leu Gln Pro Gly
        35                  40                  45

Leu Lys Trp Val Pro Glu Thr Pro Val Pro Gly Ser Asp Leu Gln Val
    50                  55                  60

Cys Leu Pro Lys Gly Pro Thr Cys Cys Ser Arg Lys Met Glu Glu Lys
65                  70                  75                  80
```

```
Tyr Gln Leu Thr Ala Arg Leu Asn Met Glu Gln Leu Leu Gln Ser Ala
                85                  90                  95

Ser Met Glu Leu Lys Phe Leu Ile Ile Gln Asn Ala Ala Val Phe Gln
            100                 105                 110

Glu Ala Phe Glu Ile Val Val Arg His Ala Lys Asn Tyr Thr Asn Ala
        115                 120                 125

Met Phe Lys Asn Asn Tyr Pro Ser Leu Thr Pro Gln Ala Phe Glu Phe
    130                 135                 140

Val Gly Glu Phe Phe Thr Asp Val Ser Leu Tyr Ile Leu Gly Ser Asp
145                 150                 155                 160

Ile Asn Val Asp Asp Met Val Asn Glu Leu Phe Asp Ser Leu Phe Pro
                165                 170                 175

Val Ile Tyr Thr Gln Leu Met Asn Pro Gly Leu Pro Asp Ser Ala Leu
            180                 185                 190

Asp Ile Asn Glu Cys Leu Arg Gly Ala Arg Arg Asp Leu Lys Val Phe
        195                 200                 205

Gly Asn Phe Pro Lys Leu Ile Met Thr Gln Val Ser Lys Ser Leu Gln
    210                 215                 220

Val Thr Arg Ile Phe Leu Gln Ala Leu Asn Leu Gly Ile Glu Val Ile
225                 230                 235                 240

Asn Thr Thr Asp His Leu Lys Phe Ser Lys Asp Cys Gly Arg Met Leu
                245                 250                 255

Thr Arg Met Trp Tyr Cys Ser Tyr Cys Gln Gly Leu Met Met Val Lys
            260                 265                 270

Pro Cys Gly Gly Tyr Cys Asn Val Val Met Gln Gly Cys Met Ala Gly
        275                 280                 285

Val Val Glu Ile Asp Lys Tyr Trp Arg Glu Tyr Ile Leu Ser Leu Glu
    290                 295                 300

Glu Leu Val Asn Gly Met Tyr Arg Ile Tyr Asp Met Glu Asn Val Leu
305                 310                 315                 320

Leu Gly Leu Phe Ser Thr Ile His Asp Ser Ile Gln Tyr Val Gln Lys
                325                 330                 335

Asn Ala Gly Lys Leu Thr Thr Thr Ile Gly Lys Leu Cys Ala His Ser
            340                 345                 350

Gln Gln Arg Gln Tyr Arg Ser Ala Tyr Tyr Pro Glu Asp Leu Phe Ile
        355                 360                 365

Asp Lys Lys Val Leu Lys Val Ala His Val Glu His Glu Glu Thr Leu
    370                 375                 380

Ser Ser Arg Arg Arg Glu Leu Ile Gln Lys Leu Lys Ser Phe Ile Ser
385                 390                 395                 400

Phe Tyr Ser Ala Leu Pro Gly Tyr Ile Cys Ser His Ser Pro Val Ala
                405                 410                 415

Glu Asn Asp Thr Leu Cys Trp Asn Gly Gln Glu Leu Val Glu Arg Tyr
            420                 425                 430

Ser Gln Lys Ala Ala Arg Asn Gly Met Lys Asn Gln Phe Asn Leu His
        435                 440                 445

Glu Leu Lys Met Lys Gly Pro Glu Pro Val Val Ser Gln Ile Ile Asp
    450                 455                 460

Lys Leu Lys His Ile Asn Gln Leu Leu Arg Thr Met Ser Met Pro Lys
465                 470                 475                 480

Gly Arg Val Leu Asp Lys Asn Leu Asp Glu Glu Gly Phe Glu Ser Gly
                485                 490                 495

Asp Cys Gly Asp Asp Glu Asp Glu Cys Ile Gly Gly Ser Gly Asp Gly
            500                 505                 510
```

```
Met Ile Lys Val Lys Asn Gln Leu Arg Phe Leu Ala Glu Leu Ala Tyr
        515                 520                 525

Asp Leu Asp Val Asp Asp Ala Pro Gly Asn Ser Gln Gln Ala Thr Pro
    530                 535                 540

Lys Asp Asn Glu Ile Ser Thr Phe His Asn Leu Gly Asn Val His Ser
545                 550                 555                 560

Pro Leu Lys Leu Leu Thr Ser Met Ala Ile Ser Val Val Cys Phe Phe
                565                 570                 575

Phe Leu Val His
            580


<210> SEQ ID NO 37
<211> LENGTH: 408
<212> TYPE: DNA
<213> ORGANISM: Homo sapiens

<400> SEQUENCE: 37

atggggtcaa ccgccatcct cgccctcctc ctggctgttc tccaaggagt ctgtgccgag      60

gtgcagctgg tgcagtctgg agcagaggtg aaaaagcccg gggagtctct gaagatctcc     120

tgtaagggtt ctggatacag ctttaccagc tactggatcg cctgggtgcg ccagatgccc     180

gggaaaggcc tggagtggat ggggatcatc tttcctggtg actctgatac cagatacagc     240

ccgtccttcc aaggccaggt caccatctca gccgacaggt ccatcagaac cgcctacctg     300

cagtggagca gcctgaaggc ctcggacacc gccttgtatt actgtgcgag aacccgggag     360

gggtactttg actactgggg ccagggaacc ctggtcaccg tctcctca                  408


<210> SEQ ID NO 38
<211> LENGTH: 136
<212> TYPE: PRT
<213> ORGANISM: Homo sapiens

<400> SEQUENCE: 38

Met Gly Ser Thr Ala Ile Leu Ala Leu Leu Leu Ala Val Leu Gln Gly
1               5                   10                  15

Val Cys Ala Glu Val Gln Leu Val Gln Ser Gly Ala Glu Val Lys Lys
            20                  25                  30

Pro Gly Glu Ser Leu Lys Ile Ser Cys Lys Gly Ser Gly Tyr Ser Phe
        35                  40                  45

Thr Ser Tyr Trp Ile Ala Trp Val Arg Gln Met Pro Gly Lys Gly Leu
    50                  55                  60

Glu Trp Met Gly Ile Ile Phe Pro Gly Asp Ser Asp Thr Arg Tyr Ser
65                  70                  75                  80

Pro Ser Phe Gln Gly Gln Val Thr Ile Ser Ala Asp Arg Ser Ile Arg
                85                  90                  95

Thr Ala Tyr Leu Gln Trp Ser Ser Leu Lys Ala Ser Asp Thr Ala Leu
            100                 105                 110

Tyr Tyr Cys Ala Arg Thr Arg Glu Gly Tyr Phe Asp Tyr Trp Gly Gln
        115                 120                 125

Gly Thr Leu Val Thr Val Ser Ser
    130                 135


<210> SEQ ID NO 39
<211> LENGTH: 381
<212> TYPE: DNA
<213> ORGANISM: Homo sapiens

<400> SEQUENCE: 39
```

```
atggaaaccc cagcgcagct tctcttcctc ctgctactct ggctcccaga taccaccgga     60

gaaattgtgt tgacgcagtc tccaggcacc ctgtctttgt ctccagggga aagagccacc    120

ctctcctgca gggccgttca gagtgttagc agcagctatt tagcctggta ccagcagaaa    180

cctggccagg ctcccaggct cctcatctat ggtgcatcca gcagggccac tggcatccca    240

gacaggttca gtggcagtgg gtctgggaca gacttcactc tcaccatcag cagactggag    300

cctgaagatt ttgcagtgta ttactgtcag cagtatggta gctcacccac tttcggcgga    360

gggaccaagg tggagatcaa a                                              381
```

<210> SEQ ID NO 40
<211> LENGTH: 127
<212> TYPE: PRT
<213> ORGANISM: Homo sapiens

<400> SEQUENCE: 40

```
Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Val Gln Ser
        35                  40                  45

Val Ser Ser Ser Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Ser Ser Pro Thr Phe Gly Gly Gly Thr Lys Val Glu Ile Lys
        115                 120                 125
```

<210> SEQ ID NO 41
<211> LENGTH: 408
<212> TYPE: DNA
<213> ORGANISM: Homo sapiens

<400> SEQUENCE: 41

```
atggggtcaa ccgccatcct cgccctcctc ctggctgttc tccaaggagt ctgtgccgag     60

gtgcagctgg tgcagtctgg agcagaggtg aaaaagcccg gggagtctct gaagatctcc    120

tgtaagggtt ctggatacag ctttaccaac tactggatcg cctgggtgcg ccagatgccc    180

gggaaaggcc tggagtggat ggggatcatc tatcctggtg actctgatac cagatacagc    240

ccgtccttcc aaggccaggt caccatctca gccgacaagt ccatcagaac cgcctacctg    300

cagtggagca gcctgaaggc ctcggacacc gccatgtatt actgtgcgag aacccgggag    360

gggtactttg actactgggg ccagggaacc ctggtcaccg tctcctca                 408
```

<210> SEQ ID NO 42
<211> LENGTH: 136
<212> TYPE: PRT
<213> ORGANISM: Homo sapiens

<400> SEQUENCE: 42

```
Met Gly Ser Thr Ala Ile Leu Ala Leu Leu Leu Ala Val Leu Gln Gly
1               5                   10                  15
```

```
Val Cys Ala Glu Val Gln Leu Val Gln Ser Gly Ala Glu Val Lys Lys
            20                  25                  30

Pro Gly Glu Ser Leu Lys Ile Ser Cys Lys Gly Ser Gly Tyr Ser Phe
        35                  40                  45

Thr Asn Tyr Trp Ile Ala Trp Val Arg Gln Met Pro Gly Lys Gly Leu
    50                  55                  60

Glu Trp Met Gly Ile Ile Tyr Pro Gly Asp Ser Asp Thr Arg Tyr Ser
65                  70                  75                  80

Pro Ser Phe Gln Gly Gln Val Thr Ile Ser Ala Asp Lys Ser Ile Arg
                85                  90                  95

Thr Ala Tyr Leu Gln Trp Ser Ser Leu Lys Ala Ser Asp Thr Ala Met
            100                 105                 110

Tyr Tyr Cys Ala Arg Thr Arg Glu Gly Tyr Phe Asp Tyr Trp Gly Gln
        115                 120                 125

Gly Thr Leu Val Thr Val Ser Ser
    130                 135


<210> SEQ ID NO 43
<211> LENGTH: 381
<212> TYPE: DNA
<213> ORGANISM: Homo sapiens

<400> SEQUENCE: 43

atggaaaccc cagcgcagct tctcttcctc ctgctactct ggctcccaga taccaccgga      60

gaaattgtgt tgacgcagtc tccaggcacc ctgtctttgt ctccagggga aagagccacc     120

ctctcctgca gggccagtca gagtgttagc agcagctact tagcctggta ccagcagaaa     180

cctggccagg ctcccaggct cctcatctat ggtgcatcca gcagggccac tggcatccca     240

gacaggttca gtggcagtgg gtctgggaca gacttcactc tcaccatcag cagactggag     300

cctgaagatt ttgcagtgta ttactgtcag cagtatggta gctcacccac tttcggcgga     360

gggaccaagg tggagatcaa a                                               381


<210> SEQ ID NO 44
<211> LENGTH: 127
<212> TYPE: PRT
<213> ORGANISM: Homo sapiens

<400> SEQUENCE: 44

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Ser Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Ser Ser Pro Thr Phe Gly Gly Gly Thr Lys Val Glu Ile Lys
        115                 120                 125


<210> SEQ ID NO 45
```

<211> LENGTH: 408
<212> TYPE: DNA
<213> ORGANISM: Homo sapiens

<400> SEQUENCE: 45

```
atggggtcaa ccgccatcct cgccctcctc ctggctattc tccgaggagt ctgtgccgag     60

gtgcaactgg tgcagtctgg agcagatgtg acaaagcccg gggagtctct gaagatctcc    120

tgtaaggttt ctggatacag gtttaccaac tactggatcg gctggatgcg ccagatgtcc    180

gggaaaggcc tggaatggat gggcatcatc tatcctggtg actctgatac cagatacagt    240

ccgtccttcc aaggccacgt caccatctca gccgacaaat ccatcaacac cgcctaccta    300

cggtggagca gcctgaaggc ctcggacacc gccatttatt actgtgcgcg aacccgggag    360

gggttctttg actactgggg ccagggaacc ccggtcaccg tctcctca                 408
```

<210> SEQ ID NO 46
<211> LENGTH: 136
<212> TYPE: PRT
<213> ORGANISM: Homo sapiens

<400> SEQUENCE: 46

```
Met Gly Ser Thr Ala Ile Leu Ala Leu Leu Leu Ala Ile Leu Arg Gly
1               5                   10                  15

Val Cys Ala Glu Val Gln Leu Val Gln Ser Gly Ala Asp Val Thr Lys
            20                  25                  30

Pro Gly Glu Ser Leu Lys Ile Ser Cys Lys Val Ser Gly Tyr Arg Phe
        35                  40                  45

Thr Asn Tyr Trp Ile Gly Trp Met Arg Gln Met Ser Gly Lys Gly Leu
    50                  55                  60

Glu Trp Met Gly Ile Ile Tyr Pro Gly Asp Ser Asp Thr Arg Tyr Ser
65                  70                  75                  80

Pro Ser Phe Gln Gly His Val Thr Ile Ser Ala Asp Lys Ser Ile Asn
                85                  90                  95

Thr Ala Tyr Leu Arg Trp Ser Ser Leu Lys Ala Ser Asp Thr Ala Ile
            100                 105                 110

Tyr Tyr Cys Ala Arg Thr Arg Glu Gly Phe Phe Asp Tyr Trp Gly Gln
        115                 120                 125

Gly Thr Pro Val Thr Val Ser Ser
    130                 135
```

<210> SEQ ID NO 47
<211> LENGTH: 381
<212> TYPE: DNA
<213> ORGANISM: Homo sapiens

<400> SEQUENCE: 47

```
atggaaaccc cagcgcagct tctcttcctc ctgctactct ggctcccaga taccaccgga     60

gaaattctgt tgacgcagtc tccaggcacc ctgtctttgt ctccagggga aagagccacc    120

ctctcctgca gggccagtca gagtgttagc agcagctact tagcctggta ccagcagaaa    180

cctggccagg ctcccaggct cctcatctat ggtgcatcca gcagggccac tggcatccca    240

gacaggttca gtggcagtgg gtctgggaca gacttcactc tcaccatcag cagactggag    300

cctgaagatt ttgcagtgta ttactgtcag cagtatggta gctcaccgac gttcggccaa    360

gggaccaagg tggaaatcaa a                                               381
```

<210> SEQ ID NO 48
<211> LENGTH: 127

-continued

```
<212> TYPE: PRT
<213> ORGANISM: Homo sapiens

<400> SEQUENCE: 48

Met Glu Thr Pro Ala Gln Leu Leu Phe Leu Leu Leu Leu Trp Leu Pro
1               5                   10                  15

Asp Thr Thr Gly Glu Ile Leu Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Ser Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Ser Ser Pro Thr Phe Gly Gln Gly Thr Lys Val Glu Ile Lys
        115                 120                 125
```

MONOCLONAL ANTIBODIES AGAINST GLYPICAN-3

BACKGROUND OF THE INVENTION

Glypican-3 is an oncofetal antigen that belongs to the glypican family of glycosyl-phosphatidylinositol-anchored heparin sulfate proteoglycans. Glypicans are characterized by a covalent linkage to complex polysaccharide chains called heparinsulphate glycosaminoglycans. Glypicans are involved in cell signaling at the cellular-extracellular matrix interface. (Sasisekharan et al., *Nature Reviews|Cancer, Volume* 2 (2002).) To date, six distinct members of the human glypican family have been identified. Cell membrane-bound Glypican-3 is composed of two subunits, linked by one or more disulfide bonds.

Glypican-3 is expressed in fetal liver and placenta during development and is down-regulated or silenced in normal adult tissues. Mutations and depletions in the Glypican-3 gene are responsible for the Simpson-Golabi-Behmel or Simpson dysmorphia syndrome in humans. Glypican-3 is expressed in various cancers and, in particular, hepatocellular carcinoma ("HCC"), melanoma, Wilm's tumor, and hepatoblastoma. (Jakubovic and Jothy; *Ex. Mol. Path.* 82:184-189 (2007); Nakatsura and Nishimura, *Biodrugs* 19(2):71-77 (2005).)

HCC is the third leading cause of cancer-related deaths worldwide. Each year, HCC accounts for about 1 million deaths. (Nakatsura and Nishimura, *Biodrugs* 19(2):71-77 (2005).) Hepatitis B virus, hepatitis C virus, and chronic heavy alcohol use leading to cirrhosis of the liver remain the most common causes of HCC. Its incidence has increased dramatically in the United States because of the spread of hepatitis C virus infection and is expected to increase for the next 2 decades. HCC is treated primarily by liver transplantation or tumor resection. Patient prognosis is dependent on both the underlying liver function and the stage at which the tumor is diagnosed. (Parikh and Hyman, *Am J. Med.* 120(3): 194-202 (2007).) Effective HCC treatment strategies are needed.

SUMMARY OF THE INVENTION

The present invention provides isolated monoclonal antibodies, in particular human monoclonal antibodies, that bind to Glypican-3 and that exhibit numerous desirable properties. These properties include high affinity binding to human Glypican-3.

In one aspect, the invention pertains to an isolated monoclonal antibody, or an antigen-binding portion thereof, wherein the antibody:

(a) binds to human Glypican-3 with a $K_D$ of $1\times10^{-7}$ M or less;

(b) binds to human CHO cells transfected with Glypican-3.

Preferably the antibody is a human antibody, although in alternative embodiments the antibody can be a murine antibody, a chimeric antibody or humanized antibody.

In one embodiment, the antibody binds to human Glypican-3 with a $K_D$ of $5\times10^{-8}$ M or less, binds to human Glypican-3 with a $K_D$ of $2\times10^{-8}$ M or less, binds to human Glypican-3 with a $K_D$ of $1\times10^{-8}$ M or less, binds to human Glypican-3 with a $K_D$ of $5\times10^{-9}$ M or less, binds to human Glypican-3 with a $K_D$ of $4\times10^{-9}$ M or less, binds to human Glypican-3 with a $K_D$ of $3\times10^{-9}$ M or less, or binds to human Glypican-3 with a $K_D$ of $2\times10^{-9}$ M or less.

In another embodiment, the invention provides an isolated monoclonal antibody, or antigen binding portion thereof, wherein the antibody cross-competes for binding to Glypican-3 with a reference antibody comprising:

(a) a heavy chain variable region comprising an amino acid sequence selected from the group consisting of SEQ ID NOs:19, 20, and 21; and (b) a light chain variable region comprising an amino acid sequence selected from the group consisting of SEQ ID NOs:22, 23, and 24.

In various embodiments, the reference antibody comprises:

(a) a heavy chain variable region comprising the amino acid sequence of SEQ ID NO:19; and (b) a light chain variable region comprising the amino acid sequence of SEQ ID NO:22;

or the reference antibody comprises:

(a) a heavy chain variable region comprising the amino acid sequence of SEQ ID NO:20; and (b) a light chain variable region comprising the amino acid sequence of SEQ ID NO:23.

or the reference antibody comprises:

(a) a heavy chain variable region comprising the amino acid sequence of SEQ ID NO:21; and (b) a light chain variable region comprising the amino acid sequence of SEQ ID NO:24.

In another aspect, the invention provides an isolated monoclonal antibody, or an antigen-binding portion thereof, comprising a heavy chain variable region that is the product of or derived from a human $V_H$ 5-51 gene, wherein the antibody specifically binds Glypican-3. The invention also provides an isolated monoclonal antibody, or an antigen-binding portion thereof, comprising a light chain variable region that is the product of or derived from a human $V_K$ A27 gene, wherein the antibody specifically binds Glypican-3.

In a preferred embodiment, the invention provides an isolated monoclonal antibody, or an antigen-binding portion thereof, comprising:

(a) a heavy chain variable region of a human $V_H$ 5-51 gene; and (b) a light chain variable region of a human $V_K$ A27 gene; wherein the antibody specifically binds to Glypican-3.

In another aspect, the invention provides an isolated monoclonal antibody, or antigen binding portion thereof, comprising:

a heavy chain variable region that comprises CDR1, CDR2, and CDR3 sequences; and a light chain variable region that comprises CDR1, CDR2, and CDR3 sequences, wherein:

(a) the heavy chain variable region CDR3 sequence comprises an amino acid sequence selected from the group consisting of amino acid sequences of SEQ ID NOs:7, 8, and 9, and conservative modifications thereof;

(b) the light chain variable region CDR3 sequence comprises an amino acid sequence selected from the group consisting of amino acid sequence of SEQ ID NOs:16, 17, and 18, and conservative modifications thereof;

(c) the antibody binds to human Glypican-3 with a $K_D$ of $1\times10^{-7}$ M or less; or (d) binds to human CHO cells transfected with Glypican-3.

Preferably, the heavy chain variable region CDR2 sequence comprises an amino acid sequence selected from the group consisting of amino acid sequences of SEQ ID NOs:4, 5, and 6, and conservative modifications thereof; and the light chain variable region CDR2 sequence comprises an amino acid sequence selected from the group consisting of amino acid sequences of SEQ ID NOs:13, 14, and 15, and conservative modifications thereof. Preferably, the heavy chain variable region CDR1 sequence comprises an amino acid sequence selected from the group consisting of amino acid sequences of SEQ ID NOs:1, 2, and 3, and conservative modifications thereof; and the light chain variable region CDR1 sequence comprises an amino acid sequence selected from the group consisting of amino acid sequences of SEQ ID NOs:10, 11, and 12, and conservative modifications thereof.

A preferred combination comprises:

(a) a heavy chain variable region CDR1 comprising SEQ ID NO:1;

(b) a heavy chain variable region CDR2 comprising SEQ ID NO:4;

(c) a heavy chain variable region CDR3 comprising SEQ ID NO:7;

(d) a light chain variable region CDR1 comprising SEQ ID NO:10;

(e) a light chain variable region CDR2 comprising SEQ ID NO:13; and (f) a light chain variable region CDR3 comprising SEQ ID NO:16.

Another preferred combination comprises:

(a) a heavy chain variable region CDR1 comprising SEQ ID NO:2;

(b) a heavy chain variable region CDR2 comprising SEQ ID NO:5;

(c) a heavy chain variable region CDR3 comprising SEQ ID NO:8;

(d) a light chain variable region CDR1 comprising SEQ ID NO:11;

(e) a light chain variable region CDR2 comprising SEQ ID NO:14; and (f) a light chain variable region CDR3 comprising SEQ ID NO:17.

Another preferred combination comprises:

(a) a heavy chain variable region CDR1 comprising SEQ ID NO:3;

(b) a heavy chain variable region CDR2 comprising SEQ ID NO:6;

(c) a heavy chain variable region CDR3 comprising SEQ ID NO:9;

(d) a light chain variable region CDR1 comprising SEQ ID NO:12;

(e) a light chain variable region CDR2 comprising SEQ ID NO:15; and (f) a light chain variable region CDR3 comprising SEQ ID NO:18.

Other preferred antibodies of the invention, or antigen binding portions thereof comprise:

(a) a heavy chain variable region comprising an amino acid sequence selected from the group consisting of SEQ ID NOs:19, 20 and 21; and (b) a light chain variable region comprising an amino acid sequence selected from the group consisting of SEQ ID NOs:22, 23, and 24;

wherein the antibody specifically binds Glypican-3.

A preferred combination comprises:

(a) a heavy chain variable region comprising the amino acid sequence of SEQ ID NO:19; and (b) a light chain variable region comprising the amino acid sequence of SEQ ID NO:22.

Another preferred combination comprises:

(a) a heavy chain variable region comprising the amino acid sequence of SEQ ID NO:20; and (b) a light chain variable region comprising the amino acid sequence of SEQ ID (c) NO:23.

Another preferred combination comprises:

(a) a heavy chain variable region comprising the amino acid sequence of SEQ ID NO:21; and (b) a light chain variable region comprising the amino acid sequence of SEQ ID NO:24.

In another aspect of the invention, antibodies, or antigen-binding portions thereof, are provided that compete for binding to Glypican-3 with any of the aforementioned antibodies.

The antibodies of the invention can be, for example, full-length antibodies, for example of an IgG1 or IgG4 isotype. Alternatively, the antibodies can be antibody fragments, such as Fab, Fab' or Fab'2 fragments, or single chain antibodies.

The invention also provides an immunoconjugate comprising an antibody of the invention, or antigen-binding portion thereof, linked to a therapeutic agent, such as a cytotoxin or a radioactive isotope. The invention also provides a bispecific molecule comprising an antibody, or antigen-binding portion thereof, of the invention, linked to a second functional moiety having a different binding specificity than said antibody, or antigen binding portion thereof.

Compositions comprising an antibody, or antigen-binding portion thereof, or immunoconjugate or bispecific molecule of the invention and a pharmaceutically acceptable carrier are also provided.

Nucleic acid molecules encoding the antibodies, or antigen-binding portions thereof, of the invention are also encompassed by the invention, as well as expression vectors comprising such nucleic acids and host cells comprising such expression vectors.

The invention provides methods of inhibiting the growth of tumor cells expressing Glypican-3 The methods comprise contacting the cells with an anti-Glypican-3 antibody, or antigen-binding portion thereof, in an amount effective to inhibit growth of the tumor cells. In a preferred embodiment, the tumor cells are derived from liver tissue. Additionally, the antibody, or antigen-binding portion thereof, may be immunoconjugates. The immunoconjugates of the invention may be therapeutic agents, for example, cytotoxins or radioactive isotopes.

Other features and advantages of the instant invention will be apparent from the following detailed description and examples which should not be construed as limiting. The contents of all references, Genbank entries, patents and published patent applications cited throughout this application are expressly incorporated herein by reference.

BRIEF DESCRIPTION OF THE DRAWINGS

FIG. 1A shows the nucleotide sequence (SEQ ID NO:25) and amino acid sequence (SEQ ID NO:19) of the heavy chain variable region of the 4A6 human monoclonal antibody. The CDR1 (SEQ ID NO:1), CDR2 (SEQ ID NO:4) and CDR3 (SEQ ID NO:7) regions are delineated and the V, D and J germline derivations are indicated. In addition, the bottom panel shows the nucleotide sequence (SEQ ID NO:37) and amino acid sequence (SEQ ID NO:38) of the heavy chain variable region of the 4A6 antibody, which include the leader sequences.

FIG. 1B shows the nucleotide sequence (SEQ ID NO:28) and amino acid sequence (SEQ ID NO:22) of the light chain variable region of the 4A6 human monoclonal antibody. The CDR1 (SEQ ID NO:10), CDR2 (SEQ ID NO:13) and CDR3 (SEQ ID NO:16) regions are delineated and the V and J germline derivations are indicated. In addition, the bottom panel shows the nucleotide sequence (SEQ ID NO:39) and amino acid sequence (SEQ ID NO:40) of the light chain variable region of the 4A6 antibody, which include the leader sequences.

FIG. 2A shows the nucleotide sequence (SEQ ID NO:26) and amino acid sequence (SEQ ID NO:20) of the heavy chain variable region of the 11E7 human monoclonal antibody. The CDR1 (SEQ ID NO:2), CDR2 (SEQ ID NO:5) and CDR3 (SEQ ID NO:8) regions are delineated and the V and J germline derivations are indicated. In addition, the bottom panel shows the nucleotide sequence (SEQ ID NO:41) and amino acid sequence (SEQ ID NO:42) of the heavy chain variable region of the 11E7 antibody, which include the leader sequences.

FIG. 2B shows the nucleotide sequence (SEQ ID NO:29) and amino acid sequence (SEQ ID NO:23) of the light chain variable region of the 11E7 human monoclonal antibody. The CDR1 (SEQ ID NO:11), CDR2 (SEQ ID NO:14) and CDR3 (SEQ ID NO:17) regions are delineated and the V and J germline derivations are indicated. In addition, the bottom panel shows the nucleotide sequence (SEQ ID NO:43) and amino acid sequence (SEQ ID NO:44) of the light chain variable region of the 11E7 antibody, which include the leader sequences.

FIG. 3A shows the nucleotide sequence (SEQ ID NO:27) and amino acid sequence (SEQ ID NO:21) of the heavy chain variable region of the 16D10 human monoclonal antibody. The CDR1 (SEQ ID NO:3), CDR2 (SEQ ID NO:6) and CDR3 (SEQ ID NO:9) regions are delineated and the V and J germline derivations are indicated. In addition, the bottom panel shows the nucleotide sequence (SEQ ID NO:45) and amino acid sequence (SEQ ID NO:46) of the heavy chain variable region of the 16D10 antibody, which include the leader sequences.

FIG. 3B shows the nucleotide sequence (SEQ ID NO:30) and amino acid sequence (SEQ ID NO:24) of the light chain variable region of the 16D10 human monoclonal antibody. The CDR1 (SEQ ID NO:12), CDR2 (SEQ ID NO:15) and CDR3 (SEQ ID NO:18) regions are delineated and the V and J germline derivations are indicated. In addition, the bottom panel shows the nucleotide sequence (SEQ ID NO:47) and amino acid sequence (SEQ ID NO:48) of the light chain variable region of the 16D10 antibody, which include the leader sequences.

FIG. 4 shows the alignment of the amino acid sequence of the heavy chain variable region of 4A6 (SEQ ID NO:19) with the human germline $V_H$ 5-51 amino acid sequence (SEQ ID NO:31) and the human germline $J_H$ JH4b amino acid sequence (SEQ ID NO:32).

FIG. 5 shows the alignment of the amino acid sequence of the heavy chain variable region of 11E7 (SEQ ID NO:20) with the human germline $V_H$ 5-51 amino acid sequences (SEQ ID NO:31) and the human germline $J_H$ JH4b amino acid sequence (SEQ ID NO:32).

FIG. 6 shows the alignment of the amino acid sequence of the heavy chain variable region of 16D10 (SEQ ID NO:21) with the human germline $V_H$ 5-51 amino acid sequences (SEQ ID NO:31) and the human germline $J_H$ JH4b amino acid sequence (SEQ ID NO:32).

FIG. 7 shows the alignment of the amino acid sequence of the light chain variable region of 4A6 (SEQ ID NO:22) with the human germline $V_k$ A27 amino acid sequence (SEQ ID NO:33) and the human germline $J_K$ JK4 amino acid sequence (SEQ ID NO:34).

FIG. 8 shows the alignment of the amino acid sequence of the light chain variable region of 11E7 (SEQ ID NO:23) with the human germline $V_k$ A27 amino acid sequence (SEQ ID NO:33) and the human germline $J_K$ JK4 amino acid sequence (SEQ ID NO:34).

FIG. 9 shows the alignment of the amino acid sequence of the light chain variable region of 16D10 (SEQ ID NO:24) with the human germline $V_k$ A27 amino acid sequence (SEQ ID NO:33) and the human germline $J_K$ JK1 amino acid sequence (SEQ ID NO:35).

FIG. 10 shows the binding affinity of the 4A6, 11E7, and 16D10 monoclonal antibodies for the HCC cell line Hep-3B. Binding was measured using a Fluorescence Activated Cell Sorter ("FACS") assay.

FIG. 11 shows that monoclonal antibodies 4A6, 11E7, and 16D10 specifically bind to the HCC cell lines Hep-3B and Hep-G2. Binding was measured using a FACS assay.

FIG. 12 shows that monoclonal antibodies 4A6, 11E7, and 16D10 specifically bind CHO cells stably transfected with a Glypican-3 expression vector but not to the parental CHO cell line. Binding was measured using a FACS assay.

FIG. 13 shows that monoclonal antibody 4A6 binds to liver cancer cells taken from patients. Antibody binding was revealed in an immunohistochemistry assay.

FIG. 14 shows that monoclonal antibodies 4A6, 11E7, and 16D10 can mediate natural killer ("NK") T-cell-mediated killing of Hep-3B cells. Killing was measured with an antibody-dependent cellular cytotoxicity ("ADCC") assay.

FIG. 15 shows that monoclonal antibodies 4A6, 11E7, and 16D10 are internalized by Hep-3B cells following binding to the cell-surface Glypican 3. Internalization was measured by a Hum-ZAP assay (Advanced Targeting Systems, San Diego, Calif.).

FIG. 16 shows that monoclonal antibodies 4A6, 11E7, and 16D10 are internalized by Hep-3B cells following binding to the cell-surface Glypican 3. Internalization was revealed in an immunofluorescence assay.

DETAILED DESCRIPTION OF THE INVENTION

The present invention relates to isolated monoclonal antibodies, particularly human monoclonal antibodies that bind specifically to Glypican-3 with high affinity. In certain embodiments, the antibodies of the invention are derived from particular heavy and light chain germline sequences and/or comprise particular structural features such as CDR regions comprising particular amino acid sequences. The invention provides isolated antibodies, methods of making such antibodies, immunoconjugates and bispecific molecules comprising such antibodies and pharmaceutical compositions containing the antibodies, immunoconjugates or bispecific molecules of the invention.

The invention also relates to methods of using the antibodies, such as to detect Glypican-3, as well as to treat diseases associated with expression of Glypican-3, such as liver cell malignancies that express Glypican-3. Accordingly, the invention also provides methods of using the anti-Glypican-3 antibodies of the invention to treat liver cell malignancies, for example, HCC.

In order that the present invention may be more readily understood, certain terms are first defined. Additional definitions are set forth throughout the detailed description.

The terms "Glypican-3, "glypican proteoglycan 3," "GPC3," "OTTHUMP00000062492," "GTR2-2," "SGB," "DGSX," "SDYS," "SGBS," "OCI-5," and "SGBS1" are used interchangeably, and include variants, isoforms and species homologs of human Glypican-3. Accordingly, human antibodies of this disclosure may, in certain cases, cross-react with Glypican-3 from species other than human. In certain embodiments, the antibodies may be completely specific for one or more human Glypican-3 proteins and may not exhibit species or other types of non-human cross-reactivity. The complete amino acid sequence of an exemplary human Glypican-3 has Genbank/NCBI accession number NM_004484 (SEQ ID NO:36).

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" refers to the biochemical relationship between several of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell. An example of a "cell surface receptor" of the present invention is the Glypican-3 receptor.

The term "antibody" as referred to herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $C_H1$, $C_H2$ and $C_H3$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., Glypican-3). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_H1$ domains; (ii) a $F(ab')_2$ fragment, a bivalent fragment comprising two Fab fragments linked by a disulfide bridge at the hinge region; (iii) a Fab' fragment, which is essentially an Fab with part of the hinge region (see, FUNDAMENTAL IMMUNOLOGY (Paul ed., 3.sup.rd ed. 1993); (iv) a Fd fragment consisting of the $V_H$ and $C_H1$ domains; (v) a Fv fragment consisting of the $V_L$ and $V_H$ domains of a single arm of an antibody, (vi) a dAb fragment (Ward et al., (1989) Nature 341:544-546), which consists of a $V_H$ domain; (vii) an isolated complementarity determining region (CDR); and (viii) a nanobody, a heavy chain variable region containing a single variable domain and two constant domains. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody," as used herein, is intended to refer to an antibody that is substantially free of other antibodies having different antigenic specificities (e.g., an isolated antibody that specifically binds Glypican-3 is substantially free of antibodies that specifically bind antigens other than Glypican-3). An isolated antibody that specifically binds Glypican-3 may, however, have cross-reactivity to other antigens, such as Glypican-3 molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody," as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM or IgGl) that is encoded by the heavy chain constant region genes.

The phrases "an antibody recognizing an antigen" and "an antibody specific for an antigen" are used interchangeably herein with the term "an antibody which binds specifically to an antigen."

The term "human antibody derivatives" refers to any modified form of the human antibody, e.g., a conjugate of the antibody and another agent or antibody.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

As used herein, an antibody that "specifically binds to human Glypican-3" is intended to refer to an antibody that binds to human Glypican-3 with a $K_D$ of $1\times10^{-7}$ M or less, more preferably $5\times10^{-8}$ M or less, more preferably $3\times10^{-8}$ M or less, more preferably $1\times10^{-8}$ M or less, even more preferably $5\times10^{-8}$ M or less.

The term "does not substantially bind" to a protein or cells, as used herein, means does not bind or does not bind with a high affinity to the protein or cells, i.e. binds to the protein or cells with a $K_D$ of $1\times10^{-6}$ M or more, more preferably $1\times10^{-5}$ M or more, more preferably $1\times10^{-4}$ M or more, more preferably $1\times10^{-3}$ M or more, even more preferably $1\times10^{-2}$ M or more.

The term "$K_{assoc}$" or "$K_a$," as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$," as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system.

As used herein, the term "high affinity" for an IgG antibody refers to an antibody having a $K_D$ of $1\times10^{-7}$ M or less, more preferably $5\times10^{-8}$ M or less, even more preferably $1\times10^{-8}$ M or less, even more preferably $5\times10^{-9}$ M or less and even more preferably $1\times10^{-9}$ M or less for a target antigen. However, "high affinity" binding can vary for other antibody isotypes. For example, "high affinity" binding for an IgM isotype refers to an antibody having a $K_D$ of $10^{-6}$ M or less, more preferably $10^{-7}$ M or less, even more preferably $10^{-8}$ M or less.

As used herein, the term "subject" includes any human or nonhuman animal. The term "nonhuman animal" includes all vertebrates, e.g., mammals and non-mammals, such as non-human primates, sheep, dogs, cats, horses, cows, chickens, amphibians, reptiles, etc.

Various aspects of the invention are described in further detail in the following subsections.

Anti-Glypican-3 Antibodies

The antibodies of the invention are characterized by particular functional features or properties of the antibodies. For example, the antibodies bind specifically to human Glypican-3. Preferably, an antibody of the invention binds to Glypican-3 with high affinity, for example with a $K_D$ of $1\times10^{-7}$ M or less. The anti-Glypican-3 antibodies of the invention preferably exhibit one or more of the following characteristics:

(a) binds to human Glypican-3 with a $K_D$ of $1\times10^{-7}$ M or less;

(b) binds to human CHO cells transfected with Glypican-3.

Preferably, the antibody binds to human Glypican-3 with a $K_D$ of $5\times10^{-8}$ M or less, binds to human Glypican-3 with a $K_D$ of $2\times10^{-8}$ M or less, binds to human Glypican-3 with a $K_D$ of $5\times10^{-9}$ M or less, binds to human Glypican-3 with a $K_D$ of $4\times10^{-9}$ M or less, binds to human Glypican-3 with a $K_D$ of $3\times10^{-9}$ M or less, or binds to human Glypican-3 with a $K_D$ of 2.1×10 M or less.

The antibody preferably binds to an antigenic epitope present in Glypican-3, which epitope is not present in other proteins. The antibody typically binds to Glypican-3 but does not bind to other proteins, or binds to other proteins with a low affinity, such as with a $K_D$ of $1\times10^{-6}$ M or more, more preferably $1\times10^{-5}$ M or more, more preferably $1\times10^{-4}$ M or more, more preferably $1\times10^{-3}$ M or more, even more preferably $1\times10^{-2}$ M or more. Preferably, the antibody does not substantially bind to related proteins, for example, the antibody does not substantially bind to Glypican-1, Glypican-2, Glypican-4 or Glypican-6.

In one embodiment, the antibody may be internalized into a cell expressing Glypican-3. Standard assays to evaluate antibody internalization are known in the art, including, for example, a HumZap internalization assay.

Standard assays to evaluate the binding ability of the antibodies toward Glypican-3 are known in the art, including for example, ELISAs, Western blots, RIAs, and flow cytometry analysis. Suitable assays are described in detail in the Examples. The binding kinetics (e.g., binding affinity) of the antibodies also can be assessed by standard assays known in the art, such as by Biacore® system analysis. To assess binding to tumor cells, e.g. Hep-3b or Hep-G2 (ATCC Deposit No. HB-8064 and HB-8065, respectively), cells can be obtained from publicly available sources, such as the American Type Culture Collection, and used in standard assays, such as flow cytometric analysis.

Monoclonal Antibodies 4A6, 11E7, and 16D10

Preferred antibodies of the invention are the human monoclonal antibodies 4A6, 11E7, and 16D10, isolated and structurally characterized as described in Examples 1 and 2. The $V_H$ amino acid sequences of 4A6, 11E7, and 16D10 are shown in SEQ ID NOs:19, 20, and 21, respectively. The $V_L$ amino acid sequences of 4A6, 11E7, and 16D10 are shown in SEQ ID NOs:22, 23, and 24, respectively.

Given that each of these antibodies can bind to Glypican-3, the $V_H$ and $V_L$ sequences can be "mixed and matched" to create other anti-Glypican-3 binding molecules of the invention. Glypican-3 binding of such "mixed and matched" antibodies can be tested using the binding assays described above and in the Examples (e.g., ELISAs). Preferably, when $V_H$ and $V_L$ chains are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

Accordingly, in one aspect, the invention provides an isolated monoclonal antibody, or antigen binding portion thereof comprising:

(a) a heavy chain variable region comprising an amino acid sequence selected from the group consisting of SEQ ID NOs: 19, 20, and 21; and (b) a light chain variable region comprising an amino acid sequence selected from the group consisting of SEQ ID NOs: 22, 23, and 24;

wherein the antibody specifically binds Glypican-3, preferably human Glypican-3.

Preferred heavy and light chain combinations include:

(a) a heavy chain variable region comprising the amino acid sequence of SEQ ID NO:19; and (b) a light chain variable region comprising the amino acid sequence of SEQ ID NO:22; or (b) a heavy chain variable region comprising the amino acid sequence of SEQ ID NO:20; and (b) a light chain variable region comprising the amino acid sequence of SEQ ID NO:23.

(c) a heavy chain variable region comprising the amino acid sequence of SEQ ID NO:21; and (b) a light chain variable region comprising the amino acid sequence of SEQ ID NO:24.

In another aspect, the invention provides antibodies that comprise the heavy chain and light chain CDR1s, CDR2s and CDR3s of 4A6, 11E7, and 16D10, or combinations thereof. The amino acid sequences of the $V_H$ CDR1s of 4A6, 11E7, and 16D10 are shown in SEQ ID NOs:1, 2 and 3, respectively. The amino acid sequences of the $V_H$ CDR2s of 4A6, 11E7, and 16D10 are shown in SEQ ID NOs:4, 5, and 6, respectively. The amino acid sequences of the $V_H$ CDR3s of 4A6, 11E7, and 16D10 are shown in SEQ ID NOs:7, 8, and 9, respectively. The amino acid sequences of the $V_k$ CDR1s of 4A6, 11E7, and 16D10 are shown in SEQ ID NOs:10, 11, and 12, respectively. The amino acid sequences of the $V_k$ CDR2s of 4A6, 11E7, and 16D10 are shown in SEQ ID NOs:13, 14, and 15, respectively. The amino acid sequences of the $V_k$ CDR3s of 4A6, 11E7, and 16D10 are shown in SEQ ID NOs:16, 17, and 18, respectively. The CDR regions are delineated using the Kabat system (Kabat, E. A., et al. (1991) Sequences of Proteins of Immunological Interest, Fifth Edition, U.S. Department of Health and Human Services, NIH Publication No. 91-3242).

Given that each of these antibodies can bind to Glypican-3 and that antigen-binding specificity is provided primarily by the CDR1, CDR2, and CDR3 regions, the $V_H$ CDR1, CDR2, and CDR3 sequences and $V_k$ CDR1, CDR2, and CDR3 sequences can be "mixed and matched" (i.e., CDRs from different antibodies can be mixed and match, although each antibody must contain a $V_H$ CDR1, CDR2, and CDR3 and a $V_k$ CDR1, CDR2, and CDR3) to create other anti-Glypican-3 binding molecules of the invention. Glypican-3 binding of such "mixed and matched" antibodies can be tested using the binding assays described above and in the Examples (e.g., ELISAs, Biacore® analysis). Preferably, when $V_H$ CDR sequences are mixed and matched, the CDR1, CDR2 and/or CDR3 sequence from a particular $V_H$ sequence is replaced with a structurally similar CDR sequence(s). Likewise, when $V_k$ CDR sequences are mixed and matched, the CDR1, CDR2 and/or CDR3 sequence from a particular $V_k$ sequence preferably is replaced with a structurally similar CDR sequence(s). It will be readily apparent to the ordinarily skilled artisan that novel $V_H$ and $V_L$ sequences can be created by substituting one or more $V_H$ and/or $V_L$ CDR region sequences with structurally similar sequences from the CDR sequences disclosed herein for monoclonal antibodies 4A6, 11E7, and 16D10.

Accordingly, in another aspect, the invention provides an isolated monoclonal antibody, or antigen binding portion thereof comprising:

(a) a heavy chain variable region CDR1 comprising an amino acid sequence selected from the group consisting of SEQ ID NOs:1, 2 and 3;

(b) a heavy chain variable region CDR2 comprising an amino acid sequence selected from the group consisting of SEQ ID NOs:4, 5, and 6;

(c) a heavy chain variable region CDR3 comprising an amino acid sequence selected from the group consisting of SEQ ID NOs:7, 8, and 9;

(d) a light chain variable region CDR1 comprising an amino acid sequence selected from the group consisting of SEQ ID NOs:10, 11, and 12;

(e) a light chain variable region CDR2 comprising an amino acid sequence selected from the group consisting of SEQ ID NOs:13, 14, and 15; and (f) a light chain variable region CDR3 comprising an amino acid sequence (g) selected from the group consisting of SEQ ID NOs:16, 17, and 18;

wherein the antibody specifically binds Glypican-3, preferably human Glypican-3.

In a preferred embodiment, the antibody comprises:

(a) a heavy chain variable region CDR1 comprising SEQ ID NO:1;

(b) a heavy chain variable region CDR2 comprising SEQ ID NO:4;

(c) a heavy chain variable region CDR3 comprising SEQ ID NO:7;

(d) a light chain variable region CDR1 comprising SEQ ID NO:10;

(e) a light chain variable region CDR2 comprising SEQ ID NO:13; and (f) a light chain variable region CDR3 comprising SEQ ID NO:16.

In another preferred embodiment, the antibody comprises:

(a) a heavy chain variable region CDR1 comprising SEQ ID NO:2;

(b) a heavy chain variable region CDR2 comprising SEQ ID NO:5;

(c) a heavy chain variable region CDR3 comprising SEQ ID NO:8;

(d) a light chain variable region CDR1 comprising SEQ ID NO:11;

(e) a light chain variable region CDR2 comprising SEQ ID NO:14; and (f) a light chain variable region CDR3 comprising SEQ ID NO:17.

In another preferred embodiment, the antibody comprises:

(a) a heavy chain variable region CDR1 comprising SEQ ID NO:3;

(b) a heavy chain variable region CDR2 comprising SEQ ID NO:6;

(c) a heavy chain variable region CDR3 comprising SEQ ID NO:9;

(d) a light chain variable region CDR1 comprising SEQ ID NO:12;

(e) a light chain variable region CDR2 comprising SEQ ID NO:15; and (f) a light chain variable region CDR3 comprising SEQ ID NO:18.

It is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, for example, Klimka et al., *British J. of Cancer* 83(2):252-260 (2000) (describing the production of a humanized anti-CD30 antibody using only the heavy chain variable domain CDR3 of murine anti-CD30 antibody Ki-4); Beiboer et al., *J. Mol. Biol.* 296:833-849 (2000) (describing recombinant epithelial glycoprotein-2 (EGP-2) antibodies using only the heavy chain CDR3 sequence of the parental murine MOC-31 anti-EGP-2 antibody); Rader et al., *Proc. Natl. Acad. Sci. U.S.A.* 95:8910-8915 (1998) (describing a panel of humanized anti-integrin $\alpha_v\beta_3$ antibodies using a heavy and light chain variable CDR3 domain of a murine anti-integrin $\alpha_v\beta_3$ antibody LM609 wherein each member antibody comprises a distinct sequence outside the CDR3 domain and capable of binding the same epitope as the parent murine antibody with affinities as high or higher than the parent murine antibody); Barbas et al., *J. Am. Chem. Soc.* 116:2161-2162 (1994) (disclosing that the CDR3 domain provides the most significant contribution to antigen binding); Barbas et al., *Proc. Natl. Acad. Sci. U.S.A.* 92:2529-2533 (1995) (describing the grafting of heavy chain CDR3 sequences of three Fabs (SI-1, SI-40, and SI-32) against human placental DNA onto the heavy chain of an anti-tetanus toxoid Fab thereby replacing the existing heavy chain CDR3 and demonstrating that the CDR3 domain alone conferred binding specificity); and Ditzel et al., *J. Immunol.* 157:739-749 (1996) (describing grafting studies wherein transfer of only the heavy chain CDR3 of a parent polyspecific Fab LNA3 to a heavy chain of a monospecific IgG tetanus toxoid-binding Fab p313 antibody was sufficient to retain binding specificity of the parent Fab). Each of these references is hereby incorporated by reference in its entirety.

Accordingly, the present invention provides monoclonal antibodies comprising one or more heavy and/or light chain CDR3 domains from an antibody derived from a human or non-human animal, wherein the monoclonal antibody is capable of specifically binding to Glypican-3. Within certain aspects, the present invention provides monoclonal antibodies comprising one or more heavy and/or light chain CDR3 domain from a non-human antibody, such as a mouse or rat antibody, wherein the monoclonal antibody is capable of specifically binding to Glypican-3. Within some embodiments, such inventive antibodies comprising one or more heavy and/or light chain CDR3 domain from a non-human antibody (a) are capable of competing for binding with; (b) retain the functional characteristics; (c) bind to the same epitope; and/or (d) have a similar binding affinity as the corresponding parental non-human antibody.

Within other aspects, the present invention provides monoclonal antibodies comprising one or more heavy and/or light chain CDR3 domain from a human antibody, such as, for example, a human antibody obtained from a non-human animal, wherein the human antibody is capable of specifically binding to Glypican-3. Within other aspects, the present invention provides monoclonal antibodies comprising one or more heavy and/or light chain CDR3 domain from a first human antibody, such as, for example, a human antibody obtained from a non-human animal, wherein the first human antibody is capable of specifically binding to Glypican-3 and wherein the CDR3 domain from the first human antibody replaces a CDR3 domain in a human antibody that is lacking binding specificity for Glypican-3 to generate a second human antibody that is capable of specifically binding to Glypican-3. Within some embodiments, such inventive antibodies comprising one or more heavy and/or light chain CDR3 domains from the first human antibody (a) are capable of competing for binding with; (b) retain the functional characteristics; (c) bind to the same epitope; and/or (d) have a similar binding affinity as the corresponding parental first human antibody. In preferred embodiments, the first human antibody is 4A6, 11E7, and 16D10.

Antibodies Having Particular Germline Sequences

In certain embodiments, an antibody of the invention comprises a heavy chain variable region from a particular germline heavy chain immunoglobulin gene and/or a light chain variable region from a particular germline light chain immunoglobulin gene.

For example, in a preferred embodiment, the invention provides an isolated monoclonal antibody, or an antigen-binding portion thereof, comprising a heavy chain variable region that is the product of or derived from a human $V_H$ 5-51 gene, wherein the antibody specifically binds Glypican-3. In another preferred embodiment, the invention provides an isolated monoclonal antibody, or an antigen-binding portion thereof, comprising a light chain variable region that is the product of or derived from a human $V_K$ A27 gene, wherein the antibody specifically binds Glypican-3. In yet another preferred embodiment, the invention provides an isolated monoclonal antibody, or antigen-binding portion thereof, wherein the antibody:

(a) comprises a heavy chain variable region that is the product of or derived from a human $V_H$ 5-51 gene (which gene encodes the amino acid sequences set forth in SEQ ID NO:31);

(b) comprises a light chain variable region that is the product of or derived from a human $V_K$ A27 gene (which gene encodes the amino acid sequences set forth in SEQ ID NO:33); and (c) specifically binds to Glypican-3, preferably human Glypican-3.

Examples of Antibodies Having $V_H$ 5-51 and $V_K$ A27 are 4A6, 11E7, and 16D10

As used herein, a human antibody comprises heavy or light chain variable regions that is "the product of" or "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Homologous Antibodies

In yet another embodiment, an antibody of the invention comprises heavy and light chain variable regions comprising amino acid sequences that are homologous to the amino acid sequences of the preferred antibodies described herein, and wherein the antibodies retain the desired functional properties of the anti-Glypican-3 antibodies of the invention.

For example, the invention provides an isolated monoclonal antibody, or antigen binding portion thereof, comprising a heavy chain variable region and a light chain variable region, wherein:

(a) the heavy chain variable region comprises an amino acid sequence that is at least 80% homologous to an amino acid sequence selected from the group consisting of SEQ ID NOs:19, 20 and 21;

(b) the light chain variable region comprises an amino acid sequence that is at least 80% homologous to an amino acid sequence selected from the group consisting of SEQ ID NOs:22, 23, and 24; and (c) the antibody binds to human Glypican-3 with a $K_D$ of $1\times10^{-7}$ M or less.

The antibody may also bind to CHO cells transfected with human Glypican-3.

In various embodiments, the antibody can be, for example, a human antibody, a humanized antibody or a chimeric antibody.

In other embodiments, the $V_H$ and/or $V_L$ amino acid sequences may be 85%, 90%, 95%, 96%, 97%, 98% or 99% homologous to the sequences set forth above. An antibody having $V_H$ and $V_L$ regions having high (i.e., 80% or greater) homology to the $V_H$ and $V_L$ regions of the sequences set forth above, can be obtained by mutagenesis (e.g., site-directed or PCR-mediated mutagenesis) of nucleic acid molecules encoding SEQ ID NOs:25, 26, 27, 28, 29, and 30, followed by testing of the encoded altered antibody for the ability to bind glypican-3 using the functional assays described herein.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (*Comput. Appl. Biosci.,* 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453(1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al. (1990) *J. Mol. Biol.* 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used.

Antibodies with Conservative Modifications

In certain embodiments, an antibody of the invention comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein (e.g., 4A6, 11E7, and 16D10), or conservative modifications thereof, and wherein the antibodies retain the desired functional properties of the anti-Glypican-3 antibodies of the invention. Accordingly, the invention provides an isolated monoclonal antibody, or antigen binding portion thereof, comprising a heavy chain variable region comprising CDR1, CDR2, and CDR3 sequences and a light chain variable region comprising CDR1, CDR2, and CDR3 sequences, wherein:

(a) the heavy chain variable region CDR3 sequence comprises an amino acid sequence selected from the group consisting of amino acid sequences of SEQ ID NOs:7, 8, and 9, and conservative modifications thereof;

(b) the light chain variable region CDR3 sequence comprises an amino acid sequence selected from the group consisting of amino acid sequence of SEQ ID NOs:16, 17, and 18, and conservative modifications thereof; and (c) the antibody binds to human Glypican-3 with a $K_D$ of $1\times10^{-7}$ M or less.

The antibody may also bind to CHO cells transfected with human Glypican-3.

In a preferred embodiment, the heavy chain variable region CDR2 sequence comprises an amino acid sequence selected from the group consisting of amino acid sequences of SEQ ID NOs:4, 5, and 6, and conservative modifications thereof; and the light chain variable region CDR2 sequence comprises an amino acid sequence selected from the group consisting of amino acid sequences of SEQ ID NOs:13, 14, and 15, and conservative modifications thereof. In another preferred embodiment, the heavy chain variable region CDR1 sequence comprises an amino acid sequence selected from the group consisting of amino acid sequences of SEQ ID NOs:1, 2, and 3 and conservative modifications thereof; and the light chain variable region CDR1 sequence comprises an amino acid sequence selected from the group consisting of amino acid sequences of SEQ ID NOs:10, 11, and 12, and conservative modifications thereof.

In various embodiments, the antibody can be, for example, human antibodies, humanized antibodies or chimeric antibodies.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for the ability to bind glypican-3 using the functional assays described herein.

The heavy chain CDR1 sequence of SEQ ID NO:1, 2, or 3 may comprise one or more conservative sequence modification, such as one, two, three, four, five or more amino acid substitutions, additions or deletions; the light chain CDR1 sequence of SEQ ID NO:10, 11, or 12 may comprise one or more conservative sequence modification, such as one, two, three, four, five or more amino acid substitutions, additions or deletions; the heavy chain CDR2 sequence shown in SEQ ID NO:4, 5, or 6 may comprise one or more conservative sequence modification, such as one, two, three, four, five or more amino acid substitutions, additions or deletions; the light chain CDR2 sequence shown in SEQ ID NO:13, 14, or 15 may comprise one or more conservative sequence modification, such as one, two, three, four, five or more amino acid substitutions, additions or deletions; the heavy chain CDR3 sequence shown in SEQ ID NO:7, 8, or 9 may comprise one or more conservative sequence modification, such as one, two, three, four, five or more amino acid substitutions, additions or deletions; and/or the light chain CDR3 sequence shown in SEQ ID NO:16, 17, or 18 may comprise one or more conservative sequence modification, such as one, two, three, four, five or more amino acid substitutions, additions or deletions.

Antibodies that Bind to the Same Epitope as Anti-Glypican-3 Antibodies of the Invention In another embodiment, the invention provides antibodies that bind to the same epitope on human Glypican-3 as any of the Glypican-3 monoclonal antibodies of the invention (i.e., antibodies that have the ability to cross-compete for binding to Glypican-3 with any of the monoclonal antibodies of the invention). In preferred embodiments, the reference antibody for cross-competition studies can be the monoclonal antibody 4A6 (having $V_H$ and $V_L$ sequences as shown in SEQ ID NOs:19 and 22, respectively), the monoclonal antibody 11E7 (having $V_H$ and $V_L$ sequences as shown in SEQ ID NOs:20 and 23, respectively), or the monoclonal antibody 16D10 (having $V_H$ and $V_L$ sequences as shown in SEQ ID NOs:21 and 24, respectively). Such cross-competing antibodies can be identified based on their ability to cross-compete with 4A6, 11E7, or 16D10 in standard Glypican-3 binding assays. For example, Biacore analysis, ELISA assays or flow cytometry may be used to demonstrate cross-competition with the antibodies of the current invention. The ability of a test antibody to inhibit the binding of, for example, 4A6, 11E7, or 16D10, to human Glypican-3 demonstrates that the test antibody can compete with 4A6, 11E7, or 16D10 for binding to human Glypican-3 and thus binds to the same epitope on human Glypican-3 as 4A6, 11E7, or 16D10. In a preferred embodiment, the antibody that binds to the same epitope on human Glypican-3 as 4A6, 11E7, or 16D10 is a human monoclonal antibody. Such human monoclonal antibodies can be prepared and isolated as described in the Examples.

Engineered and Modified Antibodies

An antibody of the invention further can be prepared using an antibody having one or more of the $V_H$ and/or $V_L$ sequences disclosed herein can be used as starting material to engineer a modified antibody, which modified antibody may have altered properties as compared to the starting antibody. An antibody can be engineered by modifying one or more amino acids within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) *Nature* 332:323-327; Jones, P. et al. (1986) *Nature* 321:522-525; Queen, C. et al. (1989) *Proc. Natl. Acad. See. U.S.A.* 86:10029-10033; U.S. Pat. No. 5,225,539 to Winter, and U.S. Pat. Nos. 5,530,101; 5,585,089; 5,693,762 and 6,180,370 to Queen et al.)

Accordingly, another embodiment of the invention pertains to an isolated monoclonal antibody, or antigen binding portion thereof, comprising a heavy chain variable region comprising CDR1, CDR2, and CDR3 sequences comprising an amino acid sequence selected from the group consisting of SEQ ID NOs:1, 2, and 3, SEQ ID NOs:4, 5, and 6, and SEQ ID NOs:7, 8, and 9, respectively, and a light chain variable region comprising CDR1, CDR2, and CDR3 sequences comprising an amino acid sequence selected from the group consisting of SEQ ID NOs:10, 11, and 12, SEQ ID NOs:13, 14, and 15, and SEQ ID NOs:16, 17, and 18, respectively. Thus, such antibodies contain the $V_H$ and $V_L$ CDR sequences of monoclonal antibodies 4A6, 11E7, or 16D10 yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_H$ Segments Reveals a Strong Bias in their Usage" *Eur. J. Immunol.* 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank accession numbers: 1-69 (NG_0010109, NT_024637 and BC070333), 3-33 (NG_0010109 and NT_024637) and 3-7 (NG_0010109 and NT_024637). As another example, the following heavy chain germline sequences found in the HCo12 HuMAb mouse are available in the accompanying Genbank accession numbers: 1-69 (NG_0010109, NT_024637 and BC070333), 5-51 (NG_0010109 and NT_024637), 4-34 (NG_0010109 and NT_024637), 3-30.3 (CAJ556644) and 3-23 (AJ406678).

Antibody protein sequences are compared against a compiled protein sequence database using one of the sequence similarity searching methods called the Gapped BLAST (Altschul et al. (1997) *Nucleic Acids Research* 25:3389-3402), which is well known to those skilled in the art. BLAST is a heuristic algorithm in that a statistically significant alignment between the antibody sequence and the database sequence is likely to contain high-scoring segment pairs (HSP) of aligned words. Segment pairs whose scores cannot be improved by extension or trimming is called a hit. Briefly, the nucleotide sequences of VBASE origin are translated and the region between and including FR1 through FR3 framework region is retained. The database sequences have an average length of 98 residues. Duplicate sequences which are exact matches over the entire length of the protein are removed. A BLAST search for proteins using the program blastp with default, standard parameters except the low complexity filter, which is turned off, and the substitution matrix of BLOSUM62, filters for top 5 hits yielding sequence matches. The nucleotide sequences are translated in all six frames and the frame with no stop codons in the matching segment of the database sequence is considered the potential hit. This is in turn confirmed using the BLAST program tblastx, which translates the antibody sequence in all six frames and compares those translations to the VBASE nucleotide sequences dynamically translated in all six frames.

The identities are exact amino acid matches between the antibody sequence and the protein database over the entire length of the sequence. The positives (identities+substitution match) are not identical but amino acid substitutions guided by the BLOSUM62 substitution matrix. If the antibody sequence matches two of the database sequences with same identity, the hit with most positives would be decided to be the matching sequence hit.

Preferred framework sequences for use in the antibodies of the invention are those that are structurally similar to the framework sequences used by selected antibodies of the invention, e.g., similar to the $V_H$ 5-51 framework sequences (SEQ ID NO:31) and/or the $V_K$ A27 framework sequences (SEQ ID NO:33) used by preferred monoclonal antibodies of the invention. The $V_H$ CDR1, CDR2, and CDR3 sequences, and the $V_K$ CDR1, CDR2, and CDR3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al.).

Another type of variable region modification is to mutate amino acid residues within the $V_H$ and/or $V_K$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Preferably conservative modifications (as discussed above) are introduced. The mutations may be amino acid substitutions, additions or deletions, but are preferably substitutions. Moreover, typically no more than one, two, three, four or five residues within a CDR region are altered.

Accordingly, in another embodiment, the instant disclosure provides isolated anti-Glypican-3 monoclonal antibodies, or antigen binding portions thereof, comprising a heavy chain variable region comprising: (a) a $V_H$ CDR1 region comprising an amino acid sequence selected from the group consisting of SEQ ID NOs:1, 2, and 3, or an amino acid sequence having one, two, three, four or five amino acid substitutions, deletions or additions as compared to SEQ ID NOs:1, 2 and 3; (b) a $V_H$ CDR2 region comprising an amino acid sequence selected from the group consisting of SEQ ID NOs:4, 5, and 6, or an amino acid sequence having one, two, three, four or five amino acid substitutions, deletions or additions as compared to SEQ ID NOs:4, 5, and 6; (c) a $V_H$ CDR3 region comprising an amino acid sequence selected from the group consisting of SEQ ID NOs:7, 8, and 9, or an amino acid sequence having one, two, three, four or five amino acid substitutions, deletions or additions as compared to SEQ ID NOs:7, 8, and 9; (d) a $V_K$ CDR1 region comprising an amino acid sequence selected from the group consisting of SEQ ID NOs:10, 11, and 12, or an amino acid sequence having one, two, three, four or five amino acid substitutions, deletions or additions as compared to SEQ ID NOs: 10, 11, and 12; (e) a $V_K$ CDR2 region comprising an amino acid sequence selected from the group consisting of SEQ ID NOs: 13, 14, and 15, or an amino acid sequence having one, two, three, four or five amino acid substitutions, deletions or additions as compared to SEQ ID NOs: 13, 14, and 15; and (f) a $V_K$ CDR3 region comprising an amino acid sequence selected from the group consisting of SEQ ID NOs: 16, 17, and 18, or an amino acid sequence having one, two, three, four or five amino acid substitutions, deletions or additions as compared to SEQ ID NOs: 16, 17, and 18.

Engineered antibodies of the invention include those in which modifications have been made to framework residues within $V_H$ and/or $V_K$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. For example, for 4A6, using the Kabat numbering system, amino acid residue #73 (within FR3) of $V_H$ is an arginine (SEQ ID NO:19) whereas this residue in the corresponding $V_H$ 5-51 germline sequence is lysine (SEQ ID NO:31). To return the framework region sequences to their germline configuration, the somatic mutations can be "backmutated" to the germline sequence by, for example, site-directed mutagenesis or PCR-mediated mutagenesis (e.g., residue #73 (residue #8 of FR3) of the $V_H$ of 4A6 can be "backmutated" from arginine to lysine).

As another example, for 4A6, amino acid residue #76 (within FR3) of $V_H$ is arginine (SEQ ID NO:19) whereas this residue in the corresponding $V_H$ 5-51 germline sequence is a serine (SEQ ID NO:31). To return the framework region sequences to their germline configuration, for example, residue #76 (residue #11 of FR3) of the $V_H$ of 4A6 can be "backmutated" from arginine to serine. Such "backmutated" antibodies are also intended to be encompassed by the invention.

As another example, for 4A6, amino acid residue #89 (within FR3) of $V_H$ is leucine (SEQ ID NO:19) whereas this residue in the corresponding $V_H$ 5-51 germline sequence is a methionine (SEQ ID NO:31). To return the framework region sequences to their germline configuration, for example, residue #89 (residue #27 of FR3) of the $V_H$ of 4A6 can be "backmutated" from leucine to methionine. Such "backmutated" antibodies are also intended to be encompassed by the invention.

As another example, for 11E7, amino acid residue #76 (within FR3) of $V_H$ is arginine (SEQ ID NO:20) whereas this residue in the corresponding $V_H$ 5-51 germline sequence is a serine (SEQ ID NO:31). To return the framework region sequences to their germline configuration, for example, residue #76 (residue #11 of FR3) of the $V_H$ of 11E7 can be "backmutated" from arginine to serine. Such "backmutated" antibodies are also intended to be encompassed by the invention.

As another example, for 16D10, amino acid residue #10 (within FR1) of $V_H$ is aspartate (SEQ ID NO:21) whereas this residue in the corresponding $V_H$ 5-51 germline sequence is a glutamate (SEQ ID NO:31). To return the framework region sequences to their germline configuration, for example, residue #10 (residue #10 of FR1) of the $V_H$ of 16D10 can be "backmutated" from aspartate to glutamate. Such "backmutated" antibodies are also intended to be encompassed by the invention.

As another example, for 16D10, amino acid residue #12 (within FR1) of $V_H$ is threonine (SEQ ID NO:21) whereas this residue in the corresponding $V_H$ 5-51 germline sequence is a lysine (SEQ ID NO:31). To return the framework region sequences to their germline configuration, for example, residue #12 (residue #12 of FR1) of the $V_H$ of 16D10 can be "backmutated" from threonine to lysine. Such "backmutated" antibodies are also intended to be encompassed by the invention.

As another example, for 16D10, amino acid residue #24 (within FR1) of $V_H$ is valine (SEQ ID NO:21) whereas this residue in the corresponding $V_H$ 5-51 germline sequence is a glycine (SEQ ID NO:31). To return the framework region sequences to their germline configuration, for example, residue #24 (residue #24 of FR1) of the $V_H$ of 16D10 can be "backmutated" from valine to glycine. Such "backmutated" antibodies are also intended to be encompassed by the invention.

As another example, for 16D10, amino acid residue #28 (within FR1) of $V_H$ is arginine (SEQ ID NO:21) whereas this residue in the corresponding $V_H$ 5-51 germline sequence is a serine (SEQ ID NO:31). To return the framework region sequences to their germline configuration, for example, residue #28 (residue #28 of FR1) of the $V_H$ of 16D10 can be "backmutated" from arginine to serine. Such "backmutated" antibodies are also intended to be encompassed by the invention.

As another example, for 16D10, amino acid residue #37 (within FR2) of $V_H$ is methionine (SEQ ID NO:21) whereas this residue in the corresponding $V_H$ 5-51 germline sequence is a valine (SEQ ID NO:31). To return the framework region sequences to their germline configuration, for example, residue #37 (residue #2 of FR2) of the $V_H$ of 16D10 can be "backmutated" from methionine to valine. Such "backmutated" antibodies are also intended to be encompassed by the invention.

As another example, for 16D10, amino acid residue #41 (within FR2) of $V_H$ is serine (SEQ ID NO:21) whereas this residue in the corresponding $V_H$ 5-51 germline sequence is a proline (SEQ ID NO:31). To return the framework region sequences to their germline configuration, for example, residue #41 (residue #6 of FR2) of the $V_H$ of 16D10 can be "backmutated" from serine to proline. Such "backmutated" antibodies are also intended to be encompassed by the invention.

As another example, for 16D10, amino acid residue #66 (within FR3) of $V_H$ is histidine (SEQ ID NO:21) whereas this residue in the corresponding $V_H$ 5-51 germline sequence is a glutamine (SEQ ID NO:31). To return the framework region sequences to their germline configuration, for example, residue #66 (residue #1 of FR3) of the $V_H$ of 16D10 can be "backmutated" from histidine to glutamine. Such "backmutated" antibodies are also intended to be encompassed by the invention.

As another example, for 16D10, amino acid residue #76 (within FR3) of $V_H$ is asparagine (SEQ ID NO:21) whereas this residue in the corresponding $V_H$ 5-51 germline sequence is a serine (SEQ ID NO:31). To return the framework region sequences to their germline configuration, for example, residue #76 (residue #11 of FR3) of the $V_H$ of 16D10 can be "backmutated" from asparagine to serine. Such "backmutated" antibodies are also intended to be encompassed by the invention.

As another example, for 16D10, amino acid residue #81 (within FR3) of $V_H$ is arginine (SEQ ID NO:21) whereas this residue in the corresponding $V_H$ 5-51 germline sequence is a glutamine (SEQ ID NO:31). To return the framework region sequences to their germline configuration, for example, residue #81 (residue #16 of FR3) of the $V_H$ of 16D10 can be "backmutated" from arginine to glutamine. Such "backmutated" antibodies are also intended to be encompassed by the invention.

As another example, for 16D10, amino acid residue #89 (within FR3) of $V_H$ is isoleucine (SEQ ID NO:21) whereas this residue in the corresponding $V_H$ 5-51 germline sequence is a methionine (SEQ ID NO:31). To return the framework region sequences to their germline configuration, for example, residue #89 (residue #27 of FR3) of the $V_H$ of 16D10 can be "backmutated" from isoleucine to methionine. Such "backmutated" antibodies are also intended to be encompassed by the invention.

Similarly, the invention provides for the backmutation of framework residues in the light chain. For example, for 16D10, amino acid residue #3 (within FR1) of $V_K$ is leucine (SEQ ID NO:24) whereas this residue in the corresponding $V_K$ A27 germline sequence is a valine (SEQ ID NO:33). To return the framework region sequences to their germline configuration, for example, residue #3 (residue #3 of FR1) of the $V_K$ of 16D10 can be "backmutated" from leucine to valine.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half life. Various approaches are possible. For example, one or more of the following mutations can be introduced: T252L, T254S, and T256F, as described in U.S. Pat. No. 6,277,375 to Ward. Alternatively, to increase the biological half life, the antibody can be altered within the CH1 or $C_L$ region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered Clq binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al. In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for FcγR1, FcγRII, FcγRIII and FcRn have been mapped and variants with improved binding have been described (see Shields, R. L. et al. (2001) *J. Biol. Chem.* 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 (alpha(1,6)fucosyltransferase), such that antibodies expressed in the Ms704, Ms705, and Ms709 cell lines lack fucose on their carbohydrates. The Ms704, Ms705, and Ms709 $FUT8^{-/-}$ cell lines were created by the targeted disruption of the FUT8 gene in CHO/DG44 cells using two replacement vectors (see U.S. Patent Publication No. 20040110704 by Yamane et al. and Yamane-Ohnuki et al. (2004) *Biotechnol Bioeng* 87:614-22). As another example, EP 1,176,195 by Hanai et al. describes a cell line with a functionally disrupted FUT8 gene, which encodes a fucosyl transferase, such that antibodies expressed in such a cell line exhibit hypofucosylation by reducing or eliminating the alpha 1,6 bond-related enzyme. Hanai et al. also describe cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) *J. Biol. Chem.* 277:26733-26740). PCT Publication WO 99/54342 by Umana et al. describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) *Nat. Biotech.* 17:176-180). Alternatively, the fucose residues of the antibody may be cleaved off using a fucosidase enzyme. For example, the fucosidase alpha-L-fucosidase removes fucosyl residues from antibodies (Tarentino, A. L. et al. (1975) *Biochem.* 14:5516-23).

Another modification of the antibodies herein that is contemplated by the invention is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono(C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al.

Antibody Physical Properties

The antibodies of the present invention may be further characterized by the various physical properties of the anti-Glypican-3 antibodies. Various assays may be used to detect and/or differentiate different classes of antibodies based on these physical properties.

In some embodiments, antibodies of the present invention may contain one or more glycosylation sites in either the light or heavy chain variable region. The presence of one or more glycosylation sites in the variable region may result in increased immunogenicity of the antibody or an alteration of the pK of the antibody due to altered antigen binding (Marshall et al (1972) *Annu Rev Biochem* 41:673-702; Gala FA and Morrison S L (2004) *J Immunol* 172:5489-94; Wallick et al (1988) *J Exp Med* 168:1099-109; Spiro R G (2002) *Glycobiology* 12:43 R-56R; Parekh et al (1985) *Nature* 316:452-7; Mimura et al. (2000) *Mol Immunol* 37:697-706). Glycosylation has been known to occur at motifs containing an N-X-S/T sequence. Variable region glycosylation may be tested using a Glycoblot assay, which cleaves the antibody to produce a Fab, and then tests for glycosylation using an assay that measures periodate oxidation and Schiff base formation. Alternatively, variable region glycosylation may be tested using Dionex light chromatography (Dionex-LC), which cleaves saccharides from a Fab into monosaccharides and analyzes the individual saccharide content. In some instances, it is preferred to have an anti-Glypican-3 antibody that does not contain variable region glycosylation. This can be achieved either by selecting antibodies that do not contain the glycosylation motif in the variable region or by mutating residues within the glycosylation motif using standard techniques well known in the art.

In a preferred embodiment, the antibodies of the present invention do not contain asparagine isomerism sites. A deamidation or isoaspartic acid effect may occur on N-G or D-G sequences, respectively. The deamidation or isoaspartic acid effect results in the creation of isoaspartic acid which decreases the stability of an antibody by creating a kinked structure off a side chain carboxy terminus rather than the main chain. The creation of isoaspartic acid can be measured using an iso-quant assay, which uses a reverse-phase HPLC to test for isoaspartic acid.

Each antibody will have a unique isoelectric point (pI), but generally antibodies will fall in the pH range of between 6 and 9.5. The pI for an IgG1 antibody typically falls within the pH range of 7-9.5 and the pI for an IgG4 antibody typically falls within the pH range of 6-8. Antibodies may have a pI that is outside this range. Although the effects are generally unknown, there is speculation that antibodies with a pI outside the normal range may have some unfolding and instability under in vivo conditions. The isoelectric point may be tested using a capillary isoelectric focusing assay, which creates a pH gradient and may utilize laser focusing for increased accuracy (Janini et al (2002) *Electrophoresis* 23:1605-11; Ma et al. (2001) *Chromatographia* 53:S75-89; Hunt et al (1998) *J Chromatogr A* 800:355-67). In some instances, it is preferred to have an anti-Glypican-3 antibody that contains a pI value that falls in the normal range. This can be achieved either by selecting antibodies with a pI in the normal range, or by mutating charged surface residues using standard techniques well known in the art.

Each antibody will have a melting temperature that is indicative of thermal stability (Krishnamurthy R and Manning MC (2002) *Curr Pharm Biotechnol* 3:361-71). A higher thermal stability indicates greater overall antibody stability in vivo. The melting point of an antibody may be measure using techniques such as differential scanning calorimetry (Chen et al (2003) *Pharm Res* 20:1952-60; Ghirlando et al (1999) *Immunol Lett* 68:47-52). $T_{M1}$ indicates the temperature of the initial unfolding of the antibody. $T_{M2}$ indicates the temperature of complete unfolding of the antibody. Generally, it is preferred that the $T_{M1}$ of an antibody of the present invention is greater than 60° C., preferably greater than 65° C., even more preferably greater than 70° C. Alternatively, the thermal stability of an antibody may be measure using circular dichroism (Murray et al. (2002) *J. Chromatogr Sci* 40:343-9).

In a preferred embodiment, antibodies are selected that do not rapidly degrade. Fragmentation of an anti-Glypican-3 antibody may be measured using capillary electrophoresis (CE) and MALDI-MS, as is well understood in the art (Alexander A J and Hughes D E (1995) *Anal Chem* 67:3626-32).

In another preferred embodiment, antibodies are selected that have minimal aggregation effects. Aggregation may lead to triggering of an unwanted immune response and/or altered or unfavorable pharmacokinetic properties. Generally, antibodies are acceptable with aggregation of 25% or less, preferably 20% or less, even more preferably 15% or less, even more preferably 10% or less and even more preferably 5% or less. Aggregation may be measured by several techniques well known in the art, including size-exclusion column (SEC) high performance liquid chromatography (HPLC), and light scattering to identify monomers, dimers, trimers or multimers.

Methods of Engineering Antibodies

As discussed above, the anti-Glypican-3 antibodies having $V_H$ and $V_K$ sequences disclosed herein can be used to create new anti-Glypican-3 antibodies by modifying the $V_H$ and/or $V_K$ sequences, or the constant region(s) attached thereto. Thus, in another aspect of the invention, the structural features of an anti-Glypican-3 antibody of the invention, e.g. 4A6, 11E7, and 16D10, are used to create structurally related anti-Glypican-3 antibodies that retain at least one functional property of the antibodies of the invention, such as binding to human Glypican-3. For example, one or more CDR regions of 4A6, 11E7, and 16D10, or mutations thereof, can be combined recombinantly with known framework regions and/or other CDRs to create additional, recombinantly-engineered, anti-Glypican-3 antibodies of the invention, as discussed above. Other types of modifications include those described in the previous section. The starting material for the engineering method is one or more of the $V_H$ and/or $V_K$ sequences provided herein, or one or more CDR regions thereof. To create the engineered antibody, it is not necessary to actually prepare (i.e., express as a protein) an antibody having one or more of the $V_H$ and/or $V_K$ sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the invention provides a method for preparing an anti-Glypican-3 antibody comprising:

(a) providing: (i) a heavy chain variable region antibody sequence comprising a CDR1 sequence selected from the group consisting of SEQ ID NOs:1, 2, and 3, a CDR2 sequence selected from the group consisting of SEQ ID NOs:4, 5, and 6, and/or a CDR3 sequence selected from the group consisting of SEQ ID NOs:7, 8, and 9; and/or (ii) a light chain variable region antibody sequence comprising a CDR1 sequence selected from the group consisting of SEQ ID NOs:10, 11, and 12, a CDR2 sequence selected from the group consisting of SEQ ID NOs: 13, 14, and 15, and/or a CDR3 sequence selected from the group consisting of SEQ ID NOs: 16, 17, and 18;

(b) altering at least one amino acid residue within the heavy chain variable regionantibody sequence and/or the light chain variable region antibody sequence to create at least one altered antibody sequence; and (c) expressing the altered antibody sequence as a protein.

Standard molecular biology techniques can be used to prepare and express the altered antibody sequence.

Preferably, the antibody encoded by the altered antibody sequence(s) is one that retains one, some or all of the functional properties of the anti-Glypican-3 antibodies described herein, which functional properties include, but are not limited to:

(i) binds to human Glypican-3 with a $K_D$ of $1\times10^{-7}$ M or less;

(ii) binds to human CHO cells transfected with Glypican-3.

The functional properties of the altered antibodies can be assessed using standard assays available in the art and/or described herein, such as those set forth in the Examples (e.g., flow cytometry, binding assays).

In certain embodiments of the methods of engineering antibodies of the invention, mutations can be introduced randomly or selectively along all or part of an anti-Glypican-3 antibody coding sequence and the resulting modified anti-Glypican-3 antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Nucleic Acid Molecules Encoding Antibodies of the Invention

Another aspect of the invention pertains to nucleic acid molecules that encode the antibodies of the invention. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsC1 banding, column chromatography, agarose gel electrophoresis and others well known in the art. See, F. Ausubel, et al., ed. (1987) Current Protocols in Molecular Biology, Greene Publishing and Wiley Interscience, New York. A nucleic acid of the invention can be, for example, DNA or RNA and may or may not contain intronic sequences. In a preferred embodiment, the nucleic acid is a cDNA molecule.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Preferred nucleic acids molecules of the invention are those encoding the $V_H$ and $V_L$ sequences of the 4A6, 11E7, or 16D10 monoclonal antibodies. DNA sequences encoding the $V_H$ sequences of 4A6, 11E7, or 16D10 are shown in SEQ ID NOs:25, 26, and 27, respectively. DNA sequences encoding the $V_L$ sequences of 4A6, 11E7, or 16D10 are shown in SEQ ID NOs:28, 29, and 30, respectively. Other preferred nucleic acids of the invention are nucleic acids having at least 80% sequence identity, such as at least 85%, at least 90%, at least 95%, at least 98% or at least 99% sequence identity, with one of the sequences shown in SEQ ID NO:25, 26, 27, 28, 29, and 30, which nucleic acids encode an antibody of the invention, or an antigen-binding portion thereof.

The percent identity between two nucleic acid sequences is the number of positions in the sequence in which the nucleotide is identical, taking into account the number of gaps and the length of each gap, which need to be introduced for optimal alignment of the two sequences. The comparison of sequences and determination of percent identity between two sequences can be accomplished using a mathematical algorithm, such as the algorithm of Meyers and Miller or the XBLAST program of Altschul described above.

Still further, preferred nucleic acids of the invention comprise one or more CDR-encoding portions of the nucleic acid sequences shown in SEQ ID NOs: 25, 26, 27, 28, 29, and 30. In this embodiment, the nucleic acid may encode the heavy chain CDR1, CDR2 and/or CDR3 sequence of 4A6, 11E7, or 16D10 or the light chain CDR1, CDR2 and/or CDR3 sequence of 4A6, 11E7, or 16D10.

Nucleic acids which have at least 80%, such as at least 85%, at least 90%, at least 95%, at least 98% or at least 99% sequence identity, with such a CDR-encoding portion of SEQ ID NO: 25, 26, 27, 28, 29, or 30 are also preferred nucleic acids of the invention. Such nucleic acids may differ from the corresponding portion of SEQ ID NO: 25, 26, 27, 28, 29, or 30 in a non-CDR coding region and/or in a CDR-coding region. Where the difference is in a CDR-coding region, the nucleic acid CDR region encoded by the nucleic acid typically comprises one or more conservative sequence modification as defined herein compared to the corresponding CDR sequence of 4A6, 11E7, and 16D10.

Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked," as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as a Fab light chain gene) by operatively linking the $V_L$-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. In preferred embodiments, the light chain constant region can be a kappa or lambda constant region.

To create a scFv gene, the VH- and VL-encoding DNA fragments are operatively linked to another fragment encoding a flexible linker, e.g., encoding the amino acid sequence (Gly4-Ser)3, such that the VH and VL sequences can be expressed as a contiguous single-chain protein, with the VL and VH regions joined by the flexible linker (see e.g., Bird et al. (1988) Science 242:423-426; Huston et al. (1988) Proc. Natl. Acad. Sci. USA 85:5879-5883; McCafferty et al., (1990) Nature 348:552-554).

Production of Monoclonal Antibodies

Monoclonal antibodies (mAbs) of the present invention can be produced by a variety of techniques, including conventional monoclonal antibody methodology e.g., the standard somatic cell hybridization technique of Kohler and Milstein (1975) Nature 256: 495. Although somatic cell hybridization procedures are preferred, in principle, other techniques for producing monoclonal antibody can be employed e.g., viral or oncogenic transformation of B lymphocytes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a non-human monoclonal antibody prepared as described above. DNA encoding the heavy and light chain immunoglobulins can be obtained from the non-human hybridoma of interest and engineered to contain non-murine (e.g., human) immunoglobulin sequences using standard molecular biology techniques. For example, to create a chimeric antibody, murine variable regions can be linked to human constant regions using methods known in the art (see e.g., U.S. Pat. No. 4,816,567 to Cabilly et al.). To create a humanized antibody, murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In a preferred embodiment, the antibodies of the invention are human monoclonal antibodies. Such human monoclonal antibodies directed against Glypican-3 can be generated using transgenic or transchromosomic mice carrying parts of the human immune system rather than the mouse system. These transgenic and transchromosomic mice include mice referred to herein as the HuMAb Mouse® and KM Mouse®, respectively, and are collectively referred to herein as "human Ig mice."

The HuMAb Mouse® (Medarex®, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg, et al. (1994) Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. 13: 65-93, and Harding, F. and Lonberg, N. (1995) Ann. N.Y. Acad. Sci. 764:536-546). Preparation and use of the HuMAb Mouse®, and the genomic modifications carried by such mice, is further described in Taylor, L. et al. (1992) Nucleic Acids Research 20:6287-6295; Chen, J. et al. (1993) International Immunology 5: 647-656; Tuaillon et al. (1993) Proc. Natl. Acad. Sci. USA 90:3720-3724; Choi et al. (1993) Nature Genetics 4:117-123; Chen, J. et al. (1993) EMBO J. 12: 821-830; Tuaillon et al. (1994) J. Immunol. 152:2912-2920; Taylor, L. et al. (1994) International Immunology 6: 579-591; and Fishwild, D. et al. (1996) Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchomosomes, such as a mouse that carries a human heavy chain transgene and a human light chain transchromosome. This mouse is referred to herein as a "KM Mouse®," and is described in detail in PCT Publication WO 02/43478 to Ishida et al.

Still further, alternative transgenic animal systems expressing human immunoglobulin genes are available in the art and can be used to raise anti-Glypican-3 antibodies of the invention. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-Glypican-3 antibodies of the invention. For example, mice carrying both a human heavy chain transchromosome and a human light chain tranchromosome, referred to as "TC mice" can be used; such mice are described in Tomizuka et al. (2000) Proc. Natl. Acad. Sci. USA 97:722-727. Furthermore, cows carrying human heavy and light chain transchromosomes have been described in the art (Kuroiwa et al. (2002) Nature Biotechnology 20:889-894) and PCT application No. WO/2002/092812 and can be used to raise anti-Glypican-3 antibodies of the invention.

Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Immunization of Human Ig Mice

When human Ig mice are used to raise human antibodies of the invention, such mice can be immunized with a purified or enriched preparation of Glypican-3 antigen and/or recombinant Glypican-3, or cells expressing Glypican-3, or a Glypican-3 fusion protein, as described by Lonberg, N. et al. (1994) *Nature* 368(6474): 856-859; Fishwild, D. et al. (1996) *Nature Biotechnology* 14: 845-851; and PCT Publication WO 98/24884 and WO 01/14424. Preferably, the mice will be 6-16 weeks of age upon the first infusion. For example, a purified or recombinant preparation (5-50 μg) of Glypican-3 antigen can be used to immunize the human Ig mice intraperitoneally.

Detailed procedures to generate fully human monoclonal antibodies to Glypican-3 are described in Example 1 below. Cumulative experience with various antigens has shown that the transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA (as described below), and mice with sufficient titers of anti-Glypican-3 human immunoglobulin can be used for fusions. Mice can be boosted intravenously with antigen 3 days before sacrifice and removal of the spleen. It is expected that 2-3 fusions for each immunization may need to be performed. Between 6 and 24 mice are typically immunized for each antigen. In one embodiment, mouse strains bearing an HCo7, HCo12 or HCo17 human heavy chain transgene strains may used. Alternatively or additionally, the KM Mouse® strain can be used. In addition, two or more of these strains can be bred together into a single mouse having a plurality of different human heavy chain transgenes.

Generation of Hybridomas Producing Human Monoclonal Antibodies

To generate hybridomas producing human monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3×63-Ag8.653 nonsecreting mouse myeloma cells (ATCC, CRL 1580) with 50% PEG. Alternatively, the single cell suspension of splenic lymphocytes from immunized mice can be fused using an electric field based electrofusion method, using a CytoPulse large chamber cell fusion electroporator (CytoPulse Sciences, Inc., Glen Burnie Md.). Cells are plated at approximately $2\times10^5$ in flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

Generation of Transfectomas Producing Monoclonal Antibodies

Antibodies of the invention also can be produced in a host cell transfectoma using, for example, a combination of recombinant DNA techniques and gene transfection methods as is well known in the art (e.g., Morrison, S. (1985) Science 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_K$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. *Methods in Enzymology* 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe, Y. et al. (1988) *Mol. Cell. Biol.* 8:466-472).

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr– host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) Immunology Today 6:12-13).

Preferred mammalian host cells for expressing the recombinant antibodies of the invention include Chinese Hamster Ovary (CHO cells) (including dhfr$^-$ CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *J. Mol. Biol.* 159:601-621), NSO myeloma cells, COS cells and SP2 cells. In particular, for use with NSO myeloma cells, another preferred expression system is the GS gene expression system disclosed in WO 87/04462 (to Wilson), WO 89/01036 (to Bebbington) and EP 338,841 (to Bebbington). When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Characterization of Antibody Binding to Antigen

Antibodies of the invention can be tested for binding to Glypican-3 by, for example, standard ELISA. Briefly, microtiter plates are coated with purified Glypican-3 at 0.25 μg/ml in PBS, and then blocked with 5% bovine serum albumin in PBS. Dilutions of antibody (e.g., dilutions of plasma from Glypican-3-immunized mice) are added to each well and incubated for 1-2 hours at 37° C. The plates are washed with PBS/Tween and then incubated with secondary reagent (e.g., for human antibodies, a goat-anti-human IgG Fc-specific polyclonal reagent) conjugated to alkaline phosphatase for 1 hour at 37° C. After washing, the plates are developed with pNPP substrate (1 mg/ml), and analyzed at OD of 405-650. Preferably, mice which develop the highest titers will be used for fusions.

An ELISA assay as described above can also be used to screen for hybridomas that show positive reactivity with a Glypican-3 immunogen. Hybridomas that bind with high avidity to Glypican-3 are subcloned and further characterized. One clone from each hybridoma, which retains the reactivity of the parent cells (by ELISA), can be chosen for making a 5-10 vial cell bank stored at −140° C., and for antibody purification.

To purify anti-Glypican-3 antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

To determine if the selected anti-Glypican-3 monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using Glypican-3 coated-ELISA plates as described above. Biotinylated mAb binding can be detected with a strep-avidin-alkaline phosphatase probe.

To determine the isotype of purified antibodies, isotype ELISAs can be performed using reagents specific for antibodies of a particular isotype. For example, to determine the isotype of a human monoclonal antibody, wells of microtiter plates can be coated with 1 μg/ml of anti-human immunoglobulin overnight at 4° C. After blocking with 1% BSA, the plates are reacted with 1 μg/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

Anti-Glypican-3 human IgGs can be further tested for reactivity with Glypican-3 antigen by Western blotting. Briefly, Glypican-3 can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

The binding specificity of an antibody of the invention may also be determined by monitoring binding of the antibody to cells expressing Glypican-3, for example by flow cytometry. Typically, a cell line, such as a CHO cell line, may be transfected with an expression vector encoding a transmembrane form of Glypican-3. The transfected protein may comprise a tag, such as a myc-tag, preferably at the N-terminus, for detection using an antibody to the tag. Binding of an antibody of the invention to Glypican-3 may be determined by incubating the transfected cells with the antibody, and detecting bound antibody. Binding of an antibody to the tag on the transfected protein may be used as a positive control.

The specificity of an antibody of the invention for Glypican-3 may be further studied by determining whether or not the antibody binds to other proteins (e.g. Glypican-1, Glypican-2, Glypican-4 or Glypican-6) or to Glypican-3 itself using the same methods by which binding to Glypican-3 is determined.

Immunoconjugates

In another aspect, the present invention features an anti-Glypican-3 antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). Other preferred examples of therapeutic cytotoxins that can be conjugated to an antibody of the invention include duocarmycins, calicheamicins, maytansines and auristatins, and derivatives thereof. An example of a calicheamicin antibody conjugate is commercially available (Mylotarg®; American Home Products).

Cytotoxins can be conjugated to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

Examples of cytotoxins are described, for example, in U.S. Pat. Nos. 6,989,452, 7,087,600, and 7,129,261, and in PCT Application Nos. PCT/US02/17210, PCT/US2005/017804, PCT/US06/37793, PCT/US06/060050, PCT/US2006/060711, WO/2006/110476, and in U.S. Patent Application No. 60/891,028, all of which are incorporated herein by reference in their entirety. For further discussion of types of cytotoxins, linkers and methods for conjugating therapeutic agents to antibodies, see also Saito, G. et al. (2003) *Adv. Drug Deliv. Rev.* 55:199-215; Trail, P. A. et al. (2003) *Cancer Immunol. Immunother.* 52:328-337; Payne, G. (2003) *Cancer Cell* 3:207-212; Allen, T. M. (2002) *Nat. Rev. Cancer* 2:750-763; Pastan, I. and Kreitman, R. J. (2002) *Curr. Opin. Investig. Drugs* 3:1089-1091; Senter, P. D. and Springer, C. J. (2001) *Adv. Drug Deliv. Rev.* 53:247-264.

Antibodies of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$ and lutetium$^{177}$. Method for preparing radioimmunconjugates are established in the art. Examples of radioimmunoconjugates are commercially available, including Zevalin® (IDEC Pharmaceuticals) and Bexxar® (Corixa Pharmaceuticals), and similar methods can be used to prepare radioimmunoconjugates using the antibodies of the invention.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy," in Monoclonal Antibodies And Cancer Therapy, Reisfeld et al. (eds.), pp. 243-56 (Alan R. Liss, Inc. 1985); Hellstrom et al., "Antibodies For Drug Delivery," in Controlled Drug Delivery ($2^{nd}$ Ed.), Robinson et al. (eds.), pp. 623-53 (Marcel Dekker, Inc. 1987); Thorpe, "Antibody Carriers Of Cytotoxic Agents In Cancer Therapy: A Review," in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy," in Monoclonal Antibodies For Cancer Detection And Therapy, Baldwin et al. (eds.), pp. 303-16 (Academic Press 1985), and Thorpe et al., *Immunol. Rev.,* 62:119-58 (1982).

Bispecific Molecules

In another aspect, the present invention features bispecific molecules comprising an anti-Glypican-3 antibody, or a fragment thereof, of the invention. An antibody of the invention, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for Glypican-3 and a second binding specificity for a second target epitope. In a particular embodiment of the invention, the second target epitope is an Fc receptor, e.g., human FcγRI (CD64) or a human Fca receptor (CD89). Therefore, the invention includes bispecific molecules capable of binding both to Fc7R or FcαR expressing effector cells (e.g., monocytes, macrophages or polymorphonuclear cells (PMNs)), and to target cells expressing Glypican-3. These bispecific molecules target Glypican-3 expressing cells to effector cell and trigger Fc receptor-mediated effector cell activities, such as phagocytosis of a Glypican-3 expressing cells, antibody dependent cell-mediated cytotoxicity (ADCC), cytokine release, or generation of superoxide anion.

In an embodiment of the invention in which the bispecific molecule is multispecific, the molecule can further include a third binding specificity, in addition to an anti-Fc binding specificity and an anti-Glypican-3 binding specificity. In one embodiment, the third binding specificity is an anti-enhancement factor (EF) portion, e.g., a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor, and thereby results in an enhancement of the effect of the binding determinants for the Fc receptor or target cell antigen. The "anti-enhancement factor portion" can bind an Fc receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g. via CD2, CD3, CD8, CD28, CD4, CD40, ICAM-1 or other immune cell that results in an increased immune response against the target cell).

In one embodiment, the bispecific molecules of the invention comprise as a binding specificity at least one antibody, or an antibody fragment thereof, including, e.g., an Fab, Fab', $F(ab')_2$, Fv, Fd, dAb or a single chain Fv. The antibody may also be a light chain or heavy chain dimer, or any minimal fragment thereof such as a Fv or a single chain construct as described in U.S. Pat. No. 4,946,778 to Ladner et al., the contents of which is expressly incorporated by reference.

In one embodiment, the binding specificity for an Fcγ receptor is provided by a monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγreceptor classes: FcγRI (CD64), FcγRII (CD32), and FcγRIII (CD16). In one preferred embodiment, the Fcγ receptor a human high affinity FcγRI. The human FcγRI is a 72 kDa molecule, which shows high affinity for monomeric IgG ($10^8$-$10^9$ $M^{-1}$).

The production and characterization of certain preferred anti-Fcγ monoclonal antibodies are described in PCT Publication WO 88/00052 and in U.S. Pat. No. 4,954,617 to Fanger et al., the teachings of which are fully incorporated by reference herein. These antibodies bind to an epitope of FcγRI, FcγRII or FcγRIII at a site which is distinct from the Fc7 binding site of the receptor and, thus, their binding is not blocked substantially by physiological levels of IgG. Specific anti-FcγRI antibodies useful in this invention are mAb 22, mAb 32, mAb 44, mAb 62 and mAb 197. The hybridoma producing mAb 32 is available from the American Type Culture Collection, ATCC Accession No. HB9469. In other embodiments, the anti-Fcγ receptor antibody is a humanized form of monoclonal antibody 22 (H22). The production and characterization of the H22 antibody is described in Graziano, R. F. et al. (1995) *J. Immunol.* 155 (10): 4996-5002 and PCT Publication WO 94/10332 to Tempest et al. The H22 antibody producing cell line was deposited at the American Type Culture Collection under the designation HA022CL1 and has the accession no. CRL 11177.

In still other preferred embodiments, the binding specificity for an Fc receptor is provided by an antibody that binds to a human IgA receptor, e.g., an Fc-alpha receptor (FcαRI (CD89)), the binding of which is preferably not blocked by human immunoglobulin A (IgA). The term "IgA receptor" is intended to include the gene product of one α-gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity ($\approx 5\times10^7$ $M^{-1}$) for both IgA1 and IgA2, which is increased upon exposure to cytokines such as G-CSF or GM-CSF (Morton, H. C. et al. (1996) Critical Reviews in *Immunology* 16:423-440). Four FcαRI-specific monoclonal antibodies, identified as A3, A59, A62 and A77, which bind FcαRI outside the IgA ligand binding domain, have been described (Monteiro, R. C. et al. (1992) *J. Immunol.* 148: 1764).

FcαRI and FcγRI are preferred trigger receptors for use in the bispecific molecules of the invention because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g., ADCC, phagocytosis); and (4) mediate enhanced antigen presentation of antigens, including self-antigens, targeted to them.

While human monoclonal antibodies are preferred, other antibodies which can be employed in the bispecific molecules of the invention are murine, chimeric and humanized monoclonal antibodies.

The bispecific molecules of the present invention can be prepared by conjugating the constituent binding specificities, e.g., the anti-FcR and anti-Glypican-3 binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis(2-nitrobenzoic acid) (DTNB), o-phenylenedimaleimide (oPDM), N-succinimidyl-3-(2-pyridyldithio) propionate (SPDP), and sulfosuccinimidyl 4-(N-maleimidomethyl)cyclohaxane-1-carboxylate (sulfo-SMCC) (see e.g., Karpovsky et al. (1984) *J. Exp. Med.* 160: 1686; Liu, M A et al. (1985) *Proc. Natl. Acad. Sci. USA* 82:8648). Other methods include those described in Paulus (1985) Behring Ins. Mitt. No. 78, 118-132; Brennan et al. (1985) *Science* 229:81-83, and Glennie et al. (1987) *J. Immunol.* 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand× Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858, all of which are expressly incorporated herein by reference.

Binding of the bispecific molecules to their specific targets can be confirmed by, for example, enzyme-linked immunosorbant assay (ELISA), radioimmunoas say (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoas say (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

Pharmaceutical Compositions

In another aspect, the present invention provides a composition, e.g., a pharmaceutical composition, containing one or a combination of monoclonal antibodies, or antigen-binding portion(s) thereof, of the present invention, formulated together with a pharmaceutically acceptable carrier. Such compositions may include one or a combination of (e.g., two or more different) antibodies, or immunoconjugates or bispecific molecules of the invention. For example, a pharmaceutical composition of the invention can comprise a combination of antibodies (or immunoconjugates or bispecifics) that bind to different epitopes on the target antigen or that have complementary activities.

Pharmaceutical compositions of the invention also can be administered in combination therapy, i.e., combined with other agents. For example, the combination therapy can include an anti-Glypican-3 antibody of the present invention combined with at least one other anti-inflammatory or immunosuppressant agent. Examples of therapeutic agents that can be used in combination therapy are described in greater detail below in the section on uses of the antibodies of the invention.

As used herein, “pharmaceutically acceptable carrier” includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, may be coated in a material to protect the compound from the action of acids and other natural conditions that may inactivate the compound.

The pharmaceutical compounds of the invention may include one or more pharmaceutically acceptable salts. A “pharmaceutically acceptable salt” refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-Glypican-3 antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three monthgs or yearly. Intervals can also be irregular as indicated by measuring blood levels of antibody to the target antigen in the patient. In some methods, dosage is adjusted to achieve a plasma antibody concentration of about 1-1000 μg/ml and in some methods about 25-300 μg/ml.

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-Glypican-3 antibody of the invention preferably results in a decrease in severity of disease symptoms, an increase in frequency and duration of disease symptom-free periods, or a prevention of impairment or disability due to the disease affliction. For example, for the treatment of Glypican-$3^+$ tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit cell growth, such inhibition can be measured in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Preferred routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p120 (Schreier et al. (1994) J. Biol. Chem. 269:9090); see also K. Keinanen; M. L. Laukkanen (1994) *FEBS Lett.* 346:123; J. J. Killion; I. J. Fidler (1994) *Immunomethods* 4:273.

Uses and Methods

The antibodies, particularly the human antibodies, antibody compositions and methods of the present invention have numerous in vitro and in vivo diagnostic and therapeutic utilities involving the diagnosis and treatment of Glypican-3 mediated disorders. For example, these molecules can be administered to cells in culture, in vitro or ex vivo, or to human subjects, e.g., in vivo, to treat, prevent and to diagnose a variety of disorders. As used herein, the term "subject" is intended to include human and non-human animals. Non-human animals include all vertebrates, e.g., mammals and non-mammals, such as non-human primates, sheep, dogs, cats, cows, horses, chickens, amphibians, and reptiles. Preferred subjects include human patients having disorders mediated by Glypican-3 activity. The methods are particularly suitable for treating human patients having a disorder associated with aberrant Glypican-3 expression. When antibodies to Glypican-3 are administered together with another agent, the two can be administered in either order or simultaneously.

Given the specific binding of the antibodies of the invention for Glypican-3, the antibodies of the invention can be used to specifically detect Glypican-3 expression on the surface of cells and, moreover, can be used to purify Glypican-3 via immunoaffinity purification.

Furthermore, given the expression of Glypican-3 on various liver tumor cells, the human antibodies, antibody compositions and methods of the present invention can be used to treat a subject with a liver tumorigenic disorder, e.g., a disorder characterized by the presence of tumor cells expressing Glypican-3 including, for example, HCC cells.

In one embodiment, the antibodies (e.g., human monoclonal antibodies, multispecific and bispecific molecules and compositions) of the invention can be used to detect levels of Glypican-3, or levels of cells which contain Glypican-3 on their membrane surface, which levels can then be linked to certain disease symptoms. Alternatively, the antibodies can be used to inhibit or block Glypican-3 function which, in turn, can be linked to the prevention or amelioration of certain disease symptoms, thereby implicating Glypican-3 as a mediator of the disease. This can be achieved by contacting a sample and a control sample with the anti-Glypican-3 antibody under conditions that allow for the formation of a complex between the antibody and Glypican-3. Any complexes formed between the antibody and Glypican-3 are detected and compared in the sample and the control.

In another embodiment, the antibodies (e.g., human antibodies, multispecific and bispecific molecules and compositions) of the invention can be initially tested for binding activity associated with therapeutic or diagnostic use in vitro. For example, compositions of the invention can be tested using the flow cytometric assays described in the Examples below.

The antibodies (e.g., human antibodies, multispecific and bispecific molecules, immunoconjugates and compositions) of the invention have additional utility in therapy and diagnosis of Glypican-3-related diseases. For example, the human monoclonal antibodies, the multispecific or bispecific molecules and the immunoconjugates can be used to elicit in vivo or in vitro one or more of the following biological activities: to inhibit the growth of and/or kill a cell expressing Glypican-3; to mediate phagocytosis or ADCC of a cell expressing Glypican-3 in the presence of human effector cells, or to block a Glypican-3 ligand from binding to Glypican-3.

In a particular embodiment, the antibodies (e.g., human antibodies, multispecific and bispecific molecules and compositions) are used in vivo to treat, prevent or diagnose a variety of Glypican-3-related diseases. Examples of Glypican-3-related diseases include, among others, HCC and other liver cancers.

Suitable routes of administering the antibody compositions (e.g., human monoclonal antibodies, multispecific and bispecific molecules and immunoconjugates) of the invention in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

As previously described, human anti-Glypican-3 antibodies of the invention can be co-administered with one or other more therapeutic agents, e.g., a cytotoxic agent, a radiotoxic agent or an immunosuppressive agent. The antibody can be linked to the agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, and cyclophosphamide hydroxyurea which, by themselves, are only effective at levels which are toxic or subtoxic to a patient. Cisplatin is intravenously administered as a 100 mg/kg dose once every four weeks and adriamycin is intravenously administered as a 60-75 mg/ml dose once every 21 days. Co-administration of the human anti-Glypican-3 antibodies, or antigen binding fragments thereof, of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Target-specific effector cells, e.g., effector cells linked to compositions (e.g., human antibodies, multispecific and bispecific molecules) of the invention can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells can be administered as a suspension of cells in a physiologically acceptable solution. The number of cells administered can be in the order of $10^8$-$10^9$ but will vary depending on the therapeutic purpose. In general, the amount will be sufficient to obtain localization at the target cell, e.g., a tumor cell expressing Glypican-3, and to affect cell killing by, e.g., phagocytosis. Routes of administration can also vary.

Therapy with target-specific effector cells can be performed in conjunction with other techniques for removal of targeted cells. For example, anti-tumor therapy using the compositions (e.g., human antibodies, multispecific and bispecific molecules) of the invention and/or effector cells armed with these compositions can be used in conjunction with chemotherapy. Additionally, combination immunotherapy may be used to direct two distinct cytotoxic effector populations toward tumor cell rejection. For example, anti-Glypican-3 antibodies linked to anti-Fc-gamma R1 or anti-CD3 may be used in conjunction with IgG- or IgA-receptor specific binding agents.

Bispecific and multispecific molecules of the invention can also be used to modulate FcγR or FcγR levels on effector cells, such as by capping and elimination of receptors on the cell surface. Mixtures of anti-Fc receptors can also be used for this purpose.

The compositions (e.g., human, humanized, or chimeric antibodies, multispecific and bispecific molecules and immunoconjugates) of the invention which have complement binding sites, such as portions from IgG1, -2, or -3 or IgM which bind complement, can also be used in the presence of complement. In one embodiment, ex vivo treatment of a population of cells comprising target cells with a binding agent of the invention and appropriate effector cells can be supplemented by the addition of complement or serum containing complement. Phagocytosis of target cells coated with a binding agent of the invention can be improved by binding of complement proteins. In another embodiment target cells coated with the compositions (e.g., human antibodies, multispecific and bispecific molecules) of the invention can also be lysed by complement. In yet another embodiment, the compositions of the invention do not activate complement.

The compositions (e.g., human, humanized, or chimeric antibodies, multispecific and bispecific molecules and immunoconjugates) of the invention can also be administered together with complement. In certain embodiments, the instant disclosure provides compositions comprising human antibodies, multispecific or bispecific molecules and serum or complement. These compositions can be advantageous when the complement is located in close proximity to the human antibodies, multispecific or bispecific molecules. Alternatively, the human antibodies, multispecific or bispecific molecules of the invention and the complement or serum can be administered separately.

Also within the scope of the present invention are kits comprising the antibody compositions of the invention (e.g., human antibodies, bispecific or multispecific molecules, or immunoconjugates) and instructions for use. The kit can further contain one or more additional reagents, such as an immunosuppressive reagent, a cytotoxic agent or a radiotoxic agent, or one or more additional human antibodies of the invention (e.g., a human antibody having a complementary activity which binds to an epitope in the Glypican-3 antigen distinct from the first human antibody).

Accordingly, patients treated with antibody compositions of the invention can be additionally administered (prior to, simultaneously with, or following administration of a human antibody of the invention) with another therapeutic agent, such as a cytotoxic or radiotoxic agent, which enhances or augments the therapeutic effect of the human antibodies.

In other embodiments, the subject can be additionally treated with an agent that modulates, e.g., enhances or inhibits, the expression or activity of Fcγ or Fcγ receptors by, for example, treating the subject with a cytokine. Preferred cytokines for administration during treatment with the multispecific molecule include of granulocyte colony-stimulating factor (G-CSF), granulocyte-macrophage colony-stimulating factor (GM-CSF), interferon-γ (IFN-γ), and tumor necrosis factor (TNF).

The compositions (e.g., human antibodies, multispecific and bispecific molecules) of the invention can also be used to target cells expressing FcγR or Glypican-3, for example for labeling such cells. For such use, the binding agent can be linked to a molecule that can be detected. Thus, the invention provides methods for localizing ex vivo or in vitro cells expressing Fc receptors, such as FcγR, or Glypican-3. The detectable label can be, e.g., a radioisotope, a fluorescent compound, an enzyme, or an enzyme co-factor.

In a particular embodiment, the invention provides methods for detecting the presence of Glypican-3 antigen in a sample, or measuring the amount of Glypican-3 antigen, comprising contacting the sample, and a control sample, with a human monoclonal antibody, or an antigen binding portion thereof, which specifically binds to Glypican-3, under conditions that allow for formation of a complex between the antibody or portion thereof and Glypican-3. The formation of a complex is then detected, wherein a difference complex formation between the sample compared to the control sample is indicative the presence of Glypican-3 antigen in the sample.

In other embodiments, the invention provides methods for treating a Glypican-3 mediated disorder in a subject, e.g., HCC and other liver cancers.

In yet another embodiment, immunoconjugates of the invention can be used to target compounds (e.g., therapeutic agents, labels, cytotoxins, radiotoxoins immunosuppressants, etc.) to cells which have Glypican-3 cell surface receptors by linking such compounds to the antibody. For example, an anti-Glypican-3 antibody can be conjugated to any of the toxin compounds described in U.S. Pat. Nos. 6,281,354 and 6,548,530, US patent publication Nos. 20030050331, 20030064984, 20030073852, and 20040087497, or published in WO 03/022806. Thus, the invention also provides methods for localizing ex vivo or in vivo cells expressing Glypican-3 (e.g., with a detectable label, such as a radioisotope, a fluorescent compound, an enzyme, or an enzyme co-factor). Alternatively, the immunoconjugates can be used to kill cells which have Glypican-3 cell surface receptors by targeting cytotoxins or radiotoxins to Glypican-3.

The present invention is further illustrated by the following examples which should not be construed as further limiting. The contents of all figures and all references, patents and published patent applications cited throughout this application are expressly incorporated herein by reference.

EXAMPLES

Example 1

Generation of Human Monoclonal Antibodies Against Glypican-3 Antigen

A recombinant fusion protein, Glypican-3-his, was created that comprises the extracellular domain of the Glypican-3 protein linked to a non-Glypican-3 polypeptide, a histidine tag. Glypican-3-his was generated by standard recombinant methods and used as an antigen for immunization. In addition, CHO cells transfected with a Glypican-3-Myc expression construct and a cell line, Hep-G2, were used as antigens for immunization.

Transgenic HuMAb Mouse® and KM Mouse®

Fully human monoclonal antibodies to Glypican-3 were prepared using an HCo17 strain of the transgenic HuMAb Mouse® and the KM strain of transgenic transchromosomic mice, each of which express human antibody genes. The HCo17 strain was constructed as described in WO/2005/058815, which is incorporated herein by reference in its entirety. The KM strain was constructed as described in WO 02/43478, which is incorporated herein by reference in its entirety.

HuMab Mouse and KM Mouse Immunizations

To generate fully human monoclonal antibodies to Glypican-3, mice of the HuMAb Mouse® and KM Mouse® were immunized with Glypican-3-his protein expressed in CHO—S cells, CHO cells expressing the Glypicn-3-Myc protein, and Hep-G2 cells. General immunization schemes for the HuMAb Mouse® are described in Lonberg, N. et al (1994) *Nature* 368(6474): 856-859; Fishwild, D. et al. (1996) Nature *Biotechnology* 14: 845-851 and PCT Publication WO 98/24884. The mice were 6-16 weeks of age upon the first infusion of antigen. A purified recombinant preparation (5-25 μg) of Glypican-3 fusion protein or Glypican-3 expression cells ($1\times10^7$ cells) were used to immunize each HuMab Mouse® and KM Mouse®.

Transgenic mice were immunized with antigen in complete Freund's adjuvant or Ribi adjuvant either intraperitonealy (IP), subcutaneously (Sc) or via footpad (FP), followed by 3-21 days IP, Sc or FP immunization (up to a total of 12 immunizations) with the antigen in incomplete Freund's or Ribi adjuvant. The immune response was monitored by retroorbital bleeds. The plasma was screened by ELISA (as described below) and FACS, and mice with sufficient titers of anti-Glypican-3 human immunoglobulin were used for fusions. Mice were boosted intravenously with antigen 3 and 2 days before sacrifice and removal of the spleen. As is typical, between ten and 35 fusions for each antigen were performed. Several dozen mice were immunized for each antigen.

Selection of a HuMab Mouse® or KM Mouse® Producing Anti-Glypican-3 Antibodies

To select a HuMab Mouse® or a KM Mouse® producing antibodies that bound Glypican-3, sera from immunized mice was tested by ELISA as described by Fishwild, D. et al. (1996)(supra). Briefly, microtiter plates were coated with purified recombinant Glypican-3 at 1-2 μg/ml in PBS, 50 μl/wells incubated 4° C. overnight then blocked with 200 μl/well of 5% chicken serum in PBS/Tween (0.05%). Dilutions of plasma from Glypican-3-immunized mice were added to each well and incubated for 1-2 hours at ambient temperature. The plates were washed with PBS/Tween and then incubated with a goat-anti-human IgG Fc polyclonal antibody conjugated with horseradish peroxidase (HRP) for 1 hour at room temperature. After washing, the plates were developed with ABTS substrate (Sigma, A-1888, 0.22 mg/ml) and analyzed by spectrophotometer at OD 415-495.

Sera from immunized mice were then further screened by flow cytometry for binding to a cell line expressing recombinant human Glypican-3, but not to a control cell line that does not express Glypican-3. Briefly, the binding of anti-Glypican-3 antibodies was assessed by incubating Glypican-3-expressing CHO cells with the anti-Glypican-3 antibody at a 1:20 dilution. The cells were washed and binding was detected with a FITC-labeled anti-human IgG Ab. Flow cytometric analyses were performed using a FACScan flow cytometry (Becton Dickinson, San Jose, Calif.). Mice that developed the highest titers of anti-Glypican-3 antibodies were used for fusions. Fusions were performed as described below and hybridoma supernatants were tested for anti-Glypican-3 activity by ELISA and FACS.

Generation of Hybridomas Producing Human Monoclonal Antibodies to Glypican-3:

The mouse splenocytes, isolated from a HuMab Mouse® or a KM Mouse®, were fused using electric field based electrofusion using a Cyto Pulse large chamber cull fusion electroporator (Cyto Pulse Sciences, Inc., Glen Burnie, Md.). The resulting hybridomas were then screened for the production of antigen-specific antibodies. Single cell suspensions of splenic lymphocytes from immunized mice were fused with SP2/0 nonsecreting mouse myeloma cells (ATCC, CRL 1581) using electric field based electrofusion using a Cyto Pulse large chamber cull fusion electroporator (Cyto Pulse Sciences, Inc., Glen Burnie, Md.). Cells were plated at approximately $1\times10^4$ cells/well in flat bottom microtiter plates, followed by about two week incubation in selective medium containing 10% fetal bovine serum, 10% P388D1 (ATCC, CRL TIB-63) conditioned medium, 3-5% origen (IGEN) in DMEM (Mediatech, CRL 10013, with high glucose, L-glutamine and sodium pyruvate) plus 5 mM HEPES, 0.055 mM 2-mercaptoethanol, 50 mg/ml gentamycin and 1×HAT (Sigma, CRL P-7185). After 1-2 weeks, cells were cultured in medium in which the HAT was replaced with HT. Individual wells were then screened by ELISA and FACS (described above) for human anti-Glypican-3 monoclonal IgG antibodies. Once extensive hybridoma growth occurred, medium was monitored usually after 10-14 days. The antibody secreting hybridomas were replated, screened again and, if still positive for human IgG, anti-Glypican-3 monoclonal antibodies were subcloned at least twice by limiting dilution. The stable subclones were then cultured in vitro to generate small amounts of antibody in tissue culture medium for further characterization.

Hybridoma clones 4A6, 11E7, AND 16D10, generated from a HuMAb Mouse®, were selected for further analysis.

Example 2

Structural Characterization of Human Monoclonal Antibodies 4A6, 11E7, and 16D10

The cDNA sequences encoding the heavy and light chain variable regions of the 4A6, 11E7, and 16D10 monoclonal antibodies were obtained from the 4A6, 11E7, and 16D10 hybridomas, respectively, using standard PCR techniques and were sequenced using standard DNA sequencing techniques.

The nucleotide and amino acid sequences of the heavy chain variable region of 4A6 are shown in FIG. 1A and in SEQ ID NO:25 and 19, respectively.

The nucleotide and amino acid sequences of the light chain variable region of 4A6 are shown in FIG. 1B and in SEQ ID NO:28 and 22, respectively.

Comparison of the 4A6 heavy chain immunoglobulin sequence to the known human germline immunoglobulin heavy chain sequences demonstrated that the 4A6 heavy chain utilizes a $V_H$ segment from human germline $V_H$ 5-51 and a $J_H$ segment from human germline JH4b. The alignment of the 4A6 $V_H$ sequence to the germline $V_H$ 5-51 sequence is shown in FIG. 4. Further analysis of the 4A6 $V_H$ sequence using the Kabat system of CDR region determination led to the delineation of the heavy chain CDR1, CDR2 and CD3 regions as shown in FIGS. 1A and 4, and in SEQ ID NOs:1, 4 and 7, respectively.

Comparison of the 4A6 light chain immunoglobulin sequence to the known human germline immunoglobulin light chain sequences demonstrated that the 4A6 light chain utilizes a $V_L$ segment from human germline $V_K$ A27 and a $J_K$ segment from human germline JK4. The alignment of the 4A6 $V_L$ sequence to the germline $V_K$ A27 sequence is shown in FIG. 7. Further analysis of the 4A6 $V_L$ sequence using the Kabat system of CDR region determination led to the delineation of the light chain CDR1, CDR2 and CD3 regions as shown in FIGS. 1B and 7, and in SEQ ID NOs:10, 13, and 16, respectively.

The nucleotide and amino acid sequences of the heavy chain variable region of 11E7 are shown in FIG. 2A and in SEQ ID NO:26 and 20, respectively.

The nucleotide and amino acid sequences of the light chain variable region of 11E7 are shown in FIG. 2B and in SEQ ID NO:29 and 23, respectively.

Comparison of the 11E7 heavy chain immunoglobulin sequence to the known human germline immunoglobulin heavy chain sequences demonstrated that the 11E7 heavy chain utilizes a $V_H$ segment from human germline $V_H$ 5-51 and a $J_H$ segment from human germline JH4b. The alignment of the 11E7 $V_H$ sequence to the germline $V_H$ 5-51 sequence is shown in FIG. 5. Further analysis of the 11E7 $V_H$ sequence using the Kabat system of CDR region determination led to the delineation of the heavy chain CDR1, CDR2 and CD3 regions as shown in FIGS. 2A and 5, and in SEQ ID NOs:2, 5, and 8, respectively.

Comparison of the 11E7 light chain immunoglobulin sequence to the known human germline immunoglobulin light chain sequences demonstrated that the 11E7 light chain utilizes a $V_L$ segment from human germline $V_K$ A27 and a $J_K$ segment from human germline JK4. The alignment of the 11E7 $V_L$ sequence to the germline $V_K$ A27 sequence is shown in FIG. 8. Further analysis of the 11E7 $V_L$ sequence using the Kabat system of CDR region determination led to the delineation of the light chain CDR1, CDR2 and CD3 regions as shown in FIGS. 2B and 8, and in SEQ ID NOs:11, 14, and 17, respectively.

The nucleotide and amino acid sequences of the heavy chain variable region of 16D10 are shown in FIG. 3A and in SEQ ID NO:27 and 21, respectively.

The nucleotide and amino acid sequences of the light chain variable region of 16D10 are shown in FIG. 3B and in SEQ ID NO:30 and 24, respectively.

Comparison of the 16D10 heavy chain immunoglobulin sequence to the known human germline immunoglobulin heavy chain sequences demonstrated that the 16D10 heavy chain utilizes a $V_H$ segment from human germline $V_H$ 5-51 and a $J_H$ segment from human germline JH4b. The alignment of the 16D10 $V_H$ sequence to the germline $V_H$ 5-51 sequence is shown in FIG. 6. Further analysis of the 16D10 $V_H$ sequence using the Kabat system of CDR region determination led to the delineation of the heavy chain CDR1, CDR2 and CD3 regions as shown in FIGS. 3A and 6, and in SEQ ID NOs:3, 6, and 9, respectively.

Comparison of the 16D10 light chain immunoglobulin sequence to the known human germline immunoglobulin light chain sequences demonstrated that the 16D10 light chain utilizes a $V_L$ segment from human germline $V_K$ A27 and a $J_K$ segment from human germline JK1. The alignment of the 16D10 $V_L$ sequence to the germline $V_K$ A27 sequence is shown in FIG. 9. Further analysis of the 16D10 $V_L$ sequence using the Kabat system of CDR region determination led to the delineation of the light chain CDR1, CDR2 and CD3 regions as shown in FIGS. 3B and 9, and in SEQ ID NOs:12, 15, and 18, respectively.

Example 3

Characterization of Binding Specificity and Binding Kinetics of Anti-Glypican-3 Human Monoclonal Antibodies In this example, binding affinity, kinetics and specificity of anti-Glypican-3 antibodies were examined by Biacore analysis and flow cytometry.

Binding Affinity and Kinetics

Anti-Glypican-3 antibodies were characterized for affinities and binding kinetics by Biacore analysis (Biacore AB, Uppsala, Sweden). Glypican-3 was covalently linked to a CM5 chip (carboxymethyl dextran coated chip) via primary amines, using standard amine coupling chemistry and kit provided by Biacore. Binding was measured by flowing a concentration series of the anti-Glypican-3 monoclonal antibodies in HBS-EP buffer (provided by Biacore AB) at 20, 10, 5, 2.5 and 1.25 μg/ml at a flow rate of 40 μL/min. Background binding was accounted for by flowing a concentration series of IgG1 across the same chip. The antigen-antibody association kinetics were followed for 3 minutes and the dissociation kinetics were followed for 10 minutes. The association and dissociation curves were fit to a 1:1 Langmuir binding model using BIAevaluation software (Biacore AB). The $K_D$, $k_{on}$ and $k_{off}$ values that were determined are shown in Table 1.

TABLE 1

Biacore binding data for anti-Glypican-3 monoclonal antibodies

| Anti-Glypican-3 antibody | Affinity $K_D$ $\times 10^{-9}$ (M) | On rate $k_{on}$ $\times 10^{6}$ (1/Ms) | Off rate $k_{off}$ $\times 10^{-4}$ 1/s |
|---|---|---|---|
| 4A6 | 0.20 | 1.6 | 3.2 |
| 16D10 | 0.31 | 1.8 | 5.4 |
| 11E7 | 0.40 | 1.8 | 7.3 |

Binding Affinity Measured by FACS

Anti-Glypican-3 antibodies were shown to bind to cell-surface Glypican-3 proteins with a high affinity using a fluorescence activated cell sorter ("FACS") assay. The HCC cell line Hep-3B was added at a density of 2×105 cells into each well of 96-well plate. The 4A6, 11E7, and 16D10 monoclonal antibodies were added at a starting concentration of 20 ug/ml and serially diluting the antibody at a 1:3 dilution. The cells were washed and binding was detected with a FITC-labeled anti-human IgG Ab. Flow cytometric analyses were performed using a FACSCalibur flow cytometer (Becton Dickinson, San Jose, Calif.). The resulting binding affinities, plotted as the mean fluorescence intensity ("MFI"), is shown in FIG. 10. The binding affinities of the antibodies bound the HCC cells in a concentration-dependent manner. The effective concentration ("EC50") for each antibody was determined as the concentration that resulted in a 50% mean fluorescence intensity ("MFI"). In this example, the strongest binding affinity was observed with the 4A6 antibody, which showed a MFI of 0.83. The next best observed affinity was for 16D10, which had an EC50 of 1.39. The lowest observed affinity of the three antibodies was for 11E7, which had an EC50 of 1.98.

Binding Specificity Measured by FACS

Anti-Glypican-3 antibodies were shown to bind to cell-surface Glypican-3 proteins with a high specificity using a FACS assay. The HCC cell lines Hep-3B and Hep-G2 were grown in DMEM+10% FBS at a density of $1\times10^5$ cells. The 4A6, 11E7, and 16D10 monoclonal antibodies were added at a concentration of 10 μg/ml. Additionally, three negative controls were analyzed for comparison. These negative controls were (1) no stain at all, (2) the secondary antibody added alone, and (3) a $hIgG_1$ isotype control antibody. The cells were washed and binding was detected with a FITC-labeled anti-human IgG Ab. Flow cytometric analyses were performed using a FACSCalibur flow cytometer. FIG. 11 shows that the anti-Glypican-3 antibodies bound the HCC cells with a high affinity. In contrast, the negative control samples did not show any binding to the HCC cells.

Chinese hamster ovary (CHO) cell lines that stably express Glypican-3 on the cell surface were developed and used to determine the specificity of the Glypican-3 monoclonal antibodies by flow cytometry. CHO cells were transfected with expression plasmids containing full length cDNA encoding Glypican-3. Binding of the three anti-Glypican-3 monoclonal antibodies was assessed by incubating the transfected cells with each of the Glypican-3 antibodies at a concentration of 10 μg/ml. The cells were washed and binding was detected with a phycoerythrin-labeled anti-human IgG Ab (BD Biosciences). Secondary antibody alone was used as a negative control. The results are depicted in FIG. 12. The Glypican-3 monoclonal antibodies 4A6, 11E7, and 16D10 bound to the CHO cell line transfected with Glypican-3 but not to the parental CHO cell lines. These data demonstrate the specificity of the monoclonal antibodies for Glypican-3.

Epitope Binning of Anti Glypican-3 Monoclonal Antibodies by Biacore

Epitope binning was performed by Biacore analysis to determine whether the anti-Glypican-3 antibodies bind to overlapping epitopes. Antibodies that have overlapping epitopes will compete for binding to Glypican-3 whereas those with distinct epitopes will not compete and will simultaneously bind to the antigen. Purified 4A6 and 16D10 were immobilized at 4000 RU on a CM5 chip using a standard amine coupling protocol. Glypican-3-his (50 nM) was pre-incubated for at least 1 hour with the 4A6, 11E7, or 16D10 monoclonal antibodies prior to injection. The antibody concentrations were a two-fold dilution series starting at 400 nM. Antibody-antigen mixtures were injected at a flow rate 5 μl/min for 5 minutes. Each of the 4A6, 11E7, and 16D10 monoclonal antibodies were able to compete for binding to the immobilized 4A6 and 16D10 antibodies in a concentration-dependent manner. This shows that 4A6, 16D10, and 11E7 have overlapping epitopes.

Example 4

Glypican-3 Antibodies Bind to Liver Cancer Tissue

Anti-Glypican-3 monoclonal antibody 4A6 was shown to bind human liver cancer tissues. Biopsies from liver cancer patients were obtained and the antibodies used for immunohistochemistry staining (Cytomyx, Mass.). 5 μm tissues cores were used. After drying for 30 minutes on slides, the tissue sections were fixed with acetone at room temperature for 5 minutes. Slides were rinsed in PBS and then blocked with serum-free protein and peroxidase blocker (Dako S2001, CO) and subsequently incubated with primary antibody complex at 5 μg/ml for 45 minutes at room temperature. Next, the slides were washed and incubated for 30 minutes with FITC-conjugated secondary antibody (Jackson Immunoresearch Lab, 109-097-003) and washed again with PBS and incubated with polymer HRP conjugates (Dako, Colo., K4063) for 20 minutes. Chromogen (Dako K3464) was used as a substrate, resulting in brown staining. Slides were mounted in Faramount Aqueous Mounting Media (Dako, S3025). 4A6 was shown to bind specifically to liver tumor cells. As exemplified in FIG. 13, the 4A6 monoclonal antibody specifically stains cancerous liver tissue but not the surrounding normal tissue. When stained with the monoclonal antibodies, other organs exhibit negative or non-specific staining, which include uterus, lung, liver, kidney colon, cervix, breast, bone marrow, adrenal glands, cerebellum, cerebrum, esophagus, heart, prostate, placenta, pituitary, ovary, pancreas, mesothelia, salivary gland, tonsil, skin, small intestine, skeletal muscle, stomach, spleen, testis, thymus, and thyroid. The data demonstrates that anti-Gpc3 HuMab 4A6 recognizes Gcp3 expressed in liver tumors.

Example 5

Anti-Glypican-3 Antibody Activity

The monoclonal antibodies 4A6, 11E7, and 16D10 were shown to kill Gcp3 positive Hep-G2 cells in the presence of natural killer T-cells using an antibody-dependent cellular cytotoxicity ("ADCC") assay.

Human effector cells were prepared from whole blood as follows. Human peripheral blood mononuclear cells were purified from heparinized whole blood by standard Ficoll-paque separation. The cells are resuspended in RPMI 1640 media containing 10% FBS 200 U/ml of human IL-2 (PeproTech, N.J.) and incubated overnight at 37 C. The following day, the cells are collected and washed twice in RPMI+1% of BSA (assay media) and resuspended at 1×10e6/ml.

100 μl of target cells at 1×10e4/well in flat bottom 96-well plate were incubated in assay media overnight at 37 C. Following the target cells washed twice in assay media, 100 ul of assay media was added into each well and incubated with 50 ul of the effector cells and 50 ul of either anti-Gpc3 antibodies or human IgG1 as isotype control at final concentration of 10 ug/ml. The Gpc3+Hep-G2 cell line was tested for antibody specific ADCC to anti-Gpc3 antibodies using Takara LDH cytotoxicity detection kit (Roche, 04744 926001, Switzerland), a fluorescence emission analysis as follows. The target cell line, Hep-G2 was incubated with effector cells at a target to effector ratio of 1:50. After 18 hour incubation at 37 C, 100 ul of the supernatants were collected and transferred to a new flat bottom 96-well plate. 100 ul of Solution C was added to each well and incubated at room temperature for 30 minutes. Absorbance of the samples at 490 nM was measured by SPECTRAMAX 340 PC (MTX Lab System, VA). The % lysis was determined by calculating the average absorbance of the triplicates and subtracting the background.

As can be seen in FIG. 14, the 4A6, 11E7, and 16D10 monoclonal antibodies each cause specific lysis of the Hep-3b cells by natural killer T-cells as compared to the hIgG1 isotype control antibody.

Example 6

Anti-Glypican-3 Antibody Internalization

The monoclonal antibodies 4A6, 11E7, and 16D10 were shown to be internalized by Hep-3b cells upon binding to the cells using a Hum-Zap assay. The Hum-ZAP assay showed internalization of the anti-Glypican-3 monoclonal antibodies through binding of an anti-human IgG secondary antibody conjugated to the toxin saporin. (Advanced Targeting System, San Diego, Calif., IT-22-100). First, 4A6, 11E7, and 16D10 were bound to the surface of the Hep-3B cells. Then, the Hum-ZAP antibodies were bound to the primary antibodies. Next, the primary antibody/Hum-ZAP complex was internalized by the cells. The entrance of Saporin into the cells resulted in protein synthesis inhibition and eventual cell death.

The Hum-ZAP assay was conducted as follows. Each of the cells was seeded at a density of $3\times10^3$ cells per well. The anti-Glypican-3 monoclonal antibodies or an isotype control human IgG were serially diluted then added to the cells. The Hum-ZAP was then added at a concentration of 2 μg/ml and the plates allowed to incubate for 96 hours. Cell viability in the plates was detected by CellTiter-Glo® Luminescent Cell Viability Assay kit (Promega, G7571) and the plates were read at 490 nM by a Luminomitor (Tuner BioSystems, Sunnyvale, Calif.). The data was analyzed by Prism (Graphpad). As can be seen in FIG. 15, cell death was proportional to the concentration of 4A6, 11E7, and 16D10 monoclonal antibodies. Thus, the anti-Glypican-3 monoclonal antibodies were efficiently internalized by Hep-3b cells as compared to the hIgG1 isotype control antibody.

The monoclonal antibodies 4A6, 11E7, and 16D10 were also shown to be internalized by Hep-3b cells using an immunohistochemical staining assay. The cells, harvested with cell disassociation solution, were seeded at 104 cells per 100 ul of medium in each well of a 96-well plate and incubated with each monoclonal antibody at a concentration of 5 ug/ml in FACS buffer (PBS+5% FBS) for 30 minutes on ice. A human IgG1 isotype control was used as a negative control. The cells were washed twice, re-suspended in medium (100 ul per well) and then incubated with goat anti-human secondary antibody conjugated with phycoerythrin (Jackson ImmunoResearch Lab, PA) at a 1:100 dilution for 30 minutes. The cells were then washed with the media and either immediately imaged under a fluorescent microscope or incubated at 37° C. for imaging at later time points. The images of cell morphology and immunofluorescence intensity of the stained cells were taken with a Nikon TE200 camera at 0, 30 or 60 minutes as indicated in the FIG. 16. The fluorescence was only observed in the cells stained with the 4A6, 11E7, and 16D10 antibodies. No fluorescence was detected with the IgG1 control antibody.

As can be seen in FIG. 16, at 0 minutes after addition of the antibodies, the cells are stained at the cell surface. After 30 minutes, the cells have begun internalizing the antibodies. After 60 minutes, the antibodies have been almost completely internalized by the cells. This shows that the human anti-Glypican-3 monoclonal antibodies are specifically internalized upon binding to Glypican-3-expressing HCC cells.

Example 7

Anti-Glypican-3 Antibody Stability

Thermal Stability

The thermal stability of the anti-glypican-3 monoclonal antibodies was determined by calorimetric analysis of the melting temperatures for the 4A6, 11E7, and 16D10 antibodies. Calorimetric measurements of melting temperatures ($T_m$) were performed on a VP-Capillary DSC differential scanning microcalorimeter platform that was combined with an autosampler (MicroCal LLC, Northampton, Mass., USA). The sample cell volume was 0.144 mL. Denaturation data on the antibodies was obtained by heating the samples, at a concentration of 2.3 μM, from 30 to 95° C. at a rate of 1° C./min in phosphate-buffered saline (PBS) at pH 7.4. The same buffer was used in the reference cell to obtain the molar heat capacity by comparison. The observed thermograms were baseline corrected and normalized data analyzed based on a non-2-state model, using the software Origin v7.0. As shown in Table 2, 16D10 was observed to have the highest degree of thermal stability of the three anti-glypican-3 monoclonal antibodies.

TABLE 2

Differential scanning calorimetry:

| Anti-Glypican-3 | $T_m1$ (° C.) | $T_m2$ (° C.) | $T_m3$ (° C.) |
|---|---|---|---|
| 16D10 | 72.1 | 74.3 | 83.5 |
| 4A6 | 70.7 | 80.9 | 83.1 |
| 11E7 | 70.6 | 82.6 | 84.9 |

Chemical Stability Measured by Fluorescence Spectroscopy

The stability of 4A6, 11E7, and 16D10 were compared by measuring the midpoint of chemical denaturation by fluorescence spectroscopy. Fluorescence measurements of chemical denaturation was performed on a SPEX Fluorolog 3.22 equipped with a Micromax plate reader (SPEX, Edison, N.J.). The measurements were performed on antibody samples that had been equilibrated for 20 hours in 16 different concentrations of guanidinium hydrochloride in PBS buffer. The measurements were made in black, low volume, non-binding surface 384-well plates (Corning, Acton, Mass.) and required 1 μM of antibody in a well volume of 12 μL. Fluorescence was excited at 280 nm and the emission spectra were measured between 320 and 400 nm. The scan speed was 1 second per nm and slits were set to a 5 nm bandpass. A buffer blank was performed using PBS and automatically subtracted from the data. Data was fitted to a two-state denaturation model using the GraphPad Prism software. As shown in Table 3, 16D10 and 4A6 was observed to have similar stabilities but 11E7 showed biphasic unfolding.

TABLE 3

Chemical denaturation determined by fluorescence spectroscopy

| Clone | Unfolding Midpoint (M) |
|---|---|
| 4A6 | 2.84 |
| 16D10 | 2.74 |
| 11E7 | biphasic |

All references cited in this specification, including without limitation all papers, publications, patents, patent applications, presentations, texts, reports, manuscripts, brochures, books, internet postings, journal articles, periodicals, product fact sheets, and the like, one hereby incorporated by reference into this specification in their entireties. The discussion of the references herein is intended to merely summarize the assertions made by their authors and no admission is made that any reference constitutes prior art and Applicants' reserve the right to challenge the accuracy and pertinence of the cited references.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the dependant claims.

TABLE 4

Summary of sequence listing

| SEQ ID NO: | SEQUENCE |
|---|---|
| 1 | $V_H$ CDR1 a.a. 4A6 |
| 2 | $V_H$ CDR1 a.a. 11E7 |
| 3 | $V_H$ CDR1 a.a. 16D10 |
| 4 | $V_H$ CDR2 a.a. 4A6 |
| 5 | $V_H$ CDR2 a.a. 11E7 |
| 6 | $V_H$ CDR2 a.a. 16D10 |
| 7 | $V_H$ CDR3 a.a. 4A6 |
| 8 | $V_H$ CDR3 a.a. 11E7 |
| 9 | $V_H$ CDR3 a.a. 16D10 |
| 10 | $V_K$ CDR1 a.a. 4A6 |
| 11 | $V_K$ CDR1 a.a. 11E7 |
| 12 | $V_K$ CDR1 a.a. 16D10 |
| 13 | $V_K$ CDR2 a.a. 4A6 |
| 14 | $V_K$ CDR2 a.a. 11E7 |
| 15 | $V_K$ CDR2 a.a. 16D10 |
| 16 | $V_K$ CDR3 a.a. 4A6 |
| 17 | $V_K$ CDR3 a.a. 11E7 |
| 18 | $V_K$ CDR3 a.a. 16D10 |
| 19 | $V_H$ a.a. 4A6 |
| 20 | $V_H$ a.a. 11E7 |
| 21 | $V_H$ a.a. 16D10 |
| 22 | $V_K$ a.a. 4A6 |
| 23 | $V_K$ a.a. 11E7 |
| 24 | $V_K$ a.a. 16D10 |
| 25 | $V_H$ n.t. 4A6 |
| 26 | $V_H$ n.t. 11E7 |
| 27 | $V_H$ n.t. 16D10 |
| 28 | $V_K$ n.t. 4A6 |
| 29 | $V_K$ n.t. 11E7 |
| 30 | $V_K$ n.t. 16D10 |

TABLE 4-continued

| Summary of sequence listing | |
|---|---|
| SEQ ID NO: | SEQUENCE |
| 31 | $V_H$ 5-51 germline a.a. |
| 32 | $J_H$ JH4b germline a.a. |
| 33 | $V_K$ A27 germline a.a. |
| 34 | $J_K$ JK4 germline a.a. |
| 35 | $J_K$ JK1 germline a.a |
| 36 | Glypican-3 a.a. |
| 37 | $V_H$ n.t. with leader 4A6 |
| 38 | $V_H$ a.a. with leader 4A6 |
| 39 | $V_K$ n.t. with leader 4A6 |
| 40 | $V_K$ a.a. with leader 4A6 |

TABLE 4-continued

| Summary of sequence listing | |
|---|---|
| SEQ ID NO: | SEQUENCE |
| 41 | $V_H$ n.t. with leader 11E7 |
| 42 | $V_H$ a.a. with leader 11E7 |
| 43 | $V_K$ n.t. with leader 11E7 |
| 44 | $V_K$ a.a. with leader 11E7 |
| 45 | $V_H$ n.t. with leader 16D10 |
| 46 | $V_H$ a.a. with leader 16D10 |
| 47 | $V_K$ n.t. with leader 16D10 |
| 48 | $V_K$ a.a. with leader 16D10 |

What is claimed:

1. An isolated monoclonal antibody, or an antigen-binding portion thereof, wherein the antibody is selected from the group consisting of:

(i) an antibody, or antigen binding portion thereof, comprising:
a) a heavy chain variable region CDR1 comprising SEQ ID NO:1;
b) a heavy chain variable region CDR2 comprising SEQ ID NO:4;
c) a heavy chain variable region CDR3 comprising SEQ ID NO:7;
d) a light chain variable region CDR1 comprising SEQ ID NO:10;
e) a light chain variable region CDR2 comprising SEQ ID NO:13; and
f) a light chain variable region CDR3 comprising SEQ ID NO:16;

(ii) an antibody, or antigen binding portion thereof, comprising:
a) a heavy chain variable region CDR1 comprising SEQ ID NO:2;
b) a heavy chain variable region CDR2 comprising SEQ ID NO:5;
c) a heavy chain variable region CDR3 comprising SEQ ID NO:8;
d) a light chain variable region CDR1 comprising SEQ ID NO:11;
e) a light chain variable region CDR2 comprising SEQ ID NO:14; and
f) a light chain variable region CDR3 comprising SEQ ID NO:17; and (iii) an antibody, or antigen binding portion thereof, comprising:
a) a heavy chain variable region CDR1 comprising SEQ ID NO:3;
b) a heavy chain variable region CDR2 comprising SEQ ID NO:6;
c) a heavy chain variable region CDR3 comprising SEQ ID NO:9;
d) a light chain variable region CDR1 comprising SEQ ID NO:12;
e) a light chain variable region CDR2 comprising SEQ ID NO:15; and
f) a light chain variable region CDR3 comprising SEQ ID NO:18, wherein the antibody, or antigen-binding portion thereof, binds to human Glypican-3.

2. An isolated monoclonal antibody, or antigen binding portion thereof, selected from the group consisting of:

a) an antibody, or antigen binding portion thereof, comprising a heavy chain variable region comprising the amino acid sequence of SEQ ID NO:19 and a light chain variable region comprising the amino acid sequence of SEQ ID NO:22;
b) an antibody, or antigen binding portion thereof, comprising a heavy chain variable region comprising the amino acid sequence of SEQ ID NO:20 and a light chain variable region comprising the amino acid sequence of SEQ ID NO:23; and
c) an antibody, or antigen binding portion thereof, comprising a heavy chain variable region comprising the amino acid sequence of SEQ ID NO:21 and a light chain variable region comprising the amino acid sequence of SEQ ID NO:24, wherein the antibody, or antigen-binding portion thereof, binds to human Glypican-3.

3. An immunoconjugate comprising the antibody, or antigen-binding portion thereof, of claim 1 or 2, linked to a therapeutic agent.

4. A composition comprising the antibody, or antigen binding portion thereof, of claim 1 or 2 and a pharmaceutically acceptable carrier.

5. A method of inhibiting growth of tumor cells expressing Glypican-3, comprising contacting the cells with the antibody, or antigen-binding portion thereof, of claim 1, or 2, in an amount effective to inhibit growth of the tumor cells.

6. The method of claim 5, wherein the tumor cells are from liver tissue.

7. The method of claim 5, wherein the antibody, or antigen-binding portion thereof, is an immunoconjugate.

8. An isolated human monoclonal antibody, or antigen binding portion thereof, which competes for binding to Glypican-3 with the antibody of claim 2.

9. The antibody, or antigen-binding portion thereof, of claim 1 or 2, wherein the antibody, or antigen-binding portion thereof, is selected from the group consisting of a human antibody, a chimeric antibody, and a humanized antibody.

10. The antibody, or antigen-binding portion thereof, of claim 1, comprising:

a) a heavy chain variable region CDR1 comprising SEQ ID NO:1;

b) a heavy chain variable region CDR2 comprising SEQ ID NO:4;

c) a heavy chain variable region CDR3 comprising SEQ ID NO:7;

d) a light chain variable region CDR1 comprising SEQ ID NO:10;

e) a light chain variable region CDR2 comprising SEQ ID NO:13; and f) a light chain variable region CDR3 comprising SEQ ID NO:16.

11. The antibody, or antigen-binding portion thereof, of claim 1, comprising:

a) a heavy chain variable region CDR1 comprising SEQ ID NO:2;

b) a heavy chain variable region CDR2 comprising SEQ ID NO:5;

c) a heavy chain variable region CDR3 comprising SEQ ID NO:8;

d) a light chain variable region CDR1 comprising SEQ ID NO:11;

e) a light chain variable region CDR2 comprising SEQ ID NO:14; and f) a light chain variable region CDR3 comprising SEQ ID NO:17.

12. The antibody, or antigen-binding portion thereof, of claim 1, comprising:

a) a heavy chain variable region CDR1 comprising SEQ ID NO:3;

b) a heavy chain variable region CDR2 comprising SEQ ID NO:6;

c) a heavy chain variable region CDR3 comprising SEQ ID NO:9;

d) a light chain variable region CDR1 comprising SEQ ID NO:12;

e) a light chain variable region CDR2 comprising SEQ ID NO:15; and f) a light chain variable region CDR3 comprising SEQ ID NO:18.

13. The antibody, or antigen-binding portion thereof, of claim 2, comprising the amino acid sequence of SEQ ID NO:19 and a light chain variable region comprising the amino acid sequence of SEQ ID NO:22.

14. The antibody, or antigen-binding portion thereof, of claim 2, comprising the amino acid sequence of SEQ ID NO:20 and a light chain variable region comprising the amino acid sequence of SEQ ID NO:23.

15. The antibody, or antigen-binding portion thereof, of claim 2, comprising the amino acid sequence of SEQ ID NO:21 and a light chain variable region comprising the amino acid sequence of SEQ ID NO:24.

16. The antibody, or antigen-binding portion thereof, of claim 1 or 2, which is a full-length antibody of an IgG1 isotype.

17. The antibody, or antigen-binding portion thereof, of claim 1 or 2, which is a full-length antibody of an IgG4 isotype.

18. The antibody, or antigen-binding portion thereof, of claim 1 or 2, wherein the antibody is a hypofucosylated antibody.

19. The immunoconjugate of claim 3, wherein the therapeutic agent is a cytotoxin or a radioactive isotope.

20. A composition comprising the immunoconjugate of claim 3 and a pharmaceutically acceptable carrier.

21. The method of claim 5, wherein the tumor is hepatocellular carcinoma (HCC).

* * * * *

UNITED STATES PATENT AND TRADEMARK OFFICE

CERTIFICATE OF CORRECTION

PATENT NO. : 8,680,247 B2
APPLICATION NO. : 12/668965
DATED : March 25, 2014
INVENTOR(S) : Terrett et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 432 days.

Signed and Sealed this
Eleventh Day of August, 2015

Michelle K. Lee

Michelle K. Lee
*Director of the United States Patent and Trademark Office*